United States Patent
Henderson et al.

(10) Patent No.: US 9,891,804 B2
(45) Date of Patent: Feb. 13, 2018

(54) SELECTION AND DISPLAY OF BIOMARKER EXPRESSIONS

(71) Applicant: CLARIENT DIAGNOSTICS SERVICES, INC., Aliso Viejo, CA (US)

(72) Inventors: David LaVan Henderson, Niskayuna, NY (US); Michael S. Lazare, Aliso Viejo, CA (US)

(73) Assignee: GE HEALTHCARE BIO-SCIENCES CORP., Marlborough, MA (US)

(*) Notice: Subject to any disclaimer, the term of this patent is extended or adjusted under 35 U.S.C. 154(b) by 377 days.

(21) Appl. No.: 14/649,465

(22) PCT Filed: Dec. 6, 2013

(86) PCT No.: PCT/US2013/073698
§ 371 (c)(1),
(2) Date: Jun. 3, 2015

(87) PCT Pub. No.: WO2014/089499
PCT Pub. Date: Jun. 12, 2014

(65) Prior Publication Data
US 2015/0301732 A1     Oct. 22, 2015

Related U.S. Application Data

(60) Provisional application No. 61/889,820, filed on Oct. 11, 2013, provisional application No. 61/828,890, (Continued)

(51) Int. Cl.
*G06F 3/0484*     (2013.01)
*G06F 3/048*      (2013.01)
(Continued)

(52) U.S. Cl.
CPC ........ *G06F 3/04847* (2013.01); *G01N 35/00* (2013.01); *G06F 3/048* (2013.01);
(Continued)

(58) Field of Classification Search
None
See application file for complete search history.

(56) References Cited

U.S. PATENT DOCUMENTS

2008/0104532 A1   5/2008   Stambaugh
2009/0290794 A1   11/2009  Marchesotti
(Continued)

FOREIGN PATENT DOCUMENTS

WO     2009072098     5/2014

OTHER PUBLICATIONS

European Search Report regarding EP Application No. 13859805.7, dated Jun. 27, 2016, 8 pages.
(Continued)

*Primary Examiner* — Tuan S Nguyen

(57) ABSTRACT

Embodiments provide a user interface including an image panel for displaying a field of view corresponding to an image, or a portion of an image, of a biological specimen, and a biomarker panel for displaying thumbnail images for simultaneously viewing different aspects of a region within the field of view. Upon selection or update of the selected region of the field of view, the thumbnail images may be accordingly updated automatically to display the newly selected region. The image panel may include an interest region selection component for delineating a region within the field of view. The interest region selection component may be overlaid over a portion of the field of view displayed in the image panel, and may be used by a user to select or
(Continued)

update the region within the field of view displayed in the biomarker panel. Images of interest may be saved to an electronic record.

44 Claims, 37 Drawing Sheets

Related U.S. Application Data filed on May 30, 2013, provisional application No. 61/734,032, filed on Dec. 6, 2012.

(51) Int. Cl.
*G01N 35/00* (2006.01)
*G06F 19/26* (2011.01)
*G06F 3/0486* (2013.01)
*G06T 7/00* (2017.01)
*G06F 19/20* (2011.01)

(52) U.S. Cl.
CPC ........ *G06F 3/0486* (2013.01); *G06F 3/04842* (2013.01); *G06F 19/26* (2013.01); *G06T 7/0012* (2013.01); *G01N 2035/0091* (2013.01); *G06F 19/20* (2013.01); *G06T 2200/24* (2013.01); *G06T 2207/10004* (2013.01); *G06T 2207/10056* (2013.01); *G06T 2207/30004* (2013.01)

(56) References Cited

U.S. PATENT DOCUMENTS

| | | |
|---|---|---|
| 2010/0211409 A1 | 8/2010 | Kotula et al. |
| 2011/0091091 A1 | 4/2011 | Sarachan et al. |
| 2012/0069049 A1 | 3/2012 | Howe et al. |
| 2012/0084732 A1* | 4/2012 | Filippov ............... G06F 3/0482 715/838 |
| 2012/0147010 A1 | 6/2012 | Schmidt et al. |
| 2012/0162228 A1 | 6/2012 | Yamane et al. |
| 2013/0287283 A1* | 10/2013 | Kamath ................. G09G 5/026 382/133 |

OTHER PUBLICATIONS

International Search Report and Written Opinion for International Application No. PCT/US13/73698, dated May 12, 2014, 11 pages.

* cited by examiner

1900 http://server/TileServer/Handler.ashx?Info=true
&<additional_image_parameters>

2002     <ImageMetrics>
2004     <ImageHeight>2598</ImageHeight>
2006     <ImageWidth>2598</ImageWidth>
2008     <TileHeight>128</TileHeight>
2010     <TileWidth>128</TileWidth>
        <MinimumPyramidLevel>7</MinimumPyramidLevel>
2012     <MaximumPyramidLevel>12</MaximumPyramidLevel>
        </ImageMetrics>

SELECTION AND DISPLAY OF BIOMARKER EXPRESSIONS

This application is a filing under 35 U.S.C. 371 of international application number PCT/US2013/073698, filed Dec. 6, 2013, which claims priority to U.S. application No. 61/734,032, filed Dec. 6, 2012, U.S. application No. 61/828,890, filed May 30, 2013 and U.S. application No. 61/889,820, filed Oct. 11, 2013 the entire disclosures of each of which are hereby incorporated by reference.

BACKGROUND OF THE INVENTION

Examination of tissue specimens that have been treated to reveal the expression of biomarkers is a known tool for biological research and clinical studies. One such treatment involves the use of antibodies or antibody surrogates, such as antibody fragments, that are specific for biomarkers, commonly proteins, of interest. Such antibodies or antibody surrogates can be directly or indirectly labeled with a moiety capable, under appropriate conditions, of generating a signal. For example, a fluorescent moiety can be attached to an antibody to interrogate the treated tissue for fluorescence. The signal obtained is commonly indicative of both the presence and the amount of a biomarker present.

SUMMARY OF THE INVENTION

In accordance with one exemplary embodiment, a computer-implemented method is provided for displaying expression levels of one or more biomarkers in a field of view of a biological specimen. The method includes rendering a graphical user interface on a visual display device. The graphical user interface includes a main image panel and a biomarker panel. The method includes receiving user input selecting a field of view corresponding to a selected biological specimen, and rendering, on the main image panel, a first image of the selected field of view corresponding to the biological specimen. The method includes rendering, overlaid on the first image in the main image panel, an interest region selection component enabling a user to select a first region within the first image. The method also includes rendering, on the biomarker panel, a first set of thumbnail images corresponding to the first region in the first image, the first set of thumbnail images representing expression levels of a set of biomarkers. The method further includes receiving user input, on the main image panel, selecting a second region in the first image, and based on the user input selecting the second region in the first image, updating the biomarker panel to replace the first set of thumbnail images with a second set of thumbnail images corresponding to the second region in the first image and representing expression levels of the set of biomarkers.

In accordance with another exemplary embodiment, a computer system is provided for displaying expression levels of one or more biomarkers in a field of view of a biological specimen. The computer system includes a visual display device for displaying a graphical user interface, and a computer processor coupled to the visual display device. The computer processor is programmed or configured to render the graphical user interface on the visual display device, the graphical user interface including a main image panel and a biomarker panel. The computer processor is programmed or configured to receive user input selecting a field of view corresponding to a selected biological specimen, and render, on the main image panel, a first image of the selected field of view corresponding to the biological specimen. The computer processor is programmed or configured to render, overlaid on the first image in the main image panel, an interest region selection component enabling a user to select a first region within the first image. The computer processor is also programmed or configured to render, on the biomarker panel, a first set of thumbnail images corresponding to the first region in the first image, the first set of thumbnail images representing expression levels of a set of biomarkers. The computer processor is further programmed or configured to receive user input, on the main image panel, selecting a second region in the first image, and based on the user input selecting the second region in the first image, update the biomarker panel to replace the first set of thumbnail images with a second set of thumbnail images corresponding to the second region in the first image and representing expression levels of the set of biomarkers.

In accordance with another exemplary embodiment, one or more non-transitory computer-readable media are provided. The non-transitory computer-readable media have encoded thereon one or more computer-executable instructions that, when executed on a computing device, perform a method for displaying expression levels of one or more biomarkers in a field of view of a biological specimen. The method includes rendering a graphical user interface on a visual display device. The graphical user interface includes a main image panel and a biomarker panel. The method includes receiving user input selecting a field of view corresponding to a selected biological specimen, and rendering, on the main image panel, a first image of the selected field of view corresponding to the biological specimen. The method includes rendering, overlaid on the first image in the main image panel, an interest region selection component enabling a user to select a first region within the first image. The method also includes rendering, on the biomarker panel, a first set of thumbnail images corresponding to the first region in the first image, the first set of thumbnail images representing expression levels of a set of biomarkers. The method further includes receiving user input, on the main image panel, selecting a second region in the first image, and based on the user input selecting the second region in the first image, updating the biomarker panel to replace the first set of thumbnail images with a second set of thumbnail images corresponding to the second region in the first image and representing expression levels of the set of biomarkers.

In accordance with another exemplary embodiment, images displayed may be captured and uploaded into a retrievable record.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 19 shows an example of an image metrics request that may be generated by a client computing device.

FIG. 20 shows an example of an XML-based response to the image metrics request of FIG. 19.

FIG. 24 depicts an alternate viewer of the present invention.

FIG. 26 depicts a 10× display of an mDAB image of CD30 on the viewer of FIG. 24.

FIG. 32 depicts the selectable orientation of the two images of FIG. 31.

DETAILED DESCRIPTION OF THE PREFERRED EMBODIMENTS

Figure 1:
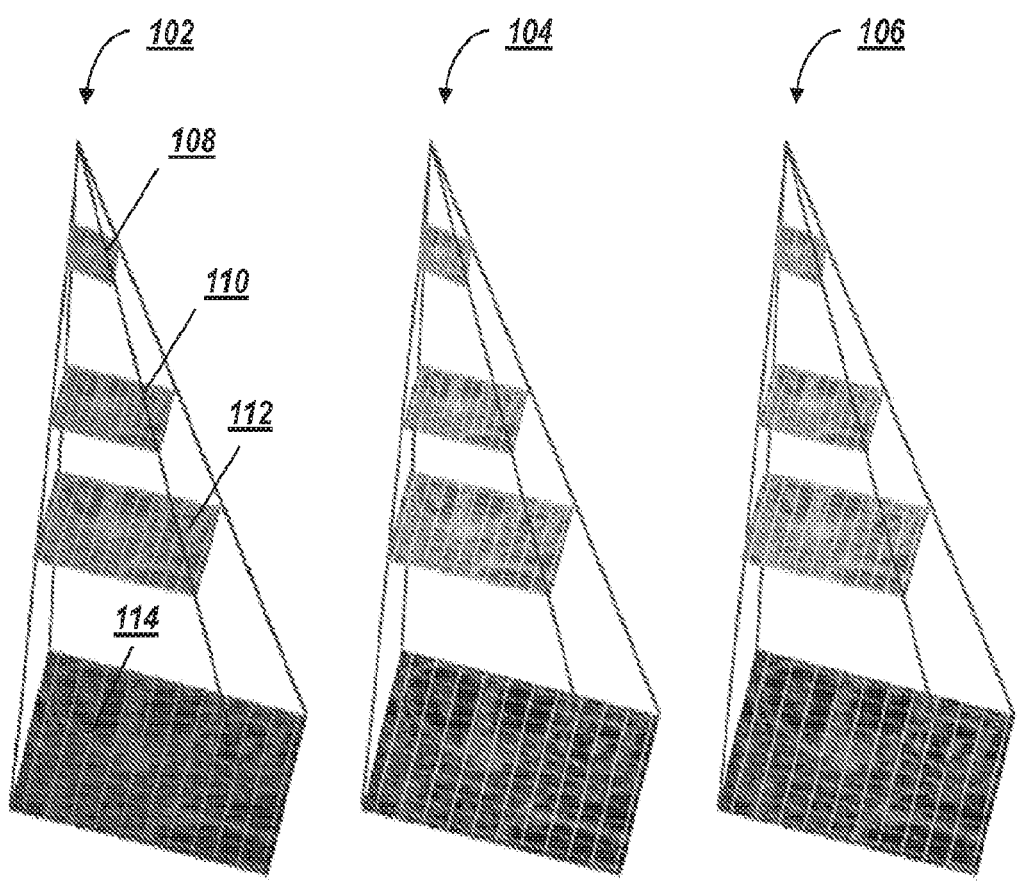
FIGS. 1A-1C illustrate exemplary data structures for storing biomarker expression data.

Embodiments disclosed herein include methods, systems, and devices for selectively visualizing biological specimens and tissues and data corresponding to the biological specimens, for example, expression levels of one or more biomarkers, one or more morphological features, results of one or more image analysis methods, and the like. Exemplary embodiments enable structured, yet rapid, flexible and user-friendly, displays of biological specimens that facilitate biological research applications and allow pathologists to arrive at objective and repeatable diagnoses and disease or condition models.

Certain exemplary embodiments provide a split screen display for simultaneously viewing different portions of a selected field of view of a biological specimen. Depending on the resolution of the displayed field of view, the present invention contemplates that a field of view may show all or a portion of an image of the biological specimen. It is contemplated that in most applications of the present invention, it will be desirable to select a field of view which is only a portion, or a smaller region of interest, of the biological specimen image so as to allow higher magnification displays of that portion of the biological specimen image in an image panel. Thus, when a field of view is said to 'correspond to a biological specimen', the present invention intends that the field of view represents an image, or a portion of an image, of the biological specimen. An image panel in the split screen display may include or be split into two or more non-overlapping image sub-panels for displaying two or more contiguous portions of the field of view so that a sub-panel displays to a single portion of the field of view and so that the collection of two or more image sub-panels cooperatively displays the entire field of view. The portions of the field of view are precisely and seamlessly aligned at boundaries of the sub-panels. Different display types may be used to display the portions of the field of view in the sub-panels. Different display types may include, but are not limited to, expression of one or more biomarkers, display of one or more morphological features, display of one or more analysis results, and display as one or more visualization types.

Certain exemplary embodiments provide a user interface including an image panel for displaying a field of view of a biological specimen, and a biomarker panel for displaying thumbnail images for simultaneously viewing different aspects of a region within the field of view (e.g., expression levels of different biomarkers in the region). Upon selection or update of the selected region of the field of view, the thumbnail images may be accordingly updated automatically to display the newly selected region. The image panel may include an interest region selection component for delineating a region within the field of view. The interest region selection component may be overlaid over a portion of the field of view displayed in the main image panel, and may be used by a user to select or update the region within the field of view displayed in the biomarker panel.

Exemplary Tissue Imaging Techniques

Embodiments taught herein use biological image data corresponding to multiplexed biomarker images that may be generated through known techniques such as a staining-bleaching-restaining. Generally, this technique involves staining a biological specimen with a fluorophore labeled probe to generate a signal for one or more probe bound biomarkers, chemically bleaching these signals, and re-staining the specimen to generate signals for some additional biomarkers. The chemical bleaching step is convenient because there are only a limited number of signals that can be readily differentiated from each other so only a limited number of biomarkers can be examined in a particular step. With bleaching, a tissue sample may be re-probed and re-evaluated for multiple steps. This cycling method may be used on formalin fixed paraffin embedded tissue (FFPE) samples and cells. Digital images of the specimen are collected after each staining step. The successive images of the specimen can conveniently be kept in registry using morphological features such as DAPI stained cell nuclei, the signal of which is not modified by the chemical bleaching method. The aforementioned is one example of a multiplexing technique, and the system used to stain, bleach, and image the samples is an example of a multiplexing platform.

Another approach includes examining frozen biological specimens by staining them iteratively and photo bleaching the labels from the previous staining step before applying the next set of stains. The strength of the fluorescent signal associated with each biomarker evaluated is then extracted from the appropriate image.

The generated images may illustrate expression of one or more biomarkers by individual cells within a larger tissue sample of cells. The tissue sample may be a group of cells from a cell culture or a sample of an organ, a tumor, or a lesion. The tissue sample may also be part of a group of specimens of similar tissue from different subjects, known as a cohort. These groups of tissue samples may represent one or more disease or condition models, different stages within a disease or condition model, or one or more responses to treatment of a disease or condition.

The techniques of tissue treatment and examination have been refined so that the level of expression of a given biomarker in a particular cell or even a compartment of the given cell, such as the nucleus, cytoplasm or membrane, can be quantitatively determined. The boundaries of these compartments or the cell as a whole are located using known histological stains. Commonly, the treated tissue is examined with digital imaging and the level of different signals emanating from different biomarkers can consequently be readily quantified.

Images of each stained field of view of a biological specimen are generated using known techniques, such as with a digital camera coupled to an appropriate microscope and appropriate quality control routines. Automated image registration and analysis may also be used to quantify the biomarker expression levels for individual delineated cells, collection of cells or even sub-cellular compartments, such as nucleus, cytoplasm and membrane. The data values resulting from the multiplexing and image analysis of cells or sub-cellular components may be stored alone or in conjunction with results of further analysis, e.g., segmentation analysis. A database may preserve the expression levels of the biomarkers (e.g., as different channels of data) including an identification of the source specimen and an identification the location within the tissue from which the specimen was drawn. The identified location may indicate the particular cell and/or tissue from which a particular measurement was derived, and may also include an identification of the compartment, nucleus, cytoplasm or membrane associated with the measurement. The data values associated with the may be stored in a database, which may be maintained in a storage device or in a networked server.

Exemplary embodiments are described below with reference to the drawings. One of ordinary skill in the art will recognize that exemplary embodiments are not limited to the illustrative embodiments, and that components of exemplary systems, devices and methods are not limited to the illustrative embodiments described below.

Exemplary Data Structures for Storing Biological Image Data

Exemplary embodiments may store image data on biological specimens in a manner that allows generation of images at different resolutions for display on graphical user interfaces. A multiplexed image of a biological specimen may be processed by a computing device to isolate different channels of data corresponding to the different markers used to form the multiplexed image. These markers may be biomarkers and/or stains that express morphological features (e.g., nuclei, membranes, cytoplasms) in the biological specimen.

In exemplary embodiments, pixel-level image data corresponding to each channel in a multiplexed image may be stored in a tiled multi-resolution or tiled pyramidal data structure which is suitable for streaming data. In this data structure, a plurality of images corresponding to different resolutions of the same channel of image data is stored in a pyramidal format in an order of increasing or decreasing resolution. At each resolution level, the pixel-level data of the image is divided into a plurality of blocks or tiles. The tiled multi-resolution format maximizes the speed and efficiency of data access and transmission. Individual images tiles may be rapidly accessed and streamed at any resolution with minimal server overhead, which is especially important in accessing high resolution image data. That is, data corresponding to a sequence of one or more tiles may be sent from the data storage and received by a data requesting entity. Since data is available at different resolutions, image processing is not necessary to conform to the image data to a requested level of resolution.

In creating a tiled multi-resolution data structure, an image corresponding to a single channel of data (e.g., a single biomarker) may be processed by a computing device to generate two or more versions of the same image at different resolutions. Any conventional technique for generating lower resolution versions of images may be used. The images corresponding to the single channel of data may then be stored in a pyramidal format in an order of increasing or decreasing resolution. FIG. 1A illustrates a tiled pyramidal data structure 102 for storing expression data of a first biomarker in a biological specimen; FIG. 1B illustrates a tiled pyramidal data structure 104 for storing expression data of a second biomarker in the biological specimen; and FIG. 1C illustrates a tiled pyramidal data structure 106 for storing expression data of a third biomarker in the biological specimen. The exemplary data structure 102 of FIG. 1A includes four images 108, 110, 112, 114 corresponding to data on the same marker expression or morphology in the same biological specimen at four different resolution levels, ordered in increasing resolutions.

Once a pyramidal data structure is generated for a single channel of data, the pixel-level data on each image at the different resolution layers is divided into blocks or tiles. An image may be divided into any suitable number of tiles. For example, the image may be divided into tiles that are 512 pixels wide by 512 pixels high. The storage device storing the tiled multi-resolution data structure may uniquely identify each data structure and each tile in the data structure for rapid access based on requests. For example, each tile in the data structure can be indexed at each level in the pyramid and/or two-dimensional coordinates can be associated with each tile at each level in the pyramid.

Although exemplary embodiments are described in connection with tiled multi-resolution data storage structures, one of ordinary skill in the art will recognize that other suitable storage structures may be used as well or in the alternative.

In one embodiment, a computing device providing any of the user interfaces as described herein may include a storage device for storing image data on biological specimens in tiled multi-resolution data structures.

In another embodiment, a computing device providing any of the user interfaces as described herein may access image data from a remote server storing the tiled multi-resolution data structures. In this case, the computing device running a user interface may determine the tiles of data that are selectively required for its purposes, and may request only the selective tiles from the server. That is, image data on the entire biological specimen may not be requested or preloaded into the user interface in some embodiments; but, rather, only those sets of image data that are required at a given time may be requested from the server. This minimizes server overhead in servicing the requests and reduces the amount of image data that needs to be transferred to the computing device for its user interface, thereby making the user interface rapid and efficient and highly responsive to user input and requests. In response to the request for data, the server may access the requested tiles of data and, in some cases, perform analysis or validation of the data. The server may then transfer the tiles of data to the computing device in a streaming manner. That is, data corresponding to a sequence of one or more tiles may be sent by the server and received by a computing device requesting the data.

Exemplary Split Screen Display of a Biological Specimen

In some exemplary embodiments, a split screen display is enabled for simultaneously viewing different aspects of two or more portions, or regions, of a selected field of view of a biological specimen. More specifically, an image panel is provided for displaying a selected field of view of a biological specimen. The image panel in the split screen display may include or be split into two or more non-overlapping image sub-panels for displaying two or more portions of the field of view so that a sub-panel displays a single portion of the field of view and so that the collection of two or more image sub-panels cooperatively displays the entire field of view. The portions of the field of view may be contiguous. The portions of the field of view are precisely and seamlessly aligned at the boundaries of the sub-panels. In exemplary embodiments, within a specified field of view of a biological specimen, the image sub-panels may be a matched set, having the same size and resolution levels. The image sub-panels may be properly registered so that the tissue features align properly across the sub-panels when the field of view is displayed in the split screen view.

In one example in which two image sub-panels are provided, a first sub-panel may display a first of two portions of the field of view and a second sub-panel may display a second of the two portions of the field of view. Even after being split into sub-panels, the image panel continues to display the entire field of view in a seamless manner. For all embodiments, the present invention contemplates that the terms "seamless" and "contiguous" may also apply to image panel displays having a border line which delineates between the sub-panels, such that the border line covers over one or both of the adjoining edges of the sub-panels or such that the adjoining edges of the sub-panels are separated across the width of the provided border line.

In exemplary embodiments, different display types may be used to display the portions of the field of view in the different image sub-panels. Different display types used in exemplary embodiments may include, but are not limited to, expression of one or more biomarkers, display of one or more morphological features, display of one or more analysis results, display according to one or more visualization types (e.g., binary heat-map, discrete heat-map, continuous heat-map, intensities of greyscale values of grey or color pixels, color blend of two or more biomarker expressions), combinations of any of the above types, and the like.

In one example in which two image sub-panels are presented, a first sub-panel may display expression levels of a first biomarker in a first portion of the field of view, and a second sub-panel may display expression levels of a second biomarker in a second portion of the field of view. In another example in which two image sub-panels are presented, a first sub-panel may display expression levels of a biomarker in a first portion of the field of view, and a second sub-panel may display one or more morphological features in a second portion of the field of view. In another example in which two image sub-panels are presented, a first sub-panel may display one or more morphological features in a first portion of the field of view, and a second sub-panel may display one or more morphological features in a second portion of the field of view.

The split screen display capability provided by exemplary embodiments is useful for comparing how different aspects of the biological specimen change or vary over different portions of the field. For example, the split screen display may enable a medical professional or researcher to analyze different biomarkers or combinations of biomarkers over different locations of interest (e.g. a cell or cluster of cells expressing one or more imaged biomarkers).

An advantageous feature of the split screen display is that it does not require an image of a biological specimen or an image of a field of view displayed in the main image panel to be fully loaded into the computer memory prior to creation of the image sub-panels. Instead, a user may select desired portions of a field of view for display in the sub-panels, which causes only image data relevant to the user selections to be selectively loaded into the computer memory for the split screen display.

One of ordinary skill in the art will recognize that any suitable combination of different display types may be used to display a field of view in a split image panel. For example, the different image sub-panels of an image panel may be selected to display zero, one or more different biomarker expression; zero, one or more morphological features; zero, one or more different analysis results; zero, one or more different visualization types; or any combinations of the above.

An exemplary image panel may be split into or provided with any suitable number of sub-panels based on one or more factors including, but not limited to, user preference, display size, display resolution, and the like. Exemplary numbers of sub-panels formed or provided in an image panel may include, but are not limited to, 1, 2, 3, 4, 5, 6, 7, 8, 9, 10, 11, 12, 13, 14, 15, and the like.

The image panel may be loaded as pre-split into two or more image sub-panels that are simultaneously displayed in the image panel. Alternatively, the image panel may be split after being loaded upon receiving a user input or based on a display setting.

Two or more exemplary image sub-panels may be organized in an image panel with respect to one another in any suitable manner, for example, horizontally, vertically, in a grid organization. The spatial organization of the image sub-panels may correspond to the spatial organization of the displayed portions in the field of view so that the portions of the field of view are precisely and seamlessly aligned at the boundaries of the sub-panels. The image sub-panels are properly registered so that the tissue features align properly when the field of view is displayed in the split screen view. For example, horizontally organized left and right sub-panels may seamlessly display left and right portions of the field of view, while vertically organized top and bottom sub-panels may seamlessly display top and bottom portions of the field of view.

Figure 2:
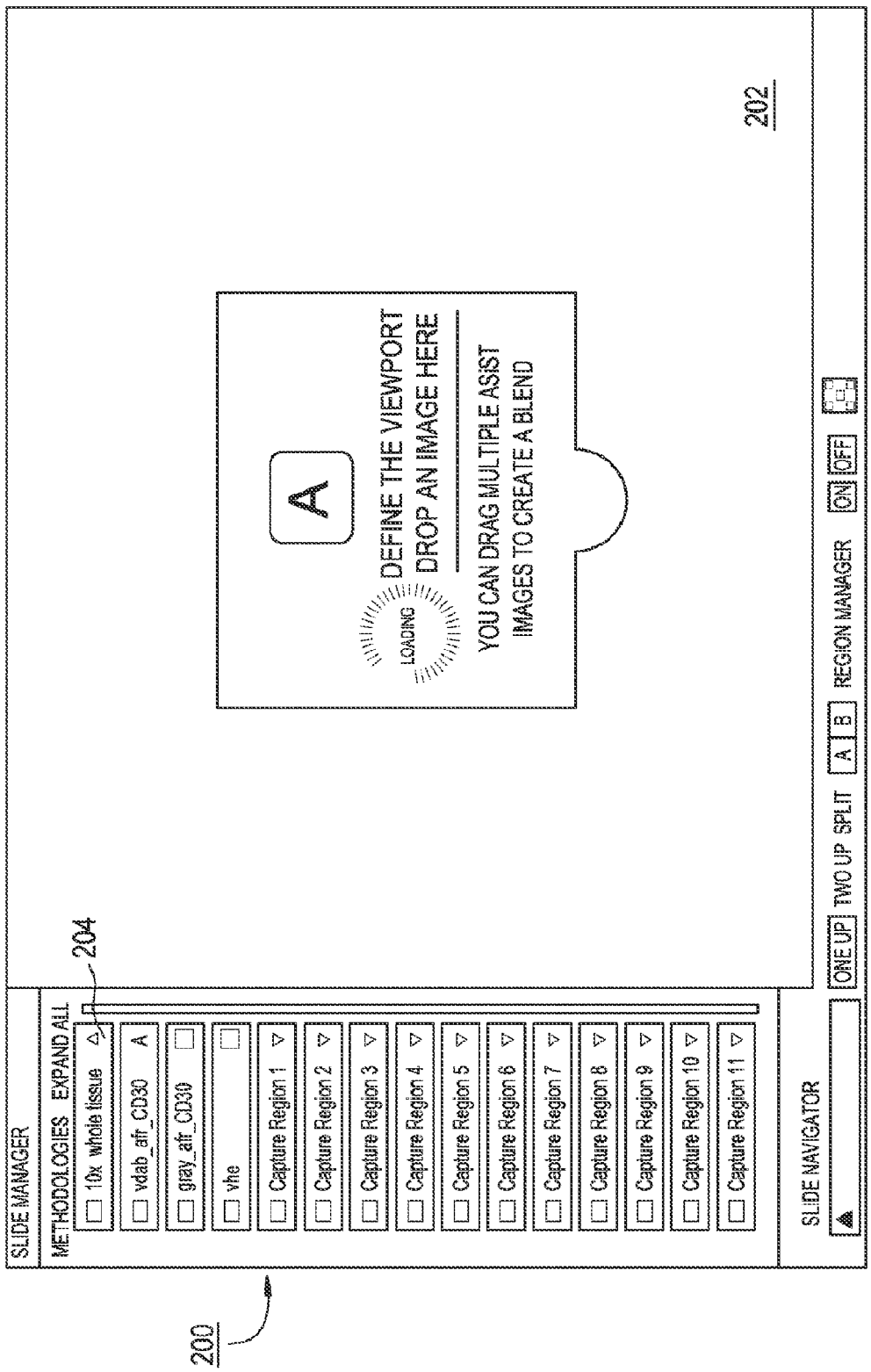
FIG. 2 illustrates an exemplary user interface for displaying one or more fields of view of a biological specimen.

FIGS. 2-7 illustrate an exemplary graphical user interface (GUI), also referred to herein as a 'viewer', 200 that may be used to implement a split screen display, although other suitable user interfaces may be used. FIG. 2 illustrates the GUI 200 including a main image panel 202 for displaying a field of view of a biological specimen. A user may select a desired biological specimen (e.g., a slide/spot) for display in the main image panel 202. The biological specimen may be selected using the GUI 200, a command panel, or any other suitable means.

A selected biological specimen may have corresponding stored image data that may be displayed in the GUI 200. A display type selection component 204 may be used by a user to select one or more display types available for display in the main image panel 202. Exemplary display types used in exemplary embodiments may include, but are not limited to, expression of one or more biomarkers, display of one or more morphological features, display of one or more analysis results, display according to one or more visualization types (e.g., binary heat-map, discrete heat-map, continuous heat-map, intensities of greyscale values of grey or color pixels, color blend of two or more biomarker expressions), combinations of any of the above types, and the like. For example, the display type selection component 204 of FIGS. 2-7 indicates that, for the selected biological specimen, a VDAB visualization type is available for the CD30 biomarker, a grayscale visualization type is available for the CD30 biomarker, and a VHE image is available.

Figure 3:
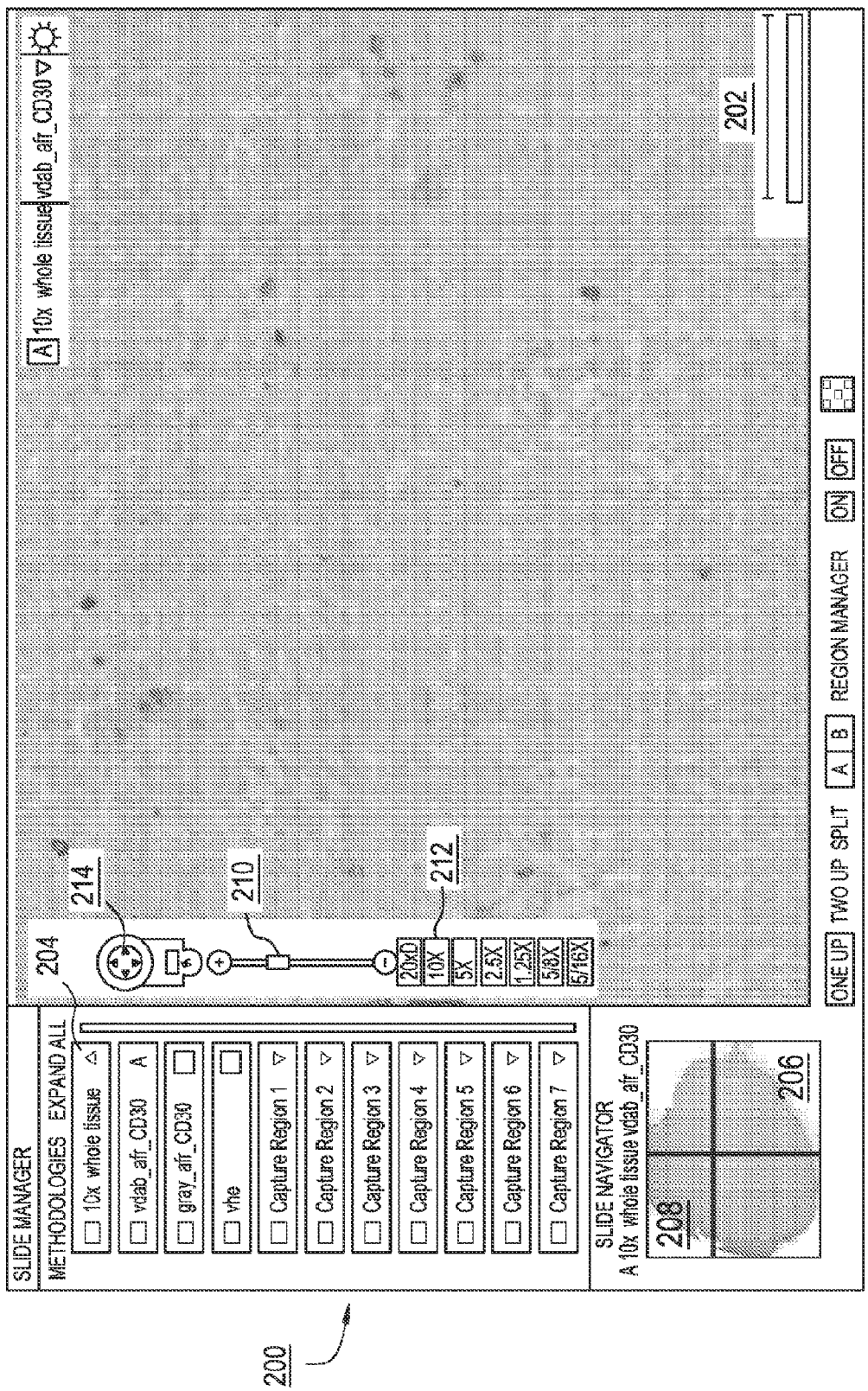
FIG. 3 illustrates the user interface of FIG. 2, displaying expression levels of a biomarker in a field of view in a main image panel.

Upon receiving a user selection of a display type for the selected biological specimen (e.g., by clicking the selection and/or dragging it onto the main image panel 202), the main image panel 202 may render the field of view displayed according to the selected display type. FIG. 3 illustrates the display of a field of view of a biological specimen in the main image panel 202, representing a VDAB visualization type for the CD30 biomarker.

Upon display of a field of view in the main image panel 202, the GUI 200 may be updated to include an image navigation component 206 (illustrated in FIGS. 3-7) that displays an image of the overall biological specimen of which the field of view displayed in the main image panel 202 is a part. The image navigation component 206 displays the biological specimen in accordance with the display type selected by the user, for example, a VDAB visualization type for the CD30 biomarker in FIG. 3.

The image navigation component 206 may include a field of view selection component 208 (e.g. a reticle or any other suitable component), illustrated in FIGS. 3-7, for delineating the field of view within the overall display of the biological specimen. This allows the user to generally locate where the field of view (displayed in the main image panel 202) can be found in the overall biological specimen (displayed in the image navigation component 206). The field of view selection component 208 may be an interaction component for enabling a user to select any field of view in the biological specimen displayed in the image navigation component 206 so that the main image panel 202 is updated to display the selected field of view. Similarly, a user may use the field of view selection component 208 to browse different fields of view in a continual and smooth manner. The user may select the field of view selection component 208 (e.g., by clicking on it with a mouse cursor) and drag and drop the field of view selection component 208 on a new different field of view. In an exemplary embodiment, upon dropping the field of view selection component 208 by releasing the cursor, the main image panel 202 may be automatically updated to display the new field of view. In an exemplary embodiment, the main image panel 202 may also be automatically updated while the field of view selection component 208 is dragged by the user. In some embodiments, this update may be performed in real time as the user interacts with the user interface or may, alternatively, be performed after a time lag after the user selects a new location for the field of view.

In some embodiments, the image navigation component 206 is smaller than the main image panel 202 and provides a lower resolution display of the biological specimen. In other embodiments, the image navigation component 206 may be the same size as or larger than the main image panel 202.

As illustrated in FIG. 3, the main image panel 202 may include a zoom input tool 210 for allowing a user to input a particular level of zoom or a relative level of zoom (e.g., using a zoom slider and/or zoom buttons). The current relative zoom level may be indicated on the image panel in a zoom indicator 212. In some cases, the zoom level may be reset to a default level by the user or automatically by the system. In some exemplary embodiments, the user interface may allow zooming in and out using a pointing device directly on the image on the main image panel 202, for example, by clicking the right button on a mouse. In some exemplary embodiments, the user interface may allow zooming in and out using keyboard shortcuts, for example, using a combination of the "Ctrl" key and the "+" key to zoom in and using a combination of the "Ctrl" key and the "−" key to zoom out. When the main image panel 202 is updated according to a new zoom level, the field of view selection component 208 in the image navigation component 206 may be automatically updated to correctly delineate the updated field of view shown in the main image panel 202. In an exemplary embodiment, a computing device running the user interface may determine that new zoom level requires image data from a different resolution level in a tiled multi-resolution data structure, and may retrieve one or more tiles of image data from the resolution level.

As illustrated in FIG. 3, the main image panel 202 may include a pan input tool 214 for panning to a new field of view in the biological specimen. The pan input tool 214 may allow a user to input a particular level of panning in the biological specimen or a relative level of panning using a slider in order to adjust the field of view displayed in the main image panel 202. In some cases, the pan settings may be reset to display the initially displayed field of view in the main image panel 202. In some exemplary embodiments, the user interface may allow panning using a pointing device directly on the main image panel 202, for example, by clicking the left button on a mouse over the image, dragging the cursor across the image and releasing it to display a new field of view. In some exemplary embodiments, the user interface may allow panning using keyboard shortcuts.

In one embodiment, the main image panel 202 may be updated to display the new field of view upon release of the cursor. In another embodiment, the main image panel 202 may be updated in a real time manner as the user drags the cursor across the image or may, alternatively, be performed after a time lag after the user moves the selected field of view. In an exemplary embodiment, a computing device running the user interface may determine that a different set of tiles of image data is required to represent the new field of view, and may retrieve the set of tiles from a tiled multi-resolution data structure.

In some embodiments, the pan input tool 214 may also enable a user to rotate the field of view displayed in the main image panel 202.

When the main image panel 202 is updated to display a new field of view, the field of view selection component 208 in the image navigation component 206 may be automatically updated to correctly indicate the location of the new field of view in the specimen.

Figure 4:
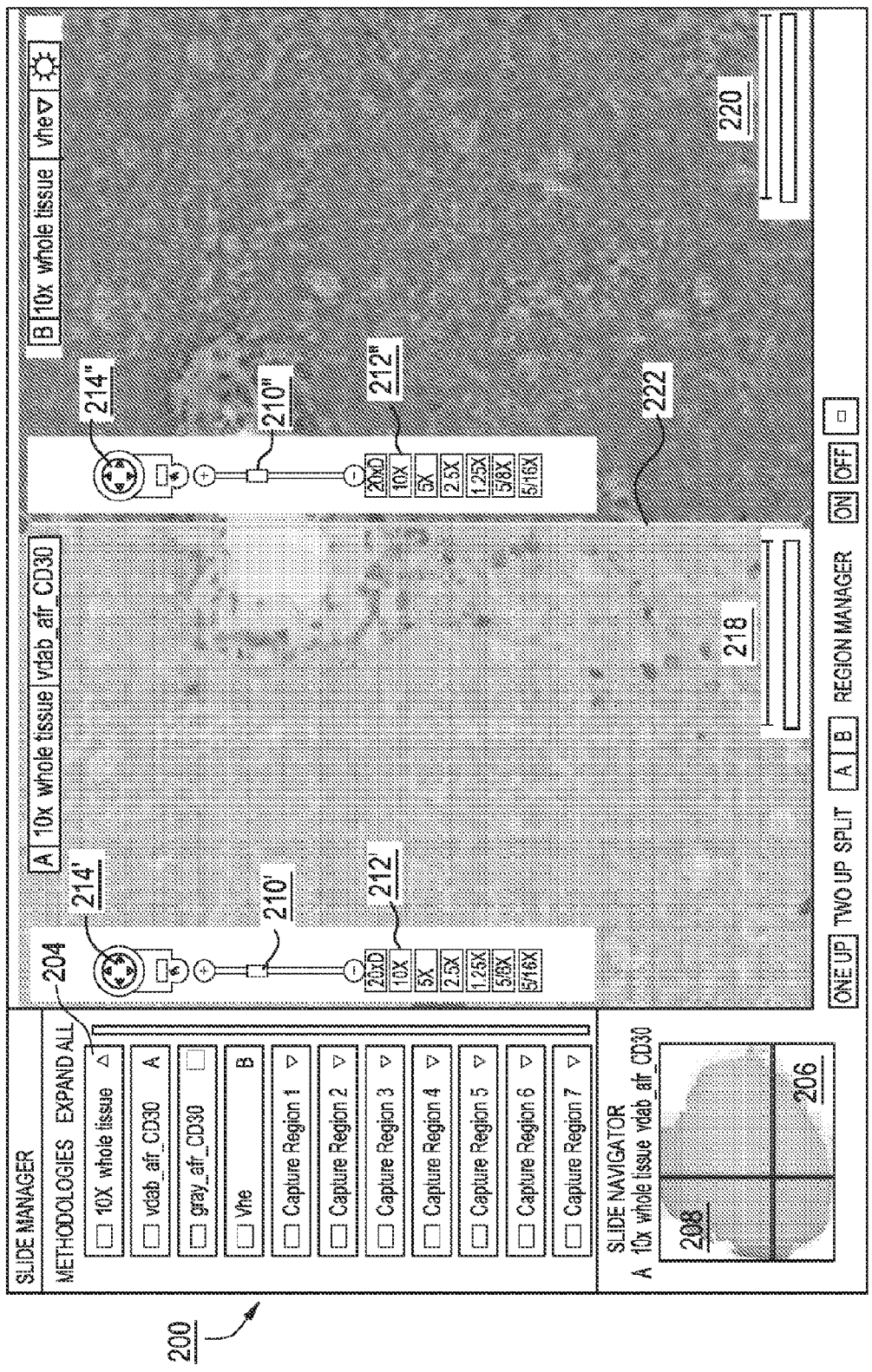
FIG. 4 illustrates the user interface of FIG. 3, displaying the main image panel split into two image sub-panels that are horizontally disposed relative to each other.
Figure 5:
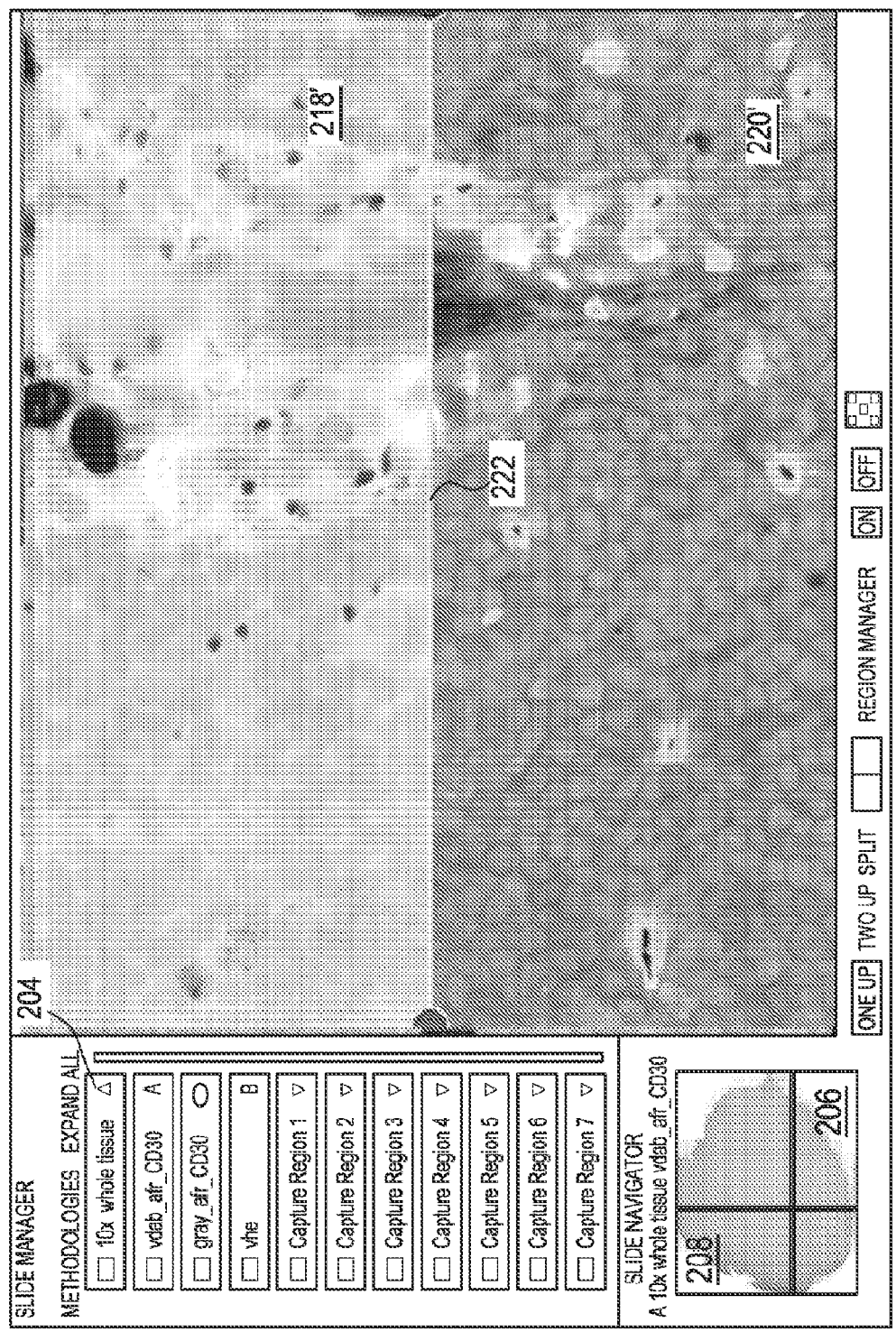
FIG. 5 illustrates the user interface of FIG. 3, displaying the main image panel split into two image sub-panels that are vertically disposed relative to each other.

As illustrated in FIG. 4, the main image panel 202 may include one or more splitter components 216 that allow a user to indicate that the main image panel 202 should be split into or provided with two or more image sub-panels for simultaneous display, for example, sub-panels 218, 220. In an exemplary embodiment, the user may select how many sub-panels are to be created for simultaneous display. Alternatively, the system may generate a number of sub-panels indicated in a stored default setting. In an exemplary embodiment, the user may select how the sub-panels are to be organized in the image panel 202. Alternatively, the system may organize the sub-panels according to a stored default setting. In exemplary embodiments, a user may be allowed to remove the image sub-panels from the main image panel 202.

The display type selection component 204 may be used by a user to indicate the display types for display in the sub-panels 218, 220. Upon receiving a user selection of a display type for the sub-panels (e.g., by clicking the selections and dragging them onto the sub-panels), exemplary embodiments may display contiguous portions of the field of view (selected in the image navigation component 206) in the different sub-panel 218, 220 so that the collection of sub-panels shows the overall field of view. Each sub-panel may render a different display type for the corresponding portion of the field of view (e.g., by rendering expression levels of a biomarker, analysis results, visualization types).

FIG. 4 illustrates display of two exemplary image sub-panels 218, 220 in the main image panel 202, where the sub-panels are organized horizontally relative to each other in order to display left and right portions of the field of view. Any suitable pattern is possible for arranging the image sub-panels, for example, vertical organization shown in FIG. 5 (in which top and bottom sub-panels 218', 220' display top and bottom portions of a field of view), grid-like, and the like. In FIG. 4, the first sub-panel 218 displays a left portion of the field of view according to a first display type (a VDAB visualization type for the CD30 biomarker), and the second sub-panel 220 displays a right portion of the field of view according to a second display type (a VHE image).

Figure 6:
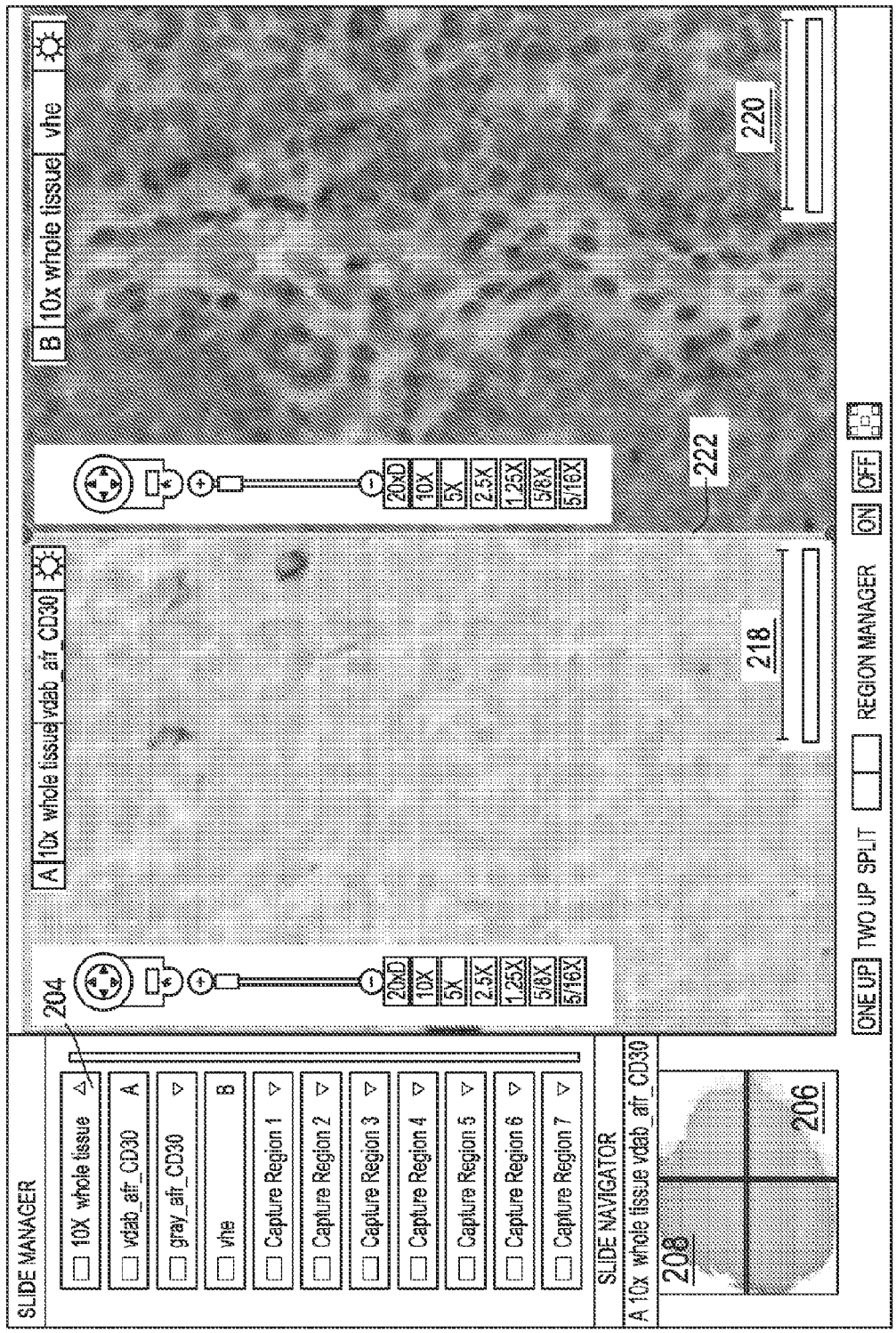
FIG. 6 illustrates the user interface of FIG. 4, displaying an image in which a left sub-panel shows expression levels of a biomarker in a left portion of the field of view and a right sub-panel shows morphological features in a right portion of the field of view.

Each sub-panel may have a corresponding zoom input tool 210', 210" for increasing or decreasing the magnification level, and a pan input tool 214', 214" for panning to a different field of view. Upon zooming in or out, the new zoomed-in field of view may be displayed on the image panel 202 such that contiguous portions of the field of view are represented seamlessly in the sub-panels. For example, FIG. 6 shows a zoomed-in display in the image sub-panels 218, 220 (compared to the zoom level of FIG. 4), in which the sub-panels are configured to show contiguous portions of the new zoomed-in field of view. FIG. 6 illustrates an exemplary user interface displaying an image in which the left sub-panel shows expression levels of a biomarker in a left portion of the field of view and the right sub-panel shows morphological features in a right portion of the field of view. In some embodiments, zooming in or out to update the resolution of one image sub-panel may automatically update all sub-panels so that they display at the same scale or resolution. In an exemplary embodiment, a computing device running the user interface may determine that new zoom level requires image data from a different resolution level in a tiled multi-resolution data structure, and may retrieve one or more tiles of image data from the resolution level.

In an embodiment, the sub-panels may be maintained at the same image scale. In other embodiments, the sub-panels may be configured at different scales.

Each sub-panel 218, 220 may also include a pan input tool 212', 212". In addition, a user may use the field of view selection component 208 in the image navigation component 206 to pan to a different field of view. Upon panning to a new field of field, the new field of view may be displayed on the image panel 202 such that contiguous portions of the field of view are represented seamlessly in the sub-panels. For example, FIG. 6 shows a different field of view displayed in the image sub-panels 218, 220 (compared to the field of view shown in FIG. 4), in which the sub-panels are configured to show contiguous portions of the new field of view. In some embodiments, upon panning in one image sub-panel, all sub-panels may be automatically updated to pan accordingly. In an exemplary embodiment, a computing device running the user interface may determine that a different set of tiles of image data is required to represent the new field of view, and may retrieve the set of tiles from a tiled multi-resolution data structure.

Figure 7:
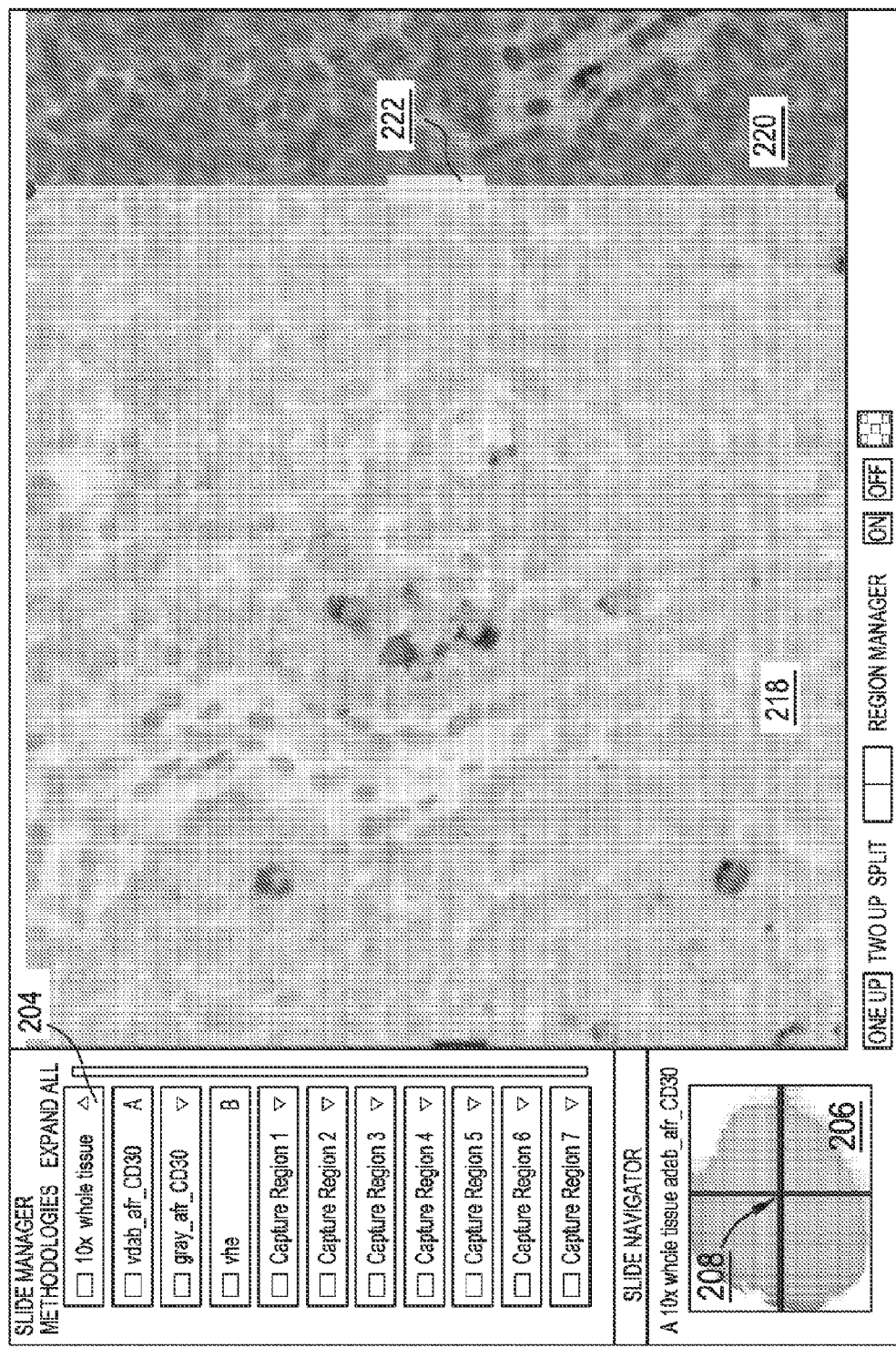
FIG. 7 illustrates the user interface of FIG. 6, displaying a slider component that may be used to adjust the sizes of two or more image sub-panels.

In exemplary embodiments, as illustrated in FIGS. 4-7, the main image panel 202 may include one or more interactive slider components 222 disposed at a boundary between two or more image sub-panels 218, 220. A slider component 222 may be used to reconfigure the relative portions of the image panel 202 occupied by the different sub-panels 218, 220. For example, the slider component 222 may be dragged across the image panel 202 to reduce the size of one or more sub-panels and increase the size of one or more other sub-panels displayed. This may create the visual effect of dragging one image sub-panel over another like a window shade. FIG. 7 illustrates an example in which the slider component 222 is dragged to the right to reduce the size of the right sub-panel 220 and increase the size of the left sub-panel 218. The same field of view is displayed by the collection of sub-panels 218, 220 so that the sub-panels display contiguous portions of the field of view. In this example, the left sub-panel 218 is updated to show a larger portion of the same field of view (according to the display type associated with the left sub-panel) and the right sub-panel 220 is updated to show a smaller portion of the same field of view (according to the display type associated with the right sub-panel).

In some exemplary embodiments, the user interface 200 may include a morphology selection component for enabling a user to select one or more morphological features for display in any of the image sub-panels. Upon receipt of user input selecting one or more morphological features, these features may be represented in the relevant image sub-panels, for example, as an image overlay. Exemplary morphological features may include, but are not limited to, a cell, a collection of cells, a sub-cellular component (e.g., nucleus, cytoplasm, membrane), and the like.

In some embodiments, the user interface may enable a user to overlay image analysis results (e.g., results of segmentation analysis) on any of the image sub-panels.

Figure 8:
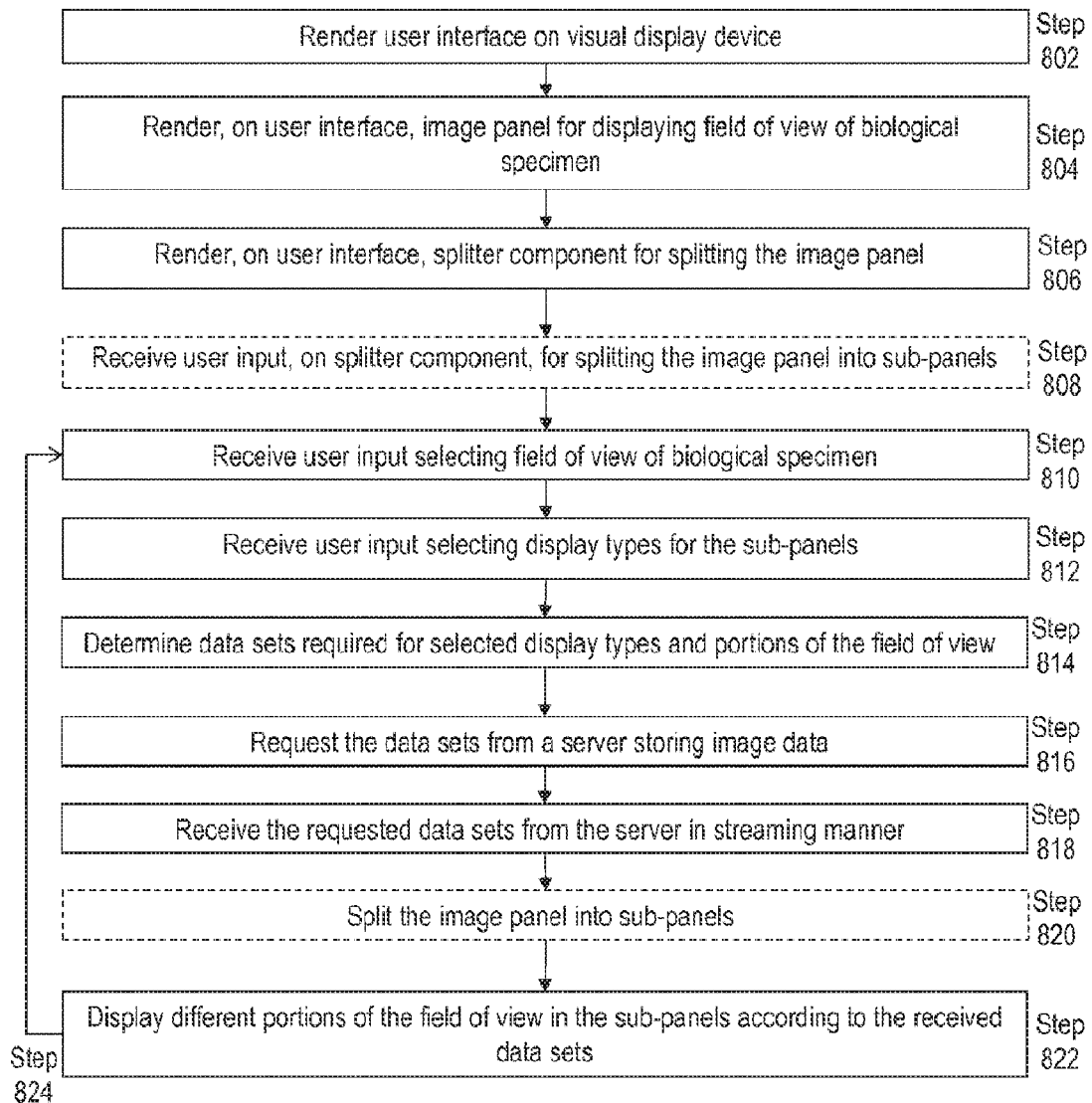
FIG. 8 is a flowchart of an exemplary computer-implemented method for providing a split screen display of a field of view of a biological specimen.

FIG. 8 is a flowchart of an exemplary computer-implemented method for providing a split screen display of a field of view of a biological specimen. In step 802, a graphical user interface may be rendered on a visual display device. In step 804, an image panel may be rendered on the user interface for displaying a field of view of a biological specimen. In step 806, a splitter component may be rendered on the user interface to enable a user to split the image panel into two or more image sub-panels.

In step 808, user input may be received on the splitter component for splitting the image panel into two or more image sub-panels, where each sub-panel is configured for displaying a different portion of the field of view. The user input may be received at the graphical user interface or in a different user interface or command prompt. In some exemplary embodiments, the user input may specify the organization of the image sub-panels on the user interface. Alternatively, exemplary embodiments may determine whether and how to split the image panel based on stored settings.

In step 810, user input may be received selecting a field of view from an image of a biological specimen. In step 812, user input may be received selecting two or more display types for rendering portions of the field of view in the different image sub-panels.

In one example, user input may specify that a first image sub-panel should display expression levels of a first biomarker in a first portion of the field of view, and a second image sub-panel should display expression levels of a second biomarker in a second portion of the field of view. In another example, user input may specify that a first image sub-panel should display expression levels of a biomarker in a first portion of the field of view, and a second image sub-panel should display one or more morphological features in a second portion of the field of view. In another example, user input may specify that a first image sub-panel should display a first set of one or more morphological features in a first portion of the field of view, and a second image sub-panel should display one or more morphological features in a second portion of the field of view.

In step 814, for each sub-panel, exemplary embodiments may determine a data set that selectively corresponds to image data of the selected display type for the portion of the field of view to be displayed in the sub-panel.

In an exemplary embodiment, in step 814, a computing device providing the user interface may access image data from a remote server storing image data on biological specimens in tiled multi-resolution data structures. In this case, the computing device running the user interface may determine the tiles of data that are selectively required for its purposes, and may request only those selective tiles from the server. That is, image data on the entire biological specimen may not be requested or preloaded into the user interface in some embodiments; but, rather, only those sets of image data that are required at a given time may be requested from the server. As one example, when the zoom level of an image displayed in the GUI 200 is adjusted, the computing device may be programmed to request tile images from the appropriate pyramid level. As another example, when performing a pan operation for an image displayed in the GUI 200, the computing device may be programmed to request tile images for the new portions of the image to be displayed within the main panel and/or sub-panel(s). Using this approach minimizes server overhead in servicing the requests and reduces the amount of image data that needs to be transferred to the computing device for its user interface, thereby making the user interface rapid and efficient in responding to user interactions and requests. In response to the request for data, the server may access the requested tiles of data and, in some cases, perform analysis or validation of the data. The server may then transfer the tiles of data to the computing device in a streaming manner.

Figure 9:
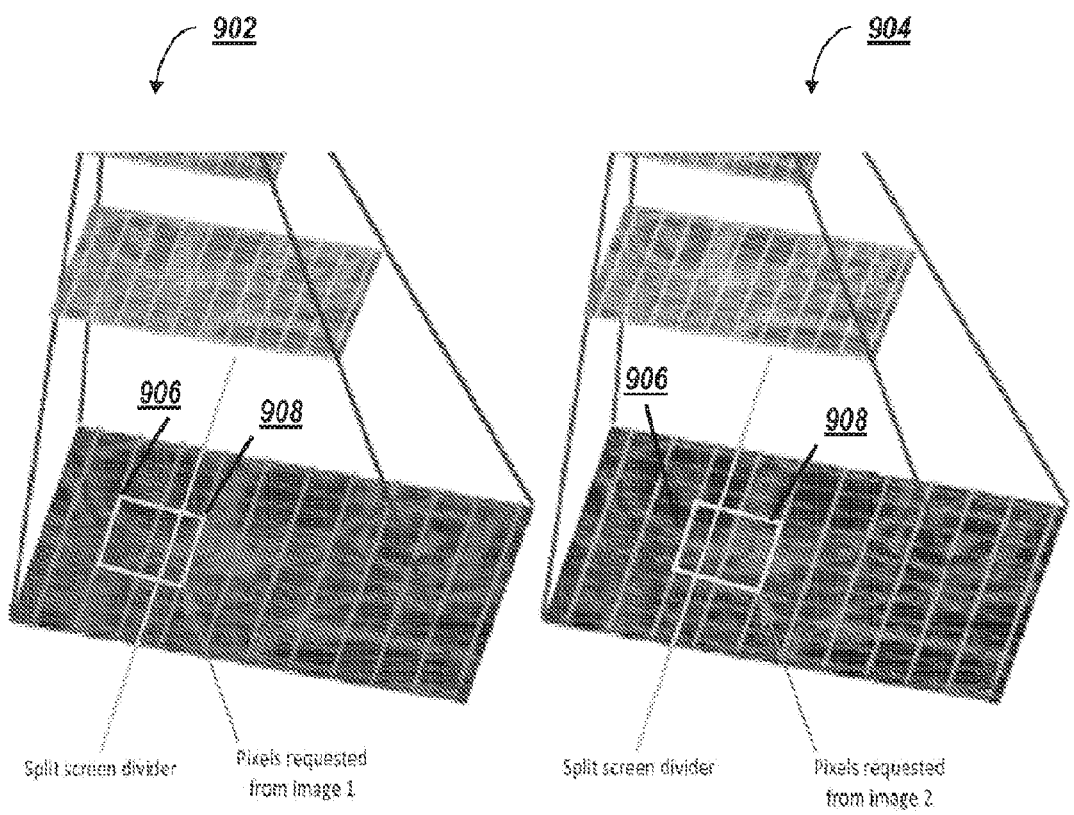
FIGS. 9A and 9B illustrate exemplary data structures for storing image data required for displaying the image sub-panels of FIG. 4.

Separate sets of pixel data are retrieved from the remote server for the different image sub-panels. For each image sub-panel, a computing device providing the user interface may determine an identification of the biological specimen and an identification of one or more biomarkers and/or morphological features to be displayed in the sub-panel. Based on the identification, the computing device may be programmed to determine the appropriate data structure to access. For example, if a first image sub-panel displays a biological specimen from a particular slide-spot including expression levels of a first biomarker, the computing device may be able to identify a first data structure 902 illustrated in FIG. 9A that is specific to both the first biomarker and the particular slide-spot. Similarly, if a second image sub-panel displays a biological specimen from the slide-spot including expression levels of a second biomarker, the computing device may be able to identify a second data structure 904 illustrated in FIG. 9B that is specific to both the second biomarker and the slide-spot.

For each image sub-panel, the computing device may be programmed to determine which resolution layer in a tiled multi-resolution data structure should be accessed for image data. To this end, the computing device may determine the resolution at which the image sub-panels are to display the field of view or are requested to display the field of view (e.g., by reviewing the zoom settings and/or panel sizes). Based on this determination, the computing device may access an image in the data structure that is at an appropriate resolution layer. For example, as illustrated in FIG. 6, if the image sub-panels show a zoomed-in version of the field of view, then the computing device may determine that an image at the highest resolution layer of a data structure should be accessed.

For each image sub-panel, the computing device may be programmed to determine which tiles of image data in the image should be accessed. To this end, the computing device may analyze the field of view of the biological tissue that is to be displayed in the main image panel, and the portion of the field of view that is to be displayed in the image sub-panel. Based on the analysis, the computing device may determine the portions or tiles of image data to access. The relevant tiles of image data thereby correspond to the pixel data necessary to display an image sub-panel, such that the collection of image sub-panels have correctly aligned boundaries so that they collectively display a seamless and contiguous field of view in the main image panel.

FIGS. 9A and 9B illustrate a representation of data structures 902, 904 corresponding to two image sub-panels. In this example, the first sub-panel is generated using data contained in the first data structure 902, and the second sub-panel is generated using data contained in the second data structure 904. The computing device may be programmed to determine that the first sub-panel corresponds to a first set of tiles 906 containing pixel image data in the first data structure 902, and that the second sub-panel corresponds to a second set of tiles 908 containing pixel image data in the second data structure 904. The computing device may be programmed to create a request to selectively retrieve the first set of tiles 906 from the first data structure 902 and the second set of tiles 908 from the second data structure 904. The request may be transmitted to the remote server storing the data structures. In response, the server may easily and rapidly access the requested tiles and transmit them to the computing device. In other embodiments, a different computing device than the computing device providing a user interface may perform the determination step 814.

In step 816, exemplary embodiments may request the server storing image data for the selective data sets determined for the different image sub-panels in step 814. In step 818, exemplary embodiments may receive the requested data sets in a streaming manner from the server based on the request. In an exemplary embodiment, the data sets may be received in real time as the user interacts with the user interface or may, alternatively, be received after a time lag after the user interacts with the user interface.

In step 820, exemplary embodiments may split the image panel into a plurality of image sub-panels based on user input from step 812. Alternatively, the image panel may be pre-loaded with the image sub-panels.

In step 822, exemplary embodiments may display different portions of the selected field of view in the different image sub-panels based on the data received from the server, so that the collection of sub-panels displays the overall field of view. Exemplary embodiments may align or register the boundaries of the sub-panels to form the split screen display.

Exemplary embodiments allow a user to smoothly browse different fields of view of the biological specimen, while maintaining the sub-panel configuration in the user interface. As the user changes the field of view, the new field of view is displayed in the image panel so that contiguous portions of the new field of view are automatically displayed in the corresponding image sub-panels. In step 824, user input may be received to change the field of view of the biological specimen displayed in the image panel. Steps 810-822 may be repeated as a result.

One of ordinary skill in the art will recognize that the exemplary method of FIG. 8 may include more or fewer steps than those illustrated in the exemplary flowchart, and that the steps in the exemplary flowchart may be performed in a different order than shown.

Exemplary Selection and Display of Biomarker Expression in a Biological Specimen In some exemplary embodiments, a main image panel may be provided for displaying a field of view corresponding to an image, or a portion of an image, of a biological specimen, and a biomarker panel may be provided for displaying thumbnail images of a region of the field of view for simultaneously viewing different aspects of the region (e.g., expression levels of different biomarkers in the region). This feature of the present invention may colloquially be referred to as a 'digital prism', as the thumbnails may desirably depict constituent features of the image in the main display. Upon selection or update of the selected region of the field of view, the thumbnail images may be accordingly updated automatically to display the newly selected region. The main image panel desirably includes an image of a biological specimen and may include an interest region selection component (e.g. a reticle or any other suitable component) for delineating the region within the field of view displayed in the main image panel. In an exemplary embodiment, the interest region selection component may be overlaid over a portion of the field of view displayed in the main image panel, and may be used by a user to select or update the region of the field of view displayed in the biomarker panel.

The biomarker panel may be configured to include a set of one or more thumbnail images of the region of the field of view delineated within the interest region selection component. The thumbnail images may represent different aspects or display types of the same region, for example, expression of different biomarkers, expression of morphological units, analysis results, combinations of the above display types, and the like. For example, each thumbnail image may display expression levels of a different biomarker or combination of biomarkers in the respective region of the field of view. In exemplary embodiments, if the main image panel displays expression levels of one or more biomarkers, the biomarker panel may provide an indication of which thumbnail image corresponds to the biomarker displayed in the main image panel. A thumbnail image may be selected by a user to update the main image panel so that it displays the biomarker of the selected thumbnail image.

The thumbnail images enable viewing of different aspects of a region of a field of view in a simple and organized manner in the biomarker panel. In some exemplary embodiments, the thumbnail images may be smaller in size and scale than the main image panel, and therefore do not result in a user-unfriendly, busy interface. Furthermore, the display in the thumbnail images, although small in some embodiments, is based on a smaller region than the entire field of view and, as such, can still be displayed at a sufficiently high resolution for easy viewing and interpretation of the thumbnail images.

The interest region selection component also enables automatic updating of the thumbnail images to selectively display any region of interest in the field of view rendered in the main image panel. A user may easily and rapidly focus on a region of interest in the main image panel, for example, a region including one or more morphological features of interest (e.g., a cell, a collection of cells, a sub-cellular component). This capability transforms the thumbnails from a simple navigation aid to a tool that can be used to rapidly interrogate biomarker expression patterns.

Certain clinical applications using exemplary user interfaces require assessment of more than one biomarker in a rapid fashion. This assessment is accelerated by the biomarker panel that provides rapid and intuitive navigation between biomarkers based on thumbnail images of their full visualizations. The assessment is also accelerated by displaying targeted information in the thumbnail images. For example, the thumbnail images become even more informative as they may be updated to represent exact regions of interest in a field of view of a biological specimen. Assessment of Hodgkin's lymphoma—in which only the biomarker expression of Reed Sternberg cells is diagnostically significant—is an exemplary application in which the capabilities of exemplary embodiments are particularly useful.

An exemplary biomarker panel may be configured to include any suitable number of thumbnail images. Exemplary numbers of thumbnail images provided in a biomarker panel may include, but are not limited to, 1, 2, 3, 4, 5, 6, 7, 8, 9, 10, 11, 12, 13, 14, 15, and the like.

The biomarker panel may be loaded as including a set of thumbnail images based on stored default settings on one or more biomarkers that are to be displayed in the biomarker panel. Alternatively, the biomarker panel may be provided with a set of thumbnail images upon receiving user input on one or more biomarkers that are to be displayed in the biomarker panel.

Two or more exemplary thumbnail images may be organized in a biomarker panel with respect to one another in any suitable pattern or manner, for example, horizontally relative to one or another, vertically relative to one another, or in a grid organization. The thumbnail images may be loaded into the biomarker panel in an organization specified in a stored default setting or a user preference. Alternatively, a user may specify how the thumbnail images are to be organized in the biomarker panel. In addition, during use, a user may reorganize the thumbnail images in the biomarker panel (e.g., by dragging and dropping using a mouse cursor), for example, based on a clinical relevance of a biomarker. A thumbnail image of a biomarker that is very relevant in diagnosing a clinical condition in the biological specimen may, for example, by placed first in the order of the thumbnail images. The ordering or reordering of the thumbnail images may be saved as a setting so that, when the thumbnail images are reloaded for the biological specimen, the thumbnail images are organized as specified in the saved setting.

Figure 10:
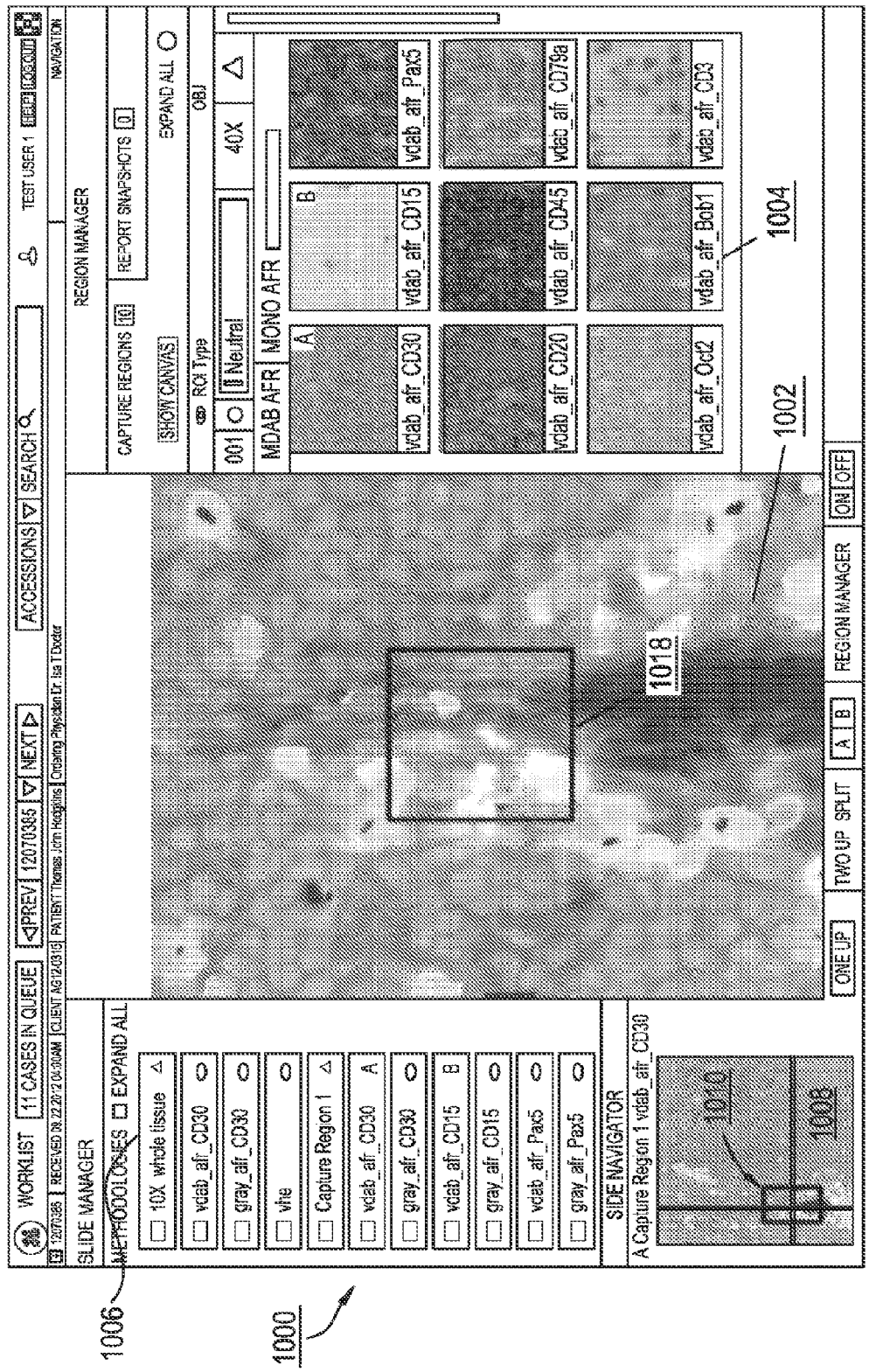
FIG. 10 illustrates a user interface for displaying a main image panel and a biomarker panel including one or more thumbnail images of biomarker expression data.

FIGS. 10-14 illustrate an exemplary graphical user interface (GUI) 1000 that may be used to enable selection and display of biomarker expression in a biological specimen, although other suitable user interfaces may be used. FIG. 10 illustrates the GUI 1000 including a main image panel 1002 for displaying a field of view of a biological specimen, and a biomarker panel 1004 for displaying thumbnail images of biomarker expression associated with a region in the field of view of the biological specimen. The present invention contemplates that the field of view represented in main image panel 1002 typically corresponds to a portion of the entire image of a biological specimen.

A user may select a desired biological specimen (e.g., a slide/spot) for display in the main image panel 1002. The biological specimen may be selected using the GUI 1000, a command panel, or any other suitable means. A selected biological specimen may have corresponding stored image data that may be displayed in the GUI 1000. Exemplary image data may include, but is not limited to, expression data on one or more biomarkers, display data on one or more morphological features, results of one or more image analysis techniques, and the like. A display type selection component 1006 may be used by a user to indicate one or more display types available for display in the main image panel 1002. Exemplary display types used in exemplary embodiments may include, but are not limited to, expression of one or more biomarkers, display of one or more morphological features, display of one or more analysis results, display according to one or more visualization types (e.g., binary heat-map, discrete heat-map, continuous heat-map, intensities of grey or color pixels, or color blend of two or more biomarker expressions), combinations of any of the above types, and the like.

Figure 11:
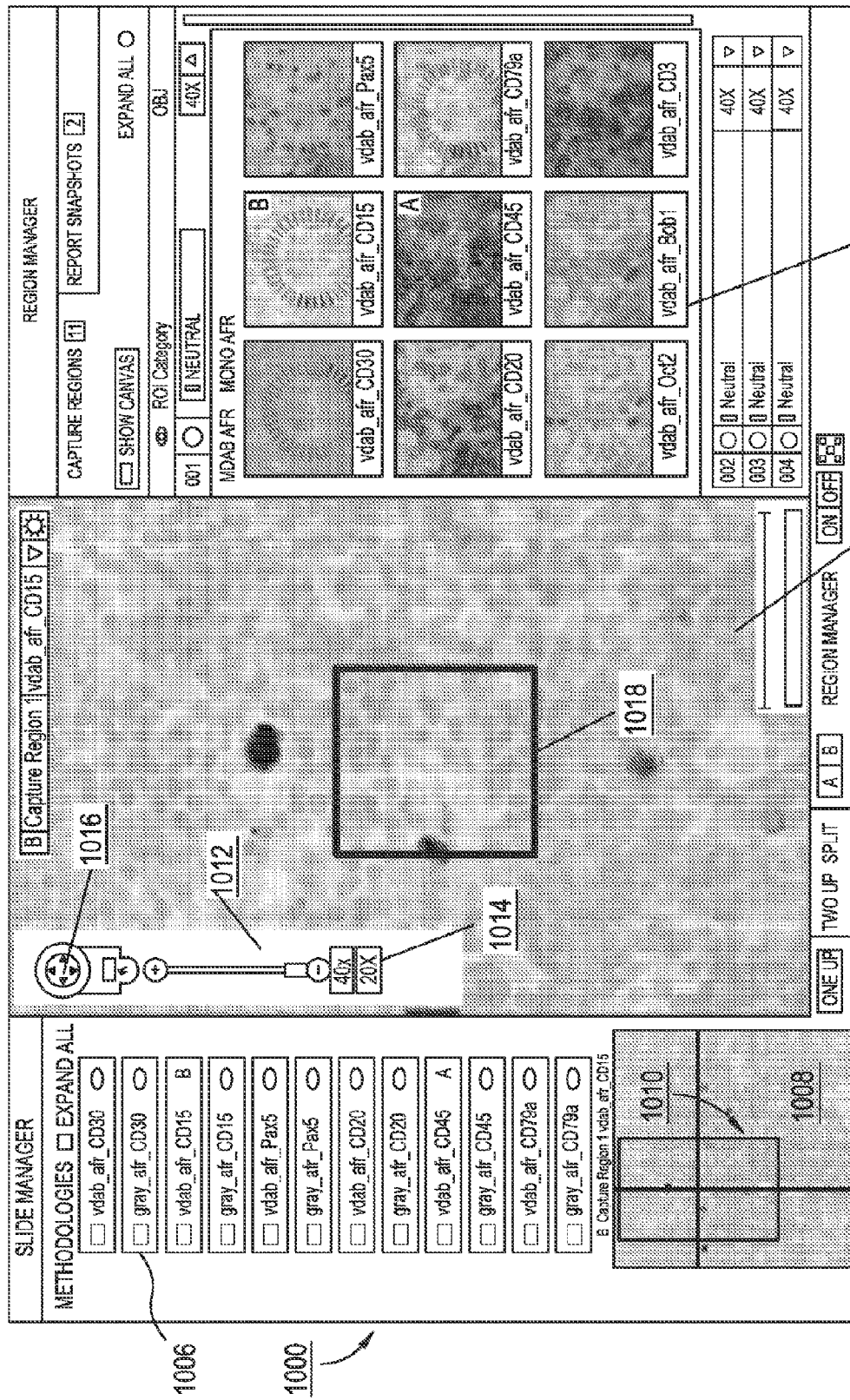
FIG. 11 illustrates the user interface of FIG. 10, displaying a different field of view at a different zoom level in the main image panel.

Upon receiving a user selection of a display type for the selected biological specimen (e.g., by clicking the selection and dragging it onto the main image panel 1002), the main image panel may render the field of view displayed according to the selected display type. FIG. 11 illustrates display of a field of view of a biological specimen in the main image panel 1002, representing a VDAB visualization type for the CD30 biomarker.

In some exemplary embodiments, the user interface 1000 may include a morphology selection component for enabling a user to select one or more morphological features for display in the main image panel 1002. Upon receipt of user input selecting one or more morphological features, these features may be represented in the main image panel 1002, for example, as an image overlay. Exemplary morphological features may include, but are not limited to, a cell, a collection of cells, a sub-cellular component (e.g., nucleus, cytoplasm, membrane), and the like.

In some embodiments, the user interface may enable a user to overlay image analysis results (e.g., results of segmentation analysis) on the main image panel 1002.

Upon display of a field of view in the main image panel 1002, the GUI 1000 may be updated to include an image navigation component 1008 that displays the overall biological specimen of which the field of view displayed in the main image panel 1002 is a part. The image navigation component 1008 displays the biological specimen in accordance with the display type selected by the user.

The image navigation component 1008 may include a field of view selection component 1010 (e.g. a reticle or any other suitable component) for delineating the field of view within the overall display of the biological specimen. This allows the user to generally locate where the field of view (displayed in the main image panel 1002) can be found in the overall biological specimen (displayed in the image navigation component 1008). The field of view selection component 1010 may be an interaction component for enabling a user to select any field of view in the biological specimen displayed in the image navigation component 1008 so that the main image panel 1002 is updated to display the selected field of view. Similarly, a user may use the field of view selection component 1010 to browse different fields of view in a continual and smooth manner. The user may select the field of view selection component 1010 (e.g., by clicking on it with a mouse cursor) and drag and drop the field of view selection component 1010 on a new different field of view. In an exemplary embodiment, upon dropping the field of view selection component 1010 by releasing the cursor, the main image panel 1002 may be automatically updated to display the new field of view. In an exemplary embodiment, the main image panel 1002 may also be automatically updated while the field of view selection component 1010 is dragged by the user. In some embodiments, this update may be performed in real time as the user interacts with the user interface or may, alternatively, be performed after a time lag after the user selects a new location for the field of view.

In some embodiments, the image navigation component 1008 is smaller than the main image panel 1002 and provides a lower resolution display of the biological specimen. In other embodiments, the image navigation component 1008 may be the same size as or larger than the main image panel 1002.

In an exemplary embodiment illustrated in FIG. 11, the main image panel 1002 may include a zoom input tool 1012 for allowing a user to input a particular level of zoom or a relative level of zoom (e.g., using a zoom slider and/or zoom buttons). The current relative zoom level may be indicated on the image panel in a zoom indicator 1014. In some cases, the zoom level may be reset to a default level by the user or automatically by the system. In some exemplary embodiments, the user interface may allow zooming in and out using a pointing device directly on the image on the main image panel 1002, for example, by clicking the right button on a mouse. In some exemplary embodiments, the user interface may allow zooming in and out using keyboard shortcuts, for example, using a combination of the "Ctrl" key and the "+" key to zoom in and using a combination of the "Ctrl" key and the "−" key to zoom out. When the main image panel 1002 is updated according to a new zoom level, the field of view selection component 1010 in the image navigation component 1008 may be automatically updated to correctly delineate the corresponding updated field of view shown in the main image panel 1002. In an exemplary embodiment, a computing device running the user interface may determine that new zoom level requires image data from a different resolution level in a tiled multi-resolution data structure, and may retrieve one or more tiles of image data from the resolution level.

In an exemplary embodiment, the main image panel 1002 may include a pan input tool 1016 for panning to a new field of view in the biological specimen. The pan input tool 1016 may allow a user to input a particular level of panning in the biological specimen or a relative level of panning using a slider. In some cases, the pan settings may be reset to display the initially displayed field of view in the main image panel 1002. In some exemplary embodiments, the user interface may allow panning using a pointing device directly on the main image panel 1002, for example, by clicking the left button on a mouse over the image, dragging the cursor across the image and releasing it to display a new field of view. In one embodiment, the main image panel 1002 may be updated to display the new field of view upon release of the cursor. In an embodiment, the main image panel 1002 may also be updated in a real time manner as the user drags the cursor across the image or may, alternatively, be performed after a time lag after the user interacts with the user interface. In some exemplary embodiments, the user interface may allow panning using keyboard shortcuts. When the main image panel 1002 is updated to display a new field of view, the field of view selection component 1010 in the image navigation component 1008 may be automatically updated to correctly indicate the location of the new field of view in the specimen shown in the main image panel 1002.

The main image panel 1002 may include an interest region selection component 1018 (e.g. a reticle or any other suitable component) for delineating a region within the field of view displayed in the main image panel 1002. In an exemplary embodiment, the interest region selection component 1018 may be overlaid over a portion of the field of view displayed in the main image panel 1002. The biomarker panel 1004 may be configured to include a set of one or more thumbnail images of the portion of the field of view delineated within the interest region selection component 1018. The thumbnail images may represent different aspects or display types of the same region, for example, expression of different biomarkers, expression of morphological units, analysis results, combinations of the above display types, and the like. For example, each thumbnail image may display expression levels of a different biomarker or combination of biomarkers in the region of the field of view. The biomarker expression levels may be displayed in any suitable visualization type, for example, (e.g., binary heat-map, discrete heat-map, continuous heat-map, intensities of grey-scale values of grey or color pixels, color blend of two or more biomarker expressions).

In exemplary embodiments, if the main image panel 1002 displays expression levels of one or more biomarkers, the biomarker panel 1004 may provide an indication of which thumbnail image corresponds to the biomarker displayed in the main image panel.

In some exemplary embodiments, user input may be received selecting a thumbnail image corresponding to a particular biomarker. In response, exemplary embodiments may update the main image panel 1002 to display expression levels of the particular biomarker in the field of view of the biological specimen.

The thumbnail images enable viewing of different aspects of a region of a field of view in a simple and organized manner in the biomarker panel 1004. In some exemplary embodiments, the thumbnail images may be smaller in size and/or scale than the display in the main image panel 1002, and therefore do not result in a busy interface. In other embodiments, the thumbnail images may be equal to or greater in size and/or scale than the display in the main image panel 1002. The display in the thumbnail images, although small in some embodiments, is based on a smaller region than the entire field of view and, as such, the thumbnail images can still be displayed at a sufficient high resolution for easy viewing and interpretation of the thumbnail images.

The size and/or spatial dimensions of the biomarker panel 1004 may be set and/or scaled automatically based on the number and/or sizes of thumbnail images displayed. In some cases, the number of thumbnail images displayed may, in turn, be based on how many biomarkers are being viewed. In some embodiments, the user may be enabled to manually set or reset the size and/or dimensions of the biomarker panel 1004.

The size and/or spatial dimensions of the thumbnail images in the biomarker panel 1004 may be set and/or scaled automatically based on the number of thumbnail images displayed and/or the size of the biomarker panel 1004. In some embodiments, the user may be enabled to manually set or reset the size and/or dimensions of the thumbnail images.

Figure 14:
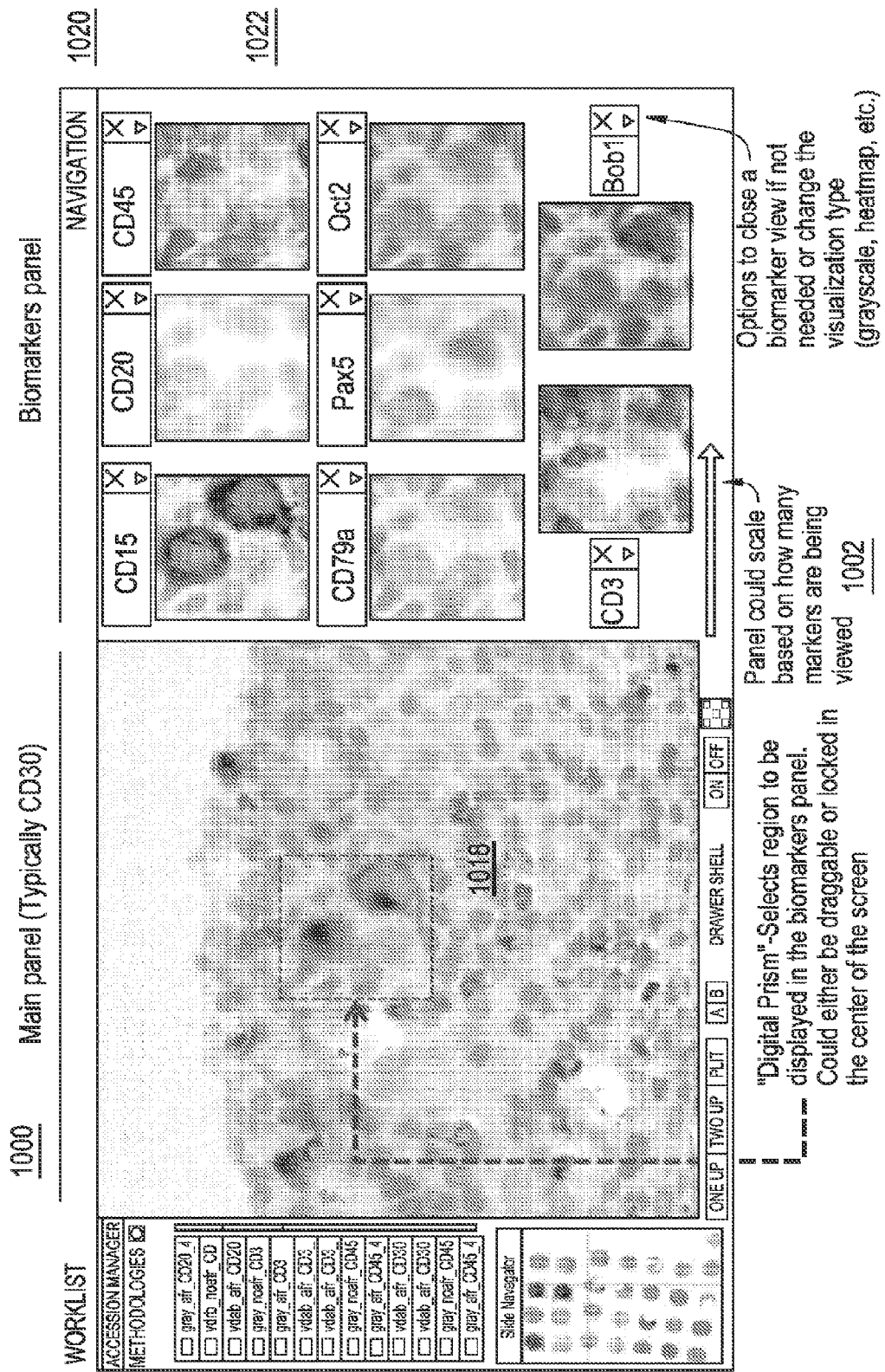
FIG. 14 illustrates a user interface for displaying a main image panel and a biomarker panel including one or more thumbnail images of biomarker expression data.

As illustrated in FIG. 14, each thumbnail image may have an associated tool 1020 for receiving user selection of a visualization type for the biomarker expression displayed in the thumbnail image. For example, a user may select a visualization type from a group including binary heat-map, discrete heat-map, continuous heat-map, intensities of grey-scale values of grey or color pixels, a simulated bright-field image, and the like.

As illustrated in FIG. 14, each thumbnail image may have an associated tool 1022 (e.g., a cross icon) for receiving user input on removing the thumbnail image from the biomarker panel 1004. Upon receiving user input for removing a thumbnail image, the biomarker panel 1004 may be automatically updated to remove the selected thumbnail image. Similarly, the biomarker panel 1004 may include a tool enabling a user to add new thumbnail images to the biomarker panel 1004. Upon receiving user input for adding a new thumbnail image, the biomarker panel 1004 may be automatically updated to add the selected thumbnail image.

User input may be received on the biomarker panel 1004 to change a scale or resolution of a first thumbnail image in the biomarker panel. The user input may be provided, for example, by dragging the boundaries to change the size of the first thumbnail image. In response to the user input, exemplary embodiments may update the biomarker panel to change the scale or resolution of the first thumbnail image. In an embodiment, the biomarker panel 1004 may also be updated to set the scale or resolution of the remaining thumbnail images to that of the first thumbnail image so that all thumbnail images have uniform resolution.

User input may be received on the interest region selection component 1018 to change a portion of the field of view displayed in a first thumbnail image in the biomarker panel 1004. The user input may be provided, for example, by dragging the boundaries to change the size of the interest region selection component 1018. In response to the user input, exemplary embodiments may update the biomarker panel 1004 to change the portion of the field of view displayed in the first thumbnail image. In an embodiment, the biomarker panel 1004 may also be updated so that all thumbnail images display the same region of the field of view.

The interest region selection component 1018 enables automatic updating of the thumbnail images to selectively display any region of interest in the field of view rendered in the main image panel 1002. A user may easily and rapidly focus on a region of interest in the main image panel 1002, for example, a region including one or more morphological features of interest (e.g., a cell, a collection of cells, a sub-cellular component). This capability transforms the thumbnails from a simple navigation aid to a tool that can be used to rapidly interrogate biomarker expression patterns. To implement this capability, the interest region selection component 1018 may be configured as an interaction component for enabling a user to select any region in the field of view displayed in the main image panel 1002. A user may use the interest region selection component 1018 to browse different regions in the field of view in a continual and smooth manner. The user may select the interest region selection component 1018 (e.g., by clicking on it with a mouse cursor) and drag and drop the interest region selection component 1018 on a different region of the field of view. In an exemplary embodiment, upon dropping the interest region selection component 1018 by releasing the cursor, the thumbnail images in the biomarker panel 1004 may be automatically updated to display the new region in the field of view. In an exemplary embodiment, the thumbnail images may also be automatically updated while the interest region selection component 1018 is dragged by the user. In some embodiments, this update may be performed in real time as the user interacts with the user interface or may, alternatively, be performed after a time lag after the user interacts with the user interface.

Alternatively, in order to browse different regions in the field of view, a user may select the image displayed in the main image panel 1002 (e.g., by clicking on the image with a mouse cursor) and drag and drop the image relative to the interest region selection component 1018 so that a different region in the image lies within the boundaries of the interest region selection component 1018. In an exemplary embodiment, upon dropping the image by releasing the cursor, the thumbnail images in the biomarker panel 1004 may be automatically updated to display the new region in the field of view that is delineated by the interest region selection component 1018. In an exemplary embodiment, the thumbnail images may also be automatically updated while the image is dragged by the user. In some embodiments, this update may be performed in real time as the user interacts with the user interface or may, alternatively, be performed after a time lag after the user interacts with the user interface.

Exemplary embodiments may enable a user to lock the interest region selection component 1018 at a fixed location relative to the image displayed in the main image panel 1002. A user may also be able to unlock the interest region selection component 1018 so that it is movable or draggable relative to the image displayed on the main image panel 1002.

Figure 12:
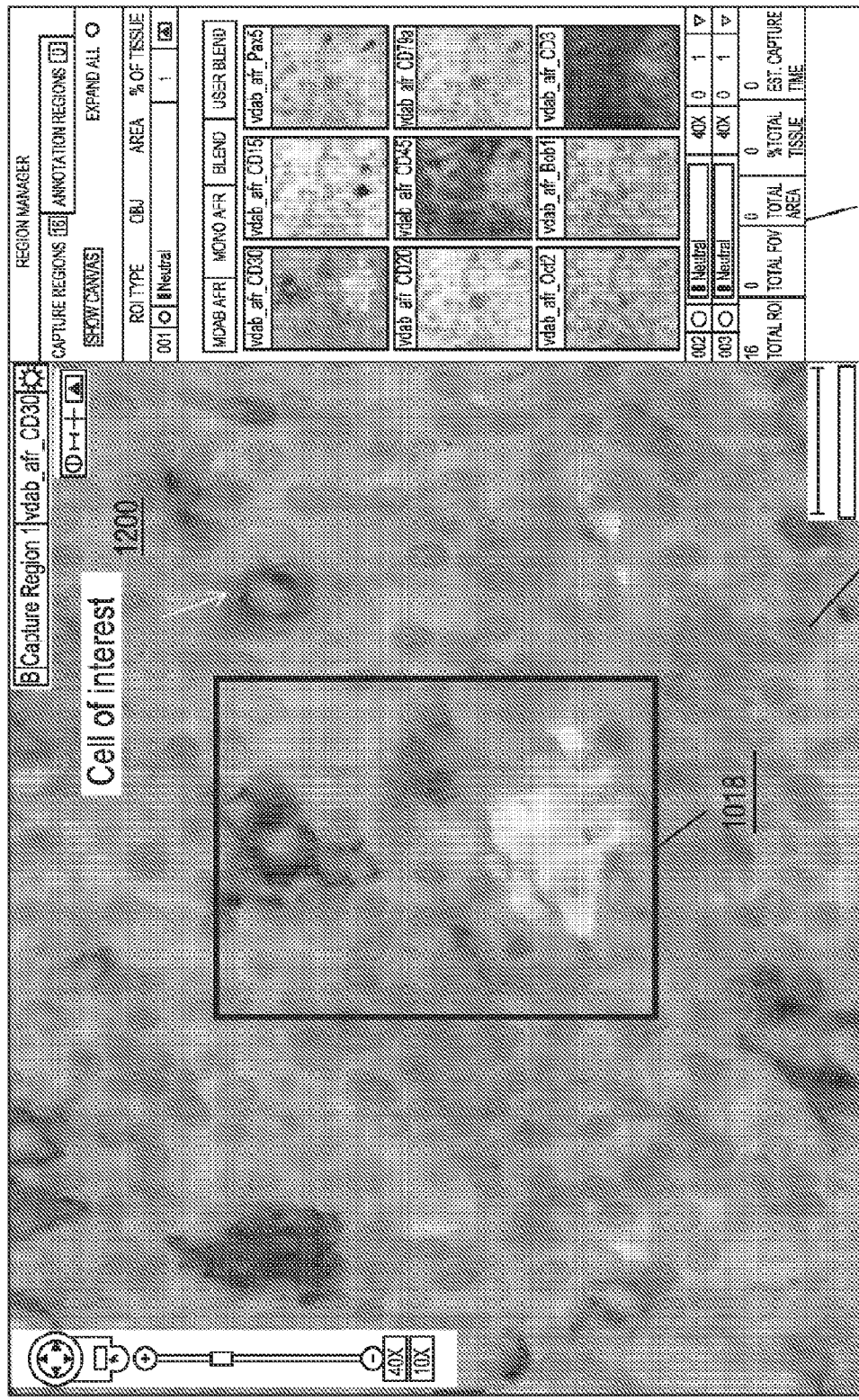
FIG. 12 illustrates the user interface of FIG. 10, in which a morphological feature of interest falls outside the boundaries of an interest region selection component in the main image panel.
Figure 13:
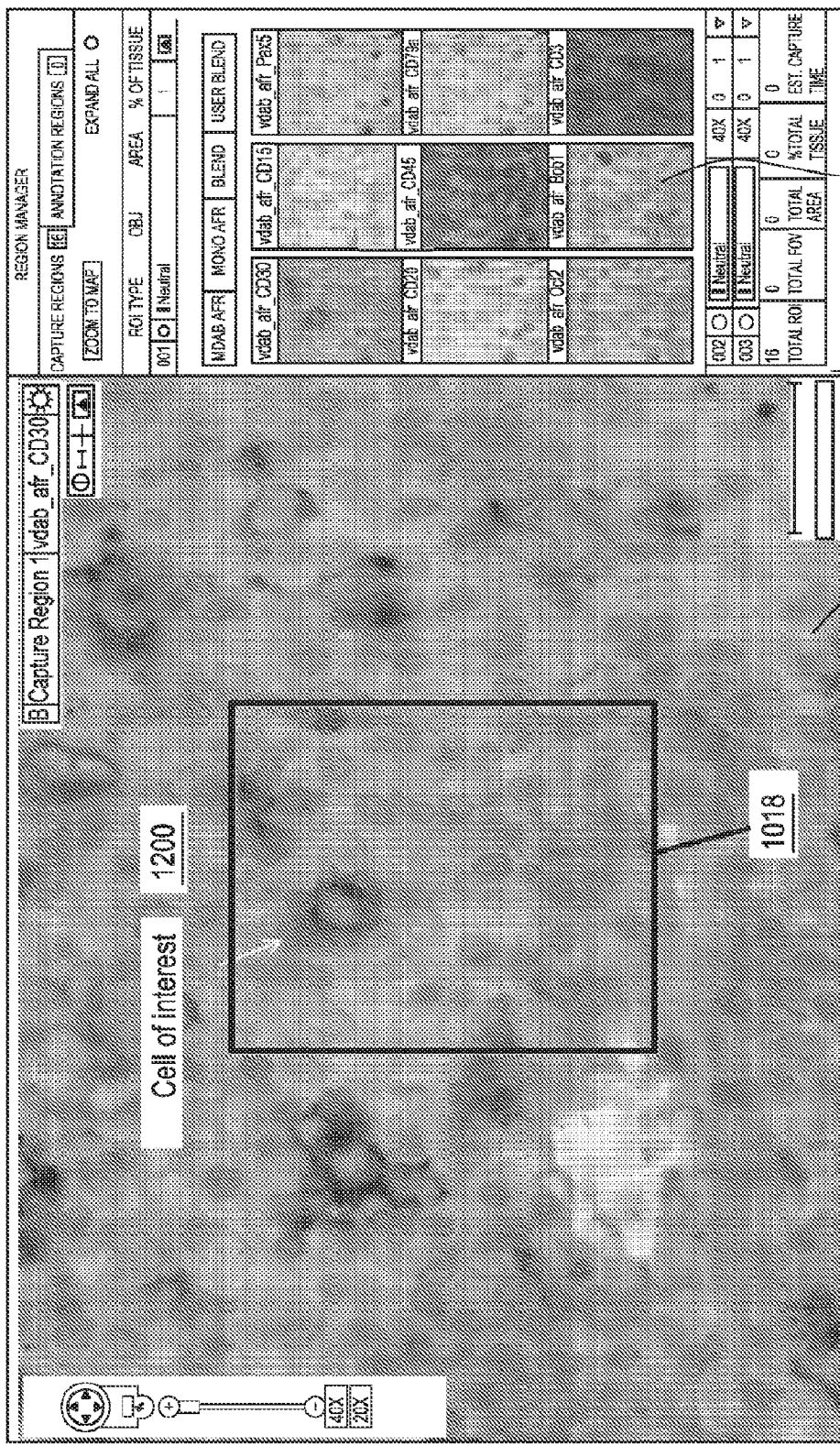
FIG. 13 illustrates the user interface of FIG. 12, in which the morphological feature of interest falls inside the boundaries of the interest region selection component in the main image panel.

FIGS. 12 and 13 illustrate an exemplary use of updating the biomarker panel 1004 to focus on a morphological feature of interest 1018 (e.g., a cell of interest). FIG. 12 illustrates the main image panel 1002 in which the morphological feature 1200 falls outside the boundaries of the interest region selection component 1018. As such, the biomarker panel 1004 illustrates a region of the field of view in the main image panel 1002 that does not include the morphological feature of interest 1200. FIG. 13 illustrates the main image panel 1002 in which the morphological feature of interest 1200 has been brought within the boundaries of the interest region selection component 1018 (either by adjusting the location of the interest region selection component 1018 relative to the image displayed in the main image panel 1002, and/or by adjusting the location of the image displayed in the main image panel 1002 relative to the interest region selection component 1018). In this case, the thumbnail images in the biomarker panel 1004 are automatically updated to display the portion of the field of view including the morphological feature 1200 that is now delineated by the interest region selection component 1018.

Figure 15:
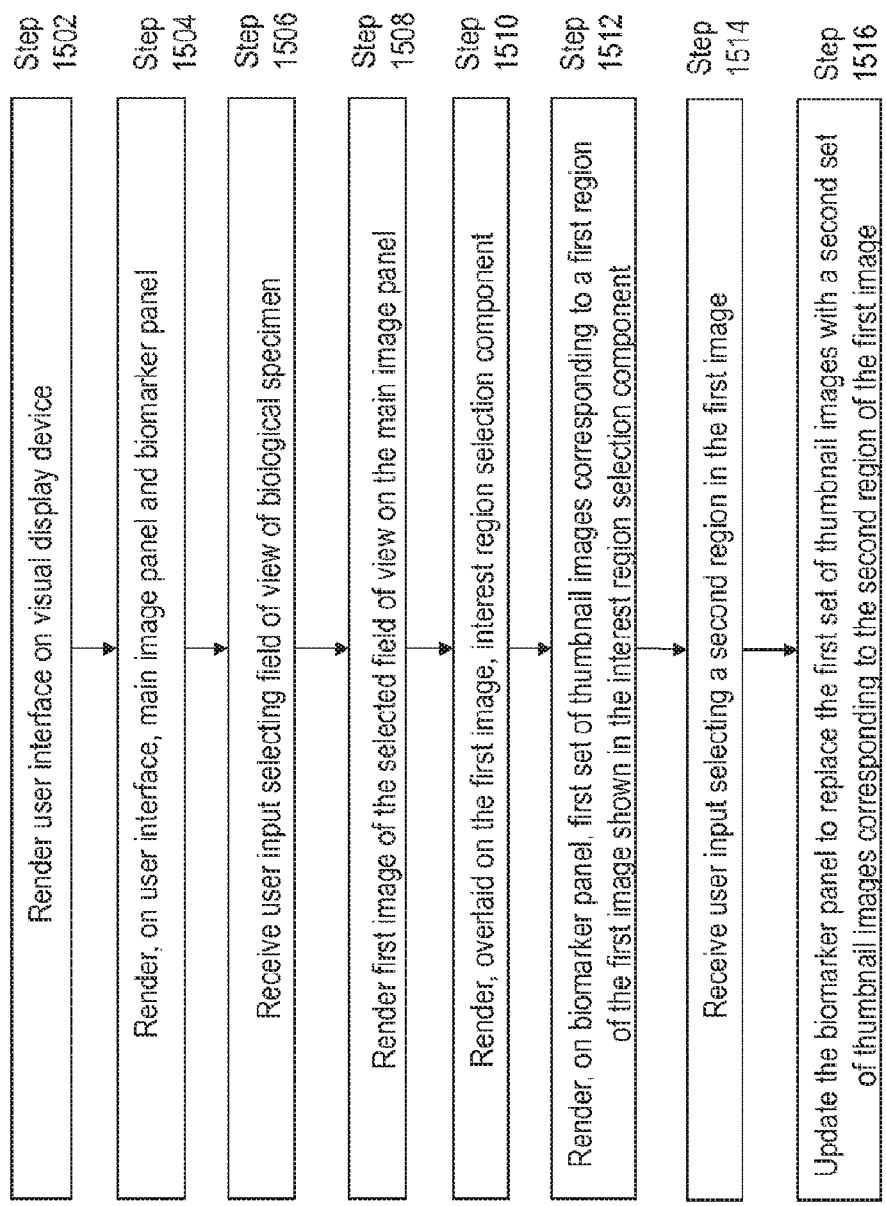
FIG. 15 is a flowchart of an exemplary computer-implemented method for displaying expression levels of one or more biomarkers in a field of view of a biological specimen.

FIG. 15 is a flowchart of an exemplary computer-implemented method for displaying expression levels of one or more biomarkers in a field of view corresponding to an image, or a portion of an image, of a biological specimen. In step 1502, a graphical user interface may be rendered on a visual display device. In step 1504, a main image panel and a biomarker panel may be rendered on the user interface.

In step 1506, user input may be received selecting a field of view of a biological specimen. In step 1508, a first image of the selected field of view may be rendered on the main image panel.

In step 1510, an interest region selection component may be overlaid on the first image in the main image panel. The interest region selection component may delineate a first region in the first image. In step 1512, a first set of thumbnail images may be rendered in the biomarker panel corresponding to the first region delineated in the interest region selection component. In an exemplary embodiment, the different thumbnail images in the first set of thumbnail images may display the same first region of the first image in different display types. For example, the different thumbnail images may display expression levels of different biomarkers in the region delineated in the interest region selection component.

In step 1514, user input may be received to select a different region in the first image for updating the thumbnail images. In an exemplary embodiment, the user input received may include the user selecting the interest region selection component (e.g., by clicking on its boundary using a mouse cursor), dragging the interest region selection component to a different location on the first image (e.g., by dragging the cursor), and releasing the interest region selection component at the new location on the first image (e.g., by releasing the cursor). Alternatively, the user input received may include the user selecting the first image on the main image panel (e.g., by clicking on the first image using a mouse cursor), dragging the first image relative to the interest region selection component (e.g., by dragging the cursor), and release the first image so that a new region of the first image is disposed under the interest region selection component (e.g., by releasing the cursor).

Exemplary embodiments may determine one or more data sets that selectively correspond to biomarker expression in the new region of the field of view delineated in the interest region selection component. Exemplary embodiments may request a server storing biomarker expression data for the selective data sets determined for the new region of the field of view. Exemplary embodiments may receive the requested data sets in a streaming manner from the server based on the request. In an exemplary embodiment, the data sets may be received in real time as the user interacts with the user interface or may, alternatively, be performed after a time lag after the user interacts with the user interface.

In an exemplary embodiment, a computing device providing the user interface may access image data from a remote server storing biomarker data on biological specimens in tiled multi-resolution data structures. In this case, the computing device running the user interface may determine the tiles of data that are selectively required for its purposes, and may request the selective tiles from the server. That is, image data on the entire biological specimen may not be requested or preloaded into the user interface in some embodiments; but, rather, only those sets of image data that are required at a given time for, for example the thumbnail images, may be requested from the server. As one example, when the zoom level of an image displayed in the GUI 200 is adjusted, the computing device can be programmed to request tile images from the appropriate pyramid level. As another example, when performing a pan operation for an image displayed in the GUI 200, the computing device can be programmed to request tile images for the new portions of the image to be displayed within the main panel and/or sub-panel(s). Using this approach minimizes server overhead in servicing the requests and reduces the amount of image data that needs to be transferred to the computing device for its user interface, thereby making the user interface rapid and efficient in responding to user interactions and requests. In response to the request for data, the server may access the requested tiles of data and, in some cases, perform analysis or validation of the data. The server may then transfer the tiles of data to the computing device in a streaming manner.

For each image thumbnail image, a computing device providing the user interface may determine an identification of the biological specimen and an identification of one or more biomarkers and/or morphological features displayed in the user interface. Based on the identification, the computing device may determine the appropriate data structure to access. For example, if a first thumbnail image displays a biological specimen from a particular slide-spot including expression levels of a first biomarker, the computing device may be able to identify a first data structure that is specific to both the first biomarker and the particular slide-spot. Similarly, if a second thumbnail image displays a biological specimen from the slide-spot including expression levels of a second biomarker, the computing device may be able to identify a second data structure that is specific to both the second biomarker and the slide-spot.

For each thumbnail image, the computing device may then determine which resolution layer in a tiled multi-resolution data structure should be accessed for image data. To this end, the computing device may determine the resolution at which the thumbnail image displays a region of the field of view or is requested to display a region of the field of view (e.g., by reviewing zoom levels in the thumbnail images and/or sizes of the thumbnail images and biomarker panel). Based on this determination, the computing device may access an image in the data structure that is at an appropriate resolution layer. For example, if the thumbnail images display a zoomed-in version of the region, then the computing device may determine that an image at the highest resolution layer of a data structure should be accessed.

For each thumbnail image, the computing device may then determine which tiles of image data in the selected data structure should be accessed. To this end, the computing device may analyze the field of view of the biological tissue that is displayed in the main image panel, and the region of the field of view that is to be displayed in the thumbnail images. Based on the analysis, the computing device may determine the portions or tiles of image data to access. The relevant tiles of image data thereby correspond to the pixel data necessary to display the thumbnail images.

In step 1516, in response to the user input and the received biomarker data, the biomarker panel may be updated to replace the first set of thumbnail images with a second set of thumbnail images that display the new region of the first image that is delineated in the interest region selection component.

In an exemplary embodiment, the first image on the main image panel may be updated to indicate or delineate the new region selected in step 1514, for example, by rendering the interest region selection component to delineate the new region in the first image.

One of ordinary skill in the art will recognize that the exemplary method of FIG. 15 may include more or fewer steps than those illustrated in the exemplary flowchart, and that the steps in the exemplary flowchart may be performed in a different order than shown.

Exemplary Split Screen Display and Biomarker Display for a Biological Specimen

Figure 16:
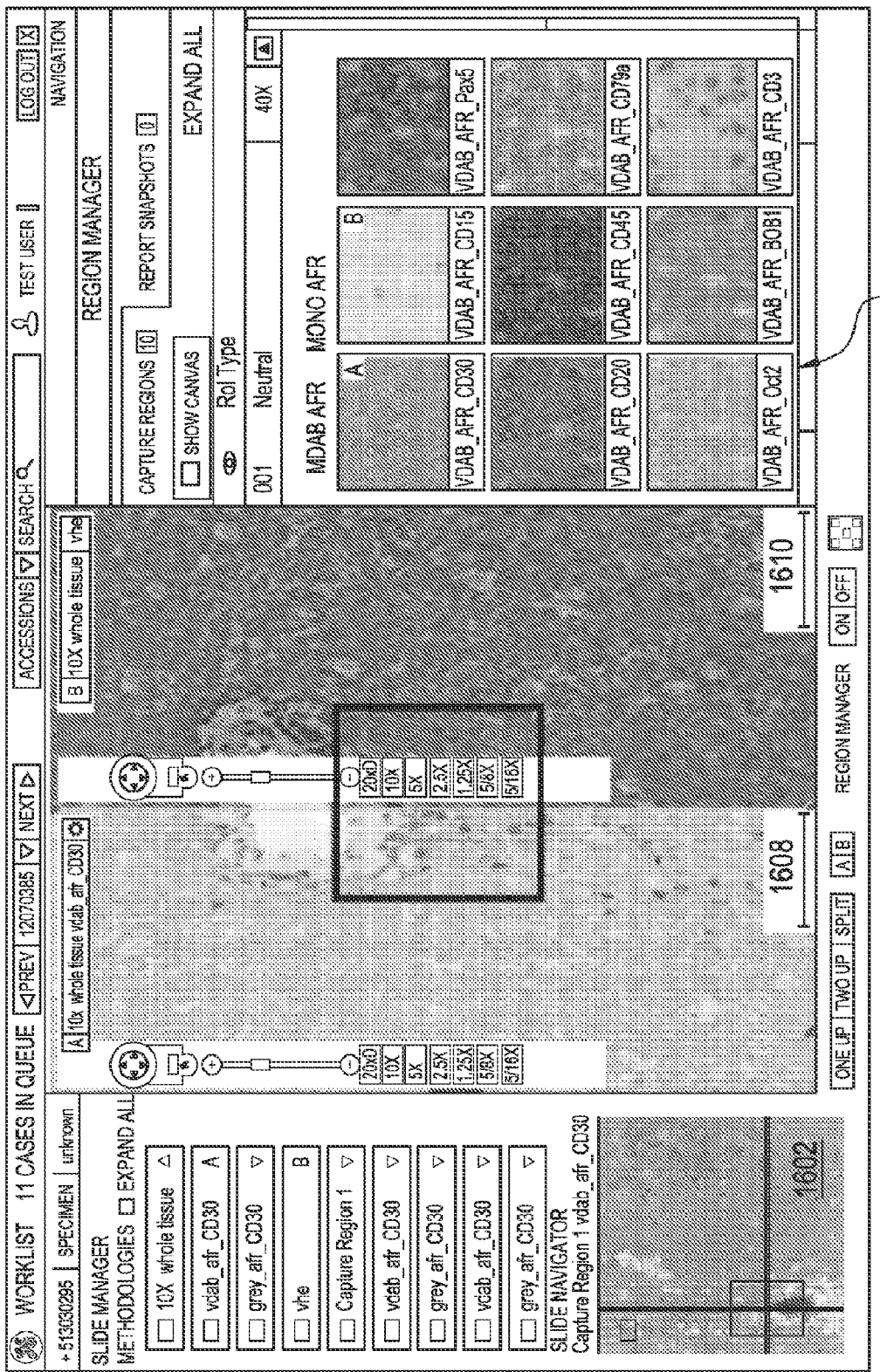
FIG. 16 illustrates a user interface for displaying a split screen view of a field of view of a biological specimen and a biomarker panel including one or more thumbnail images of biomarker expression data corresponding to a region of the field of view.

In some embodiments, a graphical user interface may be provided to combine the features of the interface illustrated in FIGS. 2-7 (to enable viewing of a split screen display of a field of view of a biological specimen) and the interface illustrated in FIGS. 10-14 (to enable viewing of expression levels of different biomarkers in a region of a field of view of a biological specimen). FIG. 16 is an exemplary graphical user interface 1600 that implements both capabilities. The graphical user interface 1600 includes, for example, an image navigation component 1602 for displaying an image, or a portion of an image, of a biological specimen, a main image panel 1604 for displaying a field of view in the image of the biological specimen, and a biomarker panel 1606 for displaying expression levels of one or more biomarkers within a region in the field of view displayed in the main image panel 1604. The main image panel 1604 may be split by a border into, or provided with, two exemplary image sub-panels 1608, 1610 for displaying two contiguous portions of the field of view. Exemplary features illustrated in FIG. 16 and their operations are described in more detail in connection with FIGS. 2-15.

Exemplary Network Architecture for Data Access

Figure 17:
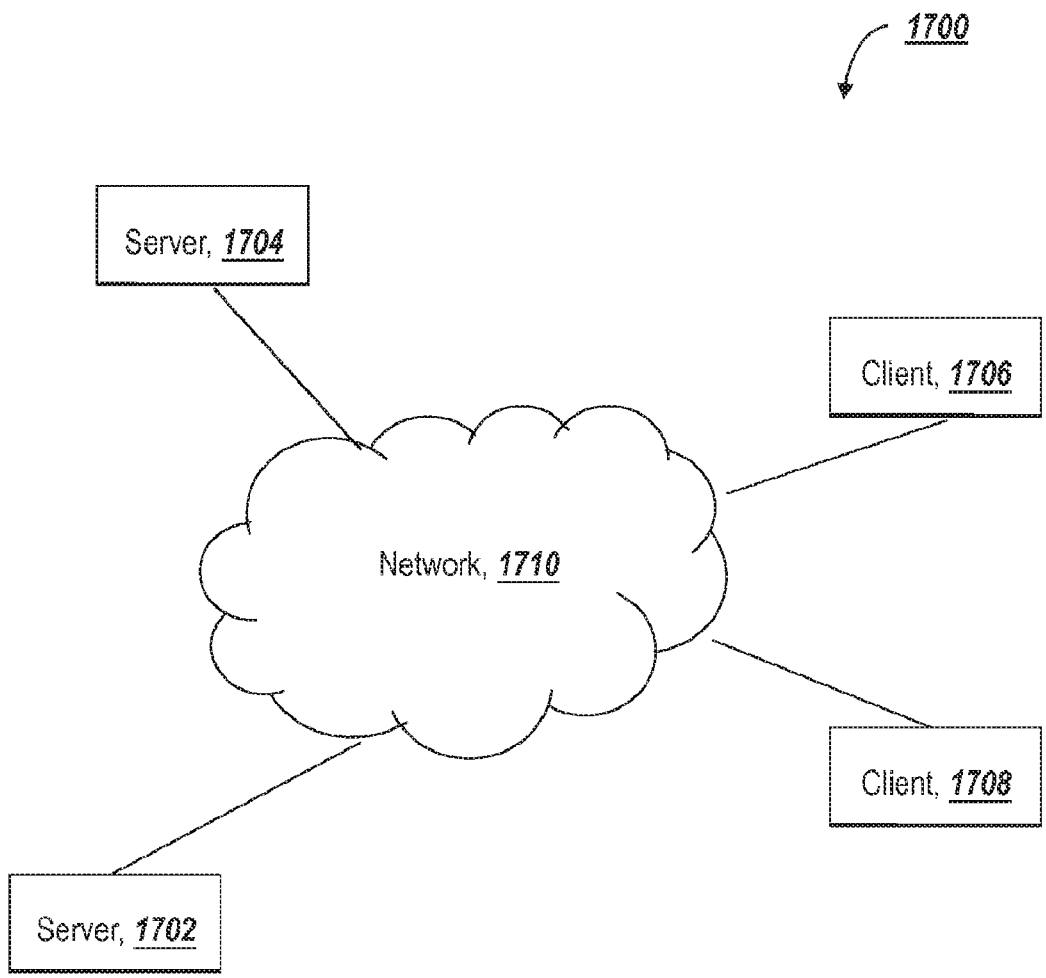
FIG. 17 is a block diagram of an exemplary network environment usable in exemplary embodiments.

FIG. 17 depicts an exemplary network environment 1710 suitable for implementation of embodiments. The network environment 1710 may include one or more servers 1702 and 1704 coupled to one or more clients 1706 and 1708 via a communication network 1710. Notably, each of the one or more servers 1702 and 1704 and one or more clients 1706 and 1708 may be implemented as a computing device 2300 as described with respect to FIG. 23. Thus, each of the one or more servers 1702 and 1704 and the one or more clients 1706 and 1708 may include a network interface 2312 and a network device 2322 to enable the servers 1702 and 1704 to communicate with the clients 1706 and 1708 via the communication network 1710. The communication network 1710 may include, but is not limited to, the Internet, an intranet, a LAN (Local Area Network), a WAN (Wide Area Network), a MAN (Metropolitan Area Network), a wireless network, an optical network, and the like. The communication facilities provided by the communication network 1710 are capable of supporting collaborative analysis and research efforts as disclosed herein.

In an exemplary embodiment, one or more of the servers 1702, 1704 may advantageously provide a cloud environment and capability for storing data related to the methods described herein, for example, in accordance with the data storage systems described with reference to FIGS. 1A-1C. Certain exemplary servers may be tiling servers that store image data as discrete tiles of data at different layers of resolution. The servers 1702, 1704 may transfer image data to a requesting client in a streaming manner as needed. In some exemplary embodiments, one or more of the servers 1702, 1704 may also provide an environment and capability for analyzing data related to the methods described herein.

One or more of the clients 1706, 1708 may host or implement one or more of the graphical user interfaces described herein for use by a user of the client computing device. The client 1706, 1708 may remotely access the one or more servers 1702, 1704 to request portions of data (e.g., one or more tiles of data) needed to render and/or update the graphical user interfaces. In response, the server may retrieve only those portions of data requested and may transfer the data to the requesting client in a streaming manner. In some embodiments, the data may be requested by the client and transferred by the server to the client in a real time manner as a user interacts with a graphical user interface rendered on the client or may, alternatively, be performed after a time lag after the user interacts with the user interface.

In exemplary embodiments, the transfer of requests from a client to a server and/or the transfer of data from a server to a client may be subject to a particular condition, such as a license agreement.

In an exemplary embodiment, a server implemented as a tiling server can operate to retrieve, process, and serve individual tiles in response to requests received from one or more clients programmed to execute an embodiment of the GUIs 100, 1000, and/or 1600. The communication between the client and the tiling server can be facilitated via communication protocol, such as, for example, the Hypertext Transport Protocol. The tiling server can be accessible by a client using a handler interface, such as a standard web-based HTTP interface. The handler interface can provide a flexible data request structure that utilizes, for example, an encrypted JavaScript Object Notation (JSON) based image data query that encapsulates functionality of the tiling server.

Figure 18:
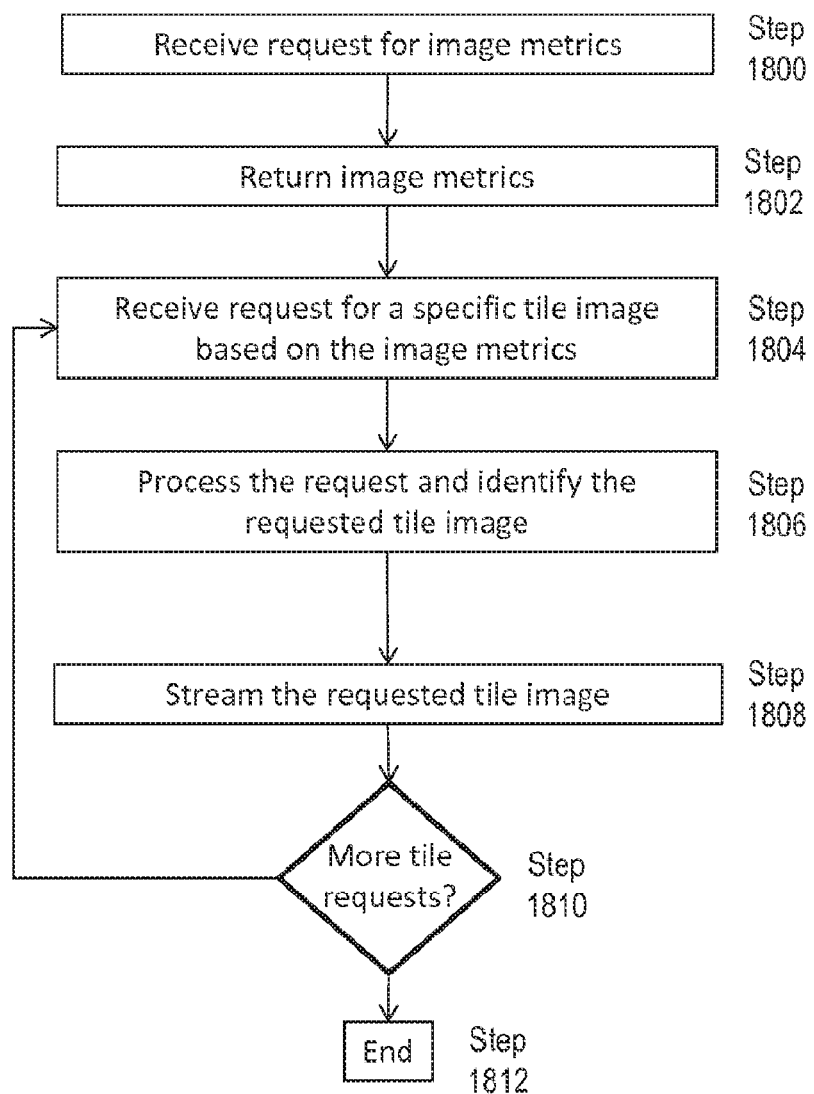
FIG. 18 shows an exemplary flowchart illustrating an interaction between a client computing device programmed to execute any of the user interfaces described herein and a tiling image data server.

FIG. 18 shows an exemplary flowchart illustrating an interaction between a client computing device programmed to execute an embodiment of the GUIs 100, 1000, and/or 1600 and the tiling server based on a tile image request that can be submitted to the tiling server. To request tiles, the client can be programmed to submit an image metrics request in step 1800. The image metric request can be used by the client to obtain information that can be used to query the tiling server for the tiles. For example, the process request can request image metrics, such as an image height, image width, tile height, tile width, number of image directories, a minimum pyramid level (e.g., a minimum resolution level), and a maximum pyramid level (e.g., a maximum resolution level), which can be returned to the client by the tiling server. The tiling server can return the requested image metrics to the client in step 1802.

Once the client has received the requested image metrics, the client can request a specific tile image using the image metrics in step 1804. In an exemplary embodiment, the tiles can be requested by the client in sequence. The request for a tile created by the client can include information that specifies what tile image is desired. In response to the request for a tile, the tiling server processes the request, and identifies the tile image in step 1806. In step 1808, the tiling server streams the requested tile image to the client and in step 1810 the tiling server waits for the next tile request from the client. If the client requests another tile image, the process repeats from step 1804. Otherwise, the process ends at step 1812. In exemplary embodiments, the tiling server can use caching to reduce redundant and time-consuming calls to the case manager and/or file system, thus speeding up its responsiveness to the client requests.

When the client requests a tile, the request can include information to identify the specific tile requested. In one embodiment, the tile can be retrieved from the tiling server based on separate HTTP requests for each tile. In exemplary embodiments, requests initiated by the client can include requests for thumbnails of the slide images, requests for tiles that are composed from one or more channels, requests for image metrics that include the image size, tile size, and available pyramid levels, and/or can include any other suitable requests for information.

In an exemplary embodiment, the requests initiated by the client can utilize a universal resource locator (URL) protocol to create URL queries that contain the parameters (e.g., image metrics), such as an information parameter, an index parameter, level parameter, image height parameter, image width parameter, tile height parameter, tile width parameter, and/or any other suitable information for specifying a particular tile to be retrieved. As described herein, the client can be programmed to submit an image metrics request for the parameters and the server can respond to the request by providing the parameters and their associated values. The info parameter can be a Boolean value that indicates the type of information (e.g., image metrics or tile images) being requested by the URL query. For example, when the info parameter is set to "true," the URL query is configured to request image metrics and if the info parameter is set to "false" or not specified, the URL query is configured to request tile images. The index parameter can include integer values indicating the x-axis and y-axis tile location for a requested tile. The level parameter can include an integer value indicating the level from the image pyramid (e.g., scale and/or resolution) that should be returned. In an exemplary embodiment the level parameter can include a minimum level parameter indicating the lowest level from the image pyramid and a maximum level parameter indicating the highest level from the image pyramid. The image height parameter corresponds to a height of the entire image and the image width parameter corresponds to the width of the entire image. The tile height parameter corresponds to the height of a tile for the entire image and the tile width parameter corresponds to the width of a tile for the entire image.

Figure 21:
FIG. 21 shows an example of a tile image request that may be generated by a client computing device.

FIG. 19 shows an example of an image metrics request 1900 that can be created by the client, where an info parameter 1902 is set to "true," and FIG. 20 shows an example of an XML-based response 20 to the image metrics request provided by the tiling server including, for example, values for the image height parameter 2002, image width parameter 2004, tile height parameter 2006, tile width parameter 2008, and minimum pyramid level parameter 2010, and maximum pyramid level parameter 2012. FIG. 21 shows an example of a tile image request 2100 that can be created by the client. The tile image request 2100 can include values 2102 for the image metrics 2104 to specify a specific tile image in the request 2100.

Figure 22:
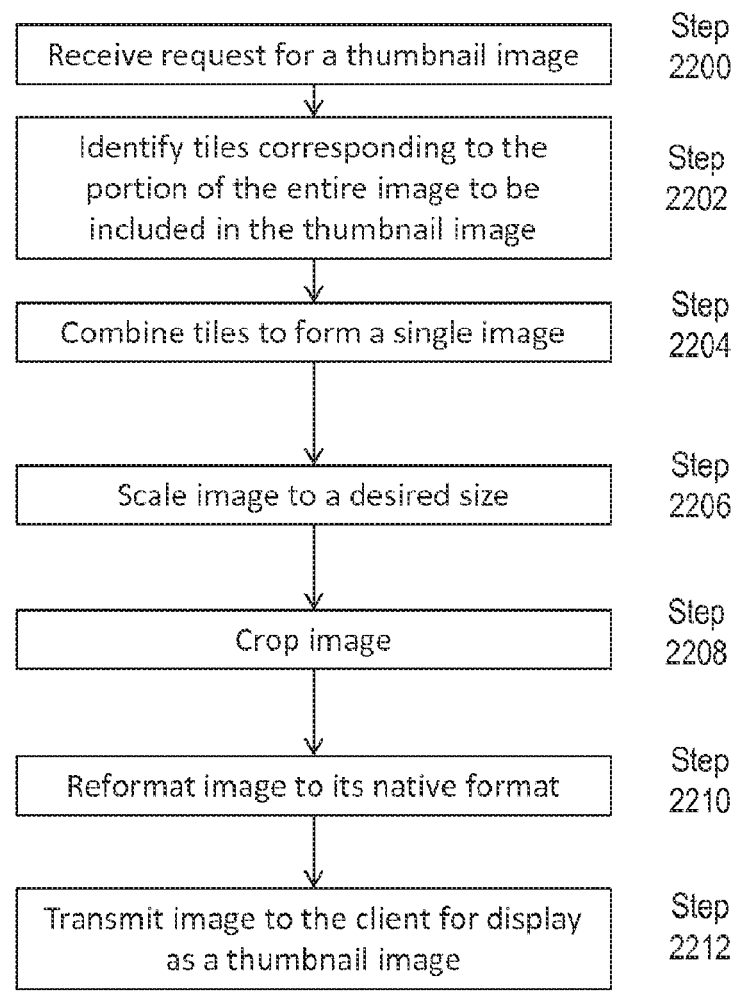
FIG. 22 is a flowchart illustrating an interaction between a client computing device programmed to execute any of the user interfaces described herein and a tiling image data server.

FIG. 22 is a flowchart illustrating an interaction between a client programmed to execute an embodiment of the GUIs 100, 1000, and/or 1600 and the tiling server based on a thumbnail image request that can be submitted to the tiling server. For embodiments in which thumbnails can be displayed by a client executing an embodiment of the GUIs 100, 1000, and/or 1600, the client can submit an image metric request and can receive the image metrics from the tiling server as described above with respect to FIGS. 18-20. Once the client has received the requested image metrics, the client can request a specific thumbnail image using the image metrics in step 2200. The request for a thumbnail created by the client can include information that specifies what portion of the entire image should be included in the thumbnail. In response to the request for a thumbnail, the tiling server processes the request, and identifies the tiles corresponding to the portion of the entire image to be included in the thumbnail image in step 2202. The tiles identified by the tiling server can be retrieved from a largest pyramid level that most closely matches the zoom level of the thumbnail image specified in the request. In step 2204, the tiling server can combine the tiles retrieved for the thumbnail into a single image and in step 2206, the tiling server scales the image down to a desired size. In step 2208, the image is cropped to match the dimensions of the requested thumbnail image and in step 2210, the image is transmitted to the client for display in one or more of the GUIs 100, 1000, and/or 1600 as a thumbnail image.

Exemplary Computing Devices

Systems and methods disclosed herein may include one or more programmable processing units having associated therewith executable instructions held on one or more computer readable media, RAM, ROM, hard drive, and/or hardware. In exemplary embodiments, the hardware, firmware and/or executable code may be provided, for example, as upgrade module(s) for use in conjunction with existing infrastructure (for example, existing devices/processing units). Hardware may, for example, include components and/or logic circuitry for executing the embodiments taught herein as a computing process.

The term "computer-readable medium," as used herein, refers to a non-transitory storage hardware, non-transitory storage device or non-transitory computer system memory that may be accessed by a controller, a microcontroller, a computational system or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM) and the like.

Displays and/or other feedback means may also be included, for example, for rendering a graphical user interface, according to the present disclosure. The display and/or other feedback means may be stand-alone equipment or may be included as one or more components/modules of the processing unit(s). In exemplary embodiments, the display and/or other feedback means may be used to simultaneously describe both morphological and statistical representations of a field of view corresponding to an image, or a portion of an image, of a biological tissue sample.

The actual software code or control hardware which may be used to implement some of the present embodiments is not intended to limit the scope of such embodiments. For example, certain aspects of the embodiments described herein may be implemented in code using any suitable programming language type such as, for example, assembly code, C, C# or C++ using, for example, conventional or object-oriented programming techniques. Such code is stored or held on any type of suitable non-transitory computer-readable medium or media such as, for example, a magnetic or optical storage medium.

As used herein, a "processor," "processing unit," "computer" or "computer system" may be, for example, a wireless or wire line variety of a microcomputer, minicomputer, server, mainframe, laptop, personal data assistant (PDA), wireless e-mail device (for example, "BlackBerry," "Android" or "Apple," trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include non-transitory storage medium for storing software, including a hard disk, an optical disk, floppy disk, ROM (read only memory), RAM (random access memory), PROM (programmable ROM), EEPROM (electrically erasable PROM), flash memory storage devices, or the like.

Figure 23:
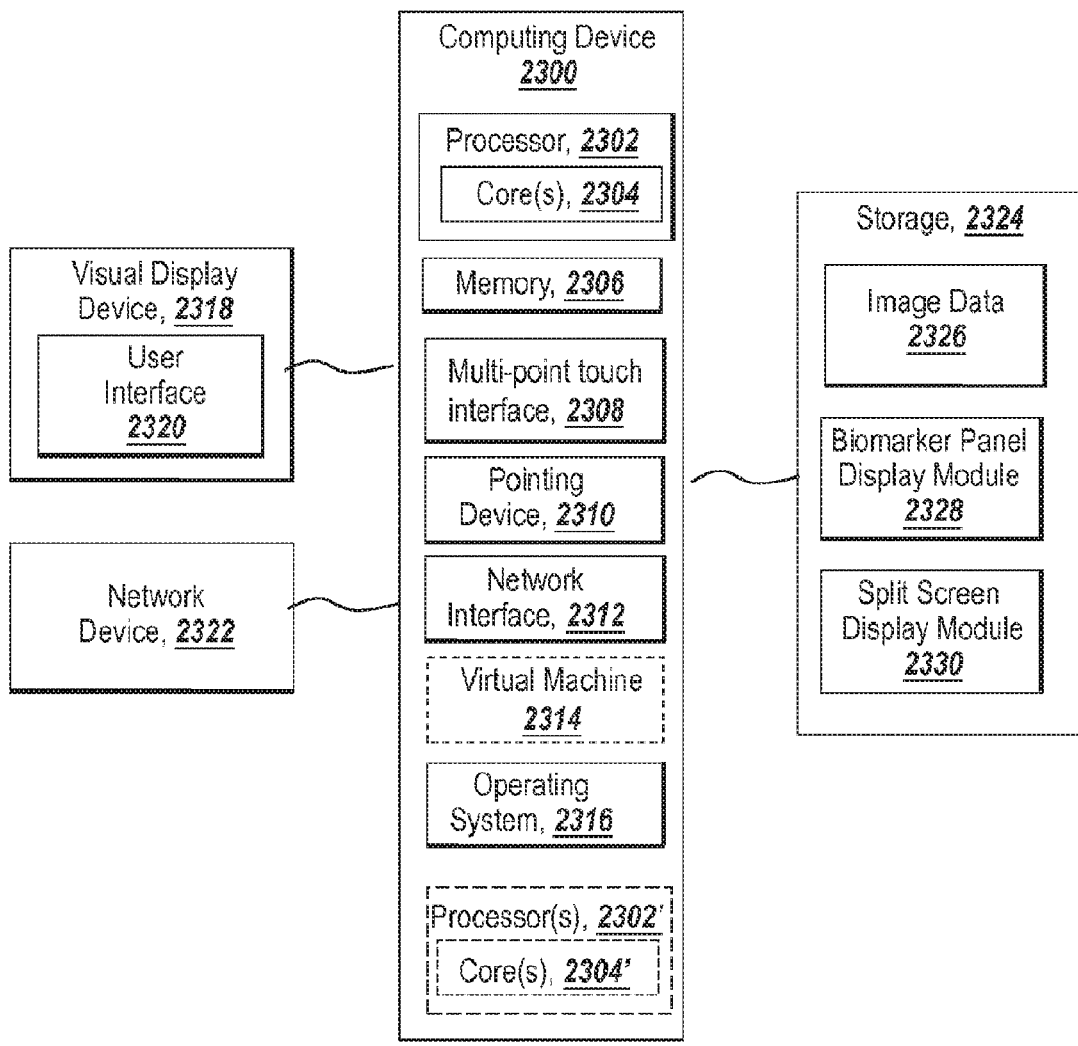
FIG. 23 is a block diagram of an exemplary computing device usable in exemplary embodiments.

FIG. 23 depicts a block diagram representing an exemplary computing device 2300 that may be used to implement the systems and methods disclosed herein. The computing device 2300 may be any computer system, such as a workstation, desktop computer, server, laptop, handheld computer, tablet computer (e.g., the iPad™ tablet computer), mobile computing or communication device (e.g., the iPhone™ mobile communication device, the Android™ mobile communication device, and the like), or other form of computing or telecommunications device that is capable of communication and that has sufficient processor power and memory capacity to perform the operations described herein. In exemplary embodiments, a distributed computational system may include a plurality of such computing devices.

The computing device 2300 includes one or more non-transitory computer-readable media having encoded thereon one or more computer-executable instructions or software for implementing the exemplary methods described herein. The non-transitory computer-readable media may include, but are not limited to, one or more types of hardware memory and other tangible media (for example, one or more magnetic storage disks, one or more optical disks, one or more USB flash drives), and the like. For example, memory 2306 included in the computing device 2300 may store computer-readable and computer-executable instructions or software for implementing a graphical user interface as described herein. The computing device 2300 also includes processor 2302 and associated core 2304, and in some embodiments, one or more additional processor(s) 2302' and associated core(s) 2304' (for example, in the case of computer systems having multiple processors/cores), for executing computer-readable and computer-executable instructions or software stored in the memory 2302 and other programs for controlling system hardware. Processor 2302 and processor(s) 2302' may each be a single core processor or a multiple core (2304 and 2304') processor.

Virtualization may be employed in the computing device 2300 so that infrastructure and resources in the computing device may be shared dynamically. A virtual machine 2314 may be provided to handle a process running on multiple processors so that the process appears to be using only one computing resource rather than multiple computing resources. Multiple virtual machines may also be used with one processor.

Memory 2306 may include a computer system memory or random access memory, such as DRAM, SRAM, EDO RAM, and the like. Memory 2306 may include other types of memory as well, or combinations thereof.

A user may interact with the computing device 2300 through a visual display device 2318, such as a screen or monitor, which may display one or more graphical user interfaces 2320 provided in accordance with exemplary embodiments described herein. The visual display device 2318 may also display other aspects, elements and/or information or data associated with exemplary embodiments.

The computing device 2300 may include other I/O devices for receiving input from a user, for example, a keyboard or any suitable multi-point touch interface 2308, a pointing device 2310 (e.g., a mouse, a user's finger interfacing directly with a display device). As used herein, a "pointing device" is any suitable input interface, specifically, a human interface device, that allows a user to input spatial data to a computing system or device. In an exemplary embodiment, the pointing device may allow a user to provide input to the computer using physical gestures, for example, pointing, clicking, dragging, dropping, and the like. Exemplary pointing devices may include, but are not limited to, a mouse, a touchpad, a finger of the user interfacing directly with a display device, and the like.

The keyboard 2308 and the pointing device 2310 may be coupled to the visual display device 2318. The computing device 2300 may include other suitable conventional I/O peripherals. The I/O devices may facilitate implementation of the one or more graphical user interfaces 2320, for example, implement one or more of the graphical user interfaces described herein.

The computing device 2300 may include one or more storage devices 2324, such as a durable disk storage (which may include any suitable optical or magnetic durable storage device, e.g., RAM, ROM, Flash, USB drive, or other semiconductor-based storage medium), a hard-drive, CD-ROM, or other computer readable media, for storing data and computer-readable instructions and/or software that implement exemplary embodiments as taught herein. In exemplary embodiments, the one or more storage devices 2324 may provide storage for data that may be generated by the systems and methods of the present disclosure. For example, a storage device 2324 may provide storage for image data 2326 corresponding to biological specimens (e.g., in the form of tiled multi-resolution data structures), a biomarker panel display module 2328 programmed and configured to implement a biomarker panel and associated thumbnail images described herein, and a split screen display module 2330 programmed or configured to implement a split screen display as described herein. The one or more storage devices 2324 may further provide storage for computer readable instructions relating to one or more methods as described herein. The one or more storage devices 2324 may be provided on the computing device 2300 and/or provided separately or remotely from the computing device 2300.

The computing device 2300 may include a network interface 2312 configured to interface via one or more network devices 2322 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 2312 may include a built-in network adapter, network interface card, PCMCIA network card, card bus network adapter, wireless network adapter, USB network adapter, modem or any other device suitable for interfacing the computing device 2300 to any type of network capable of communication and performing the operations described herein. The network device 2322 may include one or more suitable devices for receiving and transmitting communications over the network including, but not limited to, one or more receivers, one or more transmitters, one or more transceivers, one or more antennae, and the like.

The computing device 2300 may run any operating system 2316, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 2316 may be run in native mode or emulated mode. In an exemplary embodiment, the operating system 2316 may be run on one or more cloud machine instances.

One of ordinary skill in the art will recognize that exemplary computational system 2300 may include more or fewer modules than those shown in FIG. 23.

Referring now to FIGS. 24-39, the present invention provides a GUI 2500 providing both the split screen and digital prism features of the present invention as well as a snapshot capture feature for uploading selected images into an electronic record which may be saved and provided or formatted for a report detailing support for the user pathologist's findings in a given case. For example, the snapshot capture feature, or 'snapshot feature' or simply 'snapshot', may allow for all of the thumbnail images or split screen images to be saved into a record which is then saved on a local storage medium or on a server within a hardwired network or even on a cloud server. The record may then be available to local and/or remote reviewers, desirably along with other patient information. The term 'snapshot' refers to the images recorded by the snapshot capture feature. The present invention contemplates that the snapshot feature of the present invention may be employed with a GUI providing either or both of the split screen feature and digital prism feature of the present invention.

The snapshot capture feature of the present invention (and the snapshots of the images taken by this feature) provides multiple benefits to a user. For example, snapshots can be modified and re-sized as needed. The region that was captured may be denoted within a visible box, desirably with a distinct line color, which stays with the image of the slide until the snapshot is deleted. Desirably, snapshots are by default named with information which can tie them to a specific slide and specific capture region, this name may desirably be edited as needed. The present invention contemplates that snapshots may be reviewed in list mode or gallery mode. Desirably, in gallery mode, the size of the snapshot previews may be increased or decreased to suit the needs or tastes of the user. The present invention provides an "Update Report Data" button on the viewer interface so that snapshots can be uploaded to a case report by clicking the "Update Report Data" button. For the case report, the present invention provides the pathologist with the option to include all, some or none of the images viewed. The present invention further contemplates sorting the saved images by the region from which they were acquired. The present invention allows the snapshots to be saved to a local disk or other remote storage media so as to be recalled for use in presentations or further studies. Full resolution images may also be saved. The present invention further provides that the snapshots may be annotated with free-form text by the user. The present invention also contemplates that snapshots may be saved to a server that provides input to a report-builder tool, such that each saved snapshot is then available to include in a diagnostic report or a research report along with accompanying annotation.

A Digital Prism Snapshot of the present invention further provides for the capture of an image of a selected region that is presented with a single biomarker blend and may also capture the respective images of the remaining biomarkers in the same location. Additionally, the Digital Prism Snapshot allows a user to view a first biomarker in a location on the image of the patient sample and then capture both the image of the expression of that biomarker as well as images for the other biomarkers expressed in the same location or region that was selected using the first biomarker.

Figure 24:
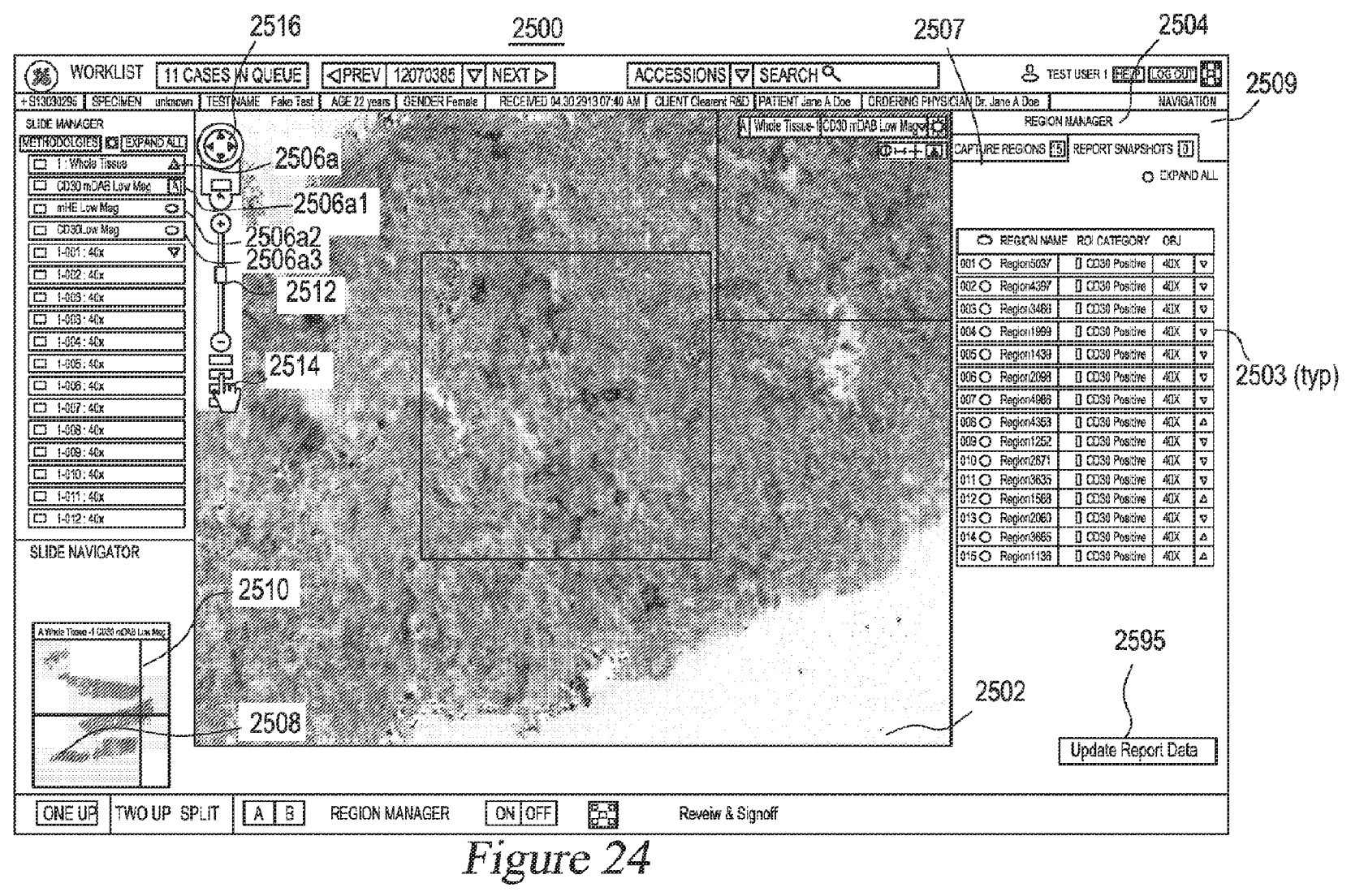

FIG. 24 depicts an embodiment of the present invention which provides a GUI 2500 allowing a user to intuitively browse any data that has been acquired on a multiplexing platform. It may be used by pathologists to evaluate results from, e.g., a Hodgkin Lymphoma lab developed test (LDT).

Figure 27:
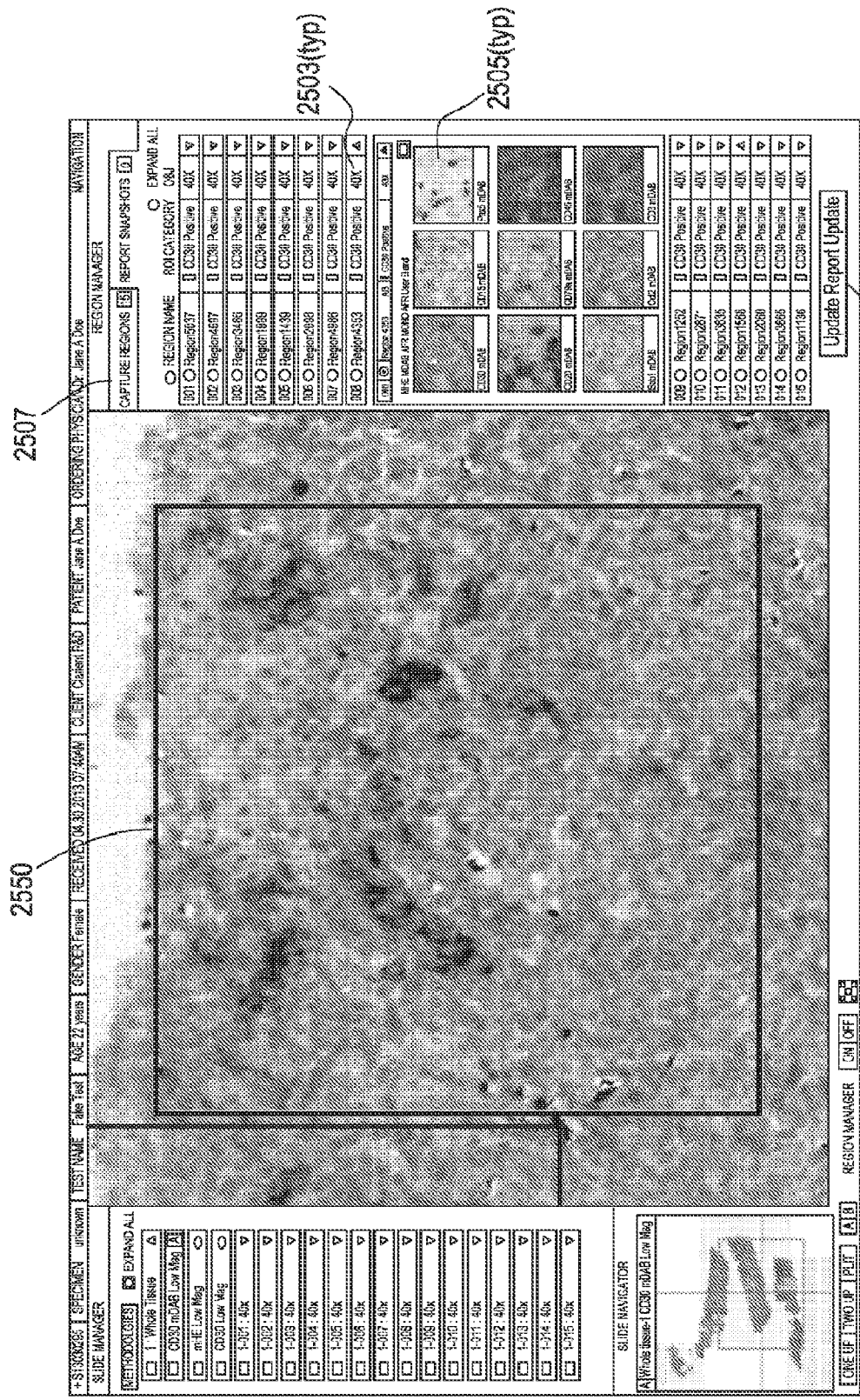
FIG. 27 shows this functionality of presenting a thumbnail image in the viewing panel.

GUI 2500 is seen to be a modification of GUI 1000 of the present invention, and like features are contemplated to provide like capabilities and functionality, including those described as exemplary to GUI 1000. GUI 2500 includes a main image panel 2502 for displaying a field of view of a biological specimen, and a region manager panel 2504 where a user can select either a capture region tab 2507 to display information pertaining to the capture regions or a report snapshot tab 2509 to display information pertaining to snapshots captured for use in a report. As shown in FIG. 24, when a user selects capture region tab 2507, the panel 2504 displays a list of selectable tabs 2503 for each of the capture regions selected from a sample image in the main image panel 2502. As shown in FIG. 27, when a user selects a particular tab 2503, panel 2504 will display under that selected tab 2503 a number of thumbnail images 2505 which each depict the biomarker expression associated with a region in the field of view of the biological specimen for that capture region. The field of view represented in main image panel 2502 typically corresponds to a portion of the entire image of a biological specimen, but may desirably show a region about the capture region selected in panel 2504.

With particular reference to FIG. 24, GUI 2500 includes a display type selection component 2506 which lists each region on the slide as a folder 2506a and each image within that region as a folder element and which may be used by a user to indicate one or more display types available for display in the main image panel 2502. For example, the display types 2506a-1, 2506a-2, and 2506a-3 could be CD30 mDAB, mHE, CD30 Low Mag (monochrome), respectively, which are each provided as a folder element under a folder 2506a for the whole tissue region. Upon display of a field of view in the main image panel 2502, GUI 2500 may be updated to include an image navigation component 2508 that displays the overall biological specimen of which the field of view displayed in the main image panel 2502 is a part. The image navigation component 2508 displays the biological specimen in accordance with the display type selected by the user.

Image navigation component 2508 desirably includes a field of view selection component 2510 (e.g. a reticle or any other suitable component) for delineating the field of view within the overall display of the biological specimen. View selection component 2510 allows the user to generally locate where the field of view (displayed in the main image panel 2502) can be found in the overall biological specimen (displayed in the image navigation component 2508). In some embodiments, the image navigation component 2508 is smaller than the main image panel 2502 and provides a lower resolution display of the biological specimen. In other embodiments, the image navigation component 2508 may be the same size as or larger than the main image panel 2502. The main image panel 2502 may include a zoom input tool 2512 for allowing a user to input a particular level of zoom or a relative level of zoom (e.g., using a zoom slider and/or zoom buttons). The current relative zoom level may be indicated on the image panel in a zoom indicator 2514. When the main image panel 2502 is updated according to a new zoom level, the field of view selection component 2510 in the image navigation component 2508 may be automatically updated to correctly delineate the corresponding updated field of view shown in the main image panel 2502. In an exemplary embodiment, a computing device running the user interface may determine that the new zoom level requires image data from a different resolution level in a tiled multi-resolution data structure, and may retrieve one or more tiles of image data from the resolution level.

Main image panel 2502 includes a pan input tool 2516 for panning to a new field of view in the biological specimen.

Panning may also be performed by clicking and holding on the image in main image panel 2502 and dragging the cursor across the panel, moving the underlying image with it. The main image panel 2502 also includes a capture region indicator component 2540 (e.g. a reticle or any other suitable component) for delineating the location of each capture region within the field of view displayed in the main image panel 2502. Once the additional high-resolution images from the selected capture regions have been acquired and loaded into the GUI 2500, the region manager panel 2504, e.g., as is shown in FIG. 27, is configured to include a set of one or more thumbnail images 2505 that represent the newly acquired capture region images. These images can then be loaded into the main image panel 2502 by clicking a thumbnail, after which the region manager panel 2504 may provide an indication of which thumbnail image corresponds to the image displayed in the main image panel.

As described for GUI 1000, the size and/or spatial dimensions of the thumbnail images 2505 in the biomarker tab 2503 may be set and/or scaled automatically based on the number of thumbnail images displayed and/or the size of the region manager panel 2504. In some embodiments, the user may be enabled to manually set or reset the size and/or dimensions of the thumbnail images.

When tab 2507 is selected, panel 2504 provides a first snaphot capture button 2590 for capturing snapshots of the displayed thumbnails 2505 and a second snapshot capture button 2592 for capturing images from the main image panel 2502. Buttons 2590 and 2592 desirably allow a user to save the locations of the snapshot images to the main server which may be retrieved later. GUI 2500 also includes an Update Report Data button 2595 which allows a user to save the images from the selected snapshots into a retrievable electronic record. The Update Report Data button 2595 desirably causes the saved images to be exported to a directory that can be used as input to a reporting tool for the user.

Desirably, the pathologists can access and operate GUI 2500 remotely through any internet browser. Once on GUI 2500 they can browse the case list and select the case that they wish to review. Alternatively, the pathologists can be alerted that a specific case is ready for review and they will be provided a direct link to that case.

Figure 25:
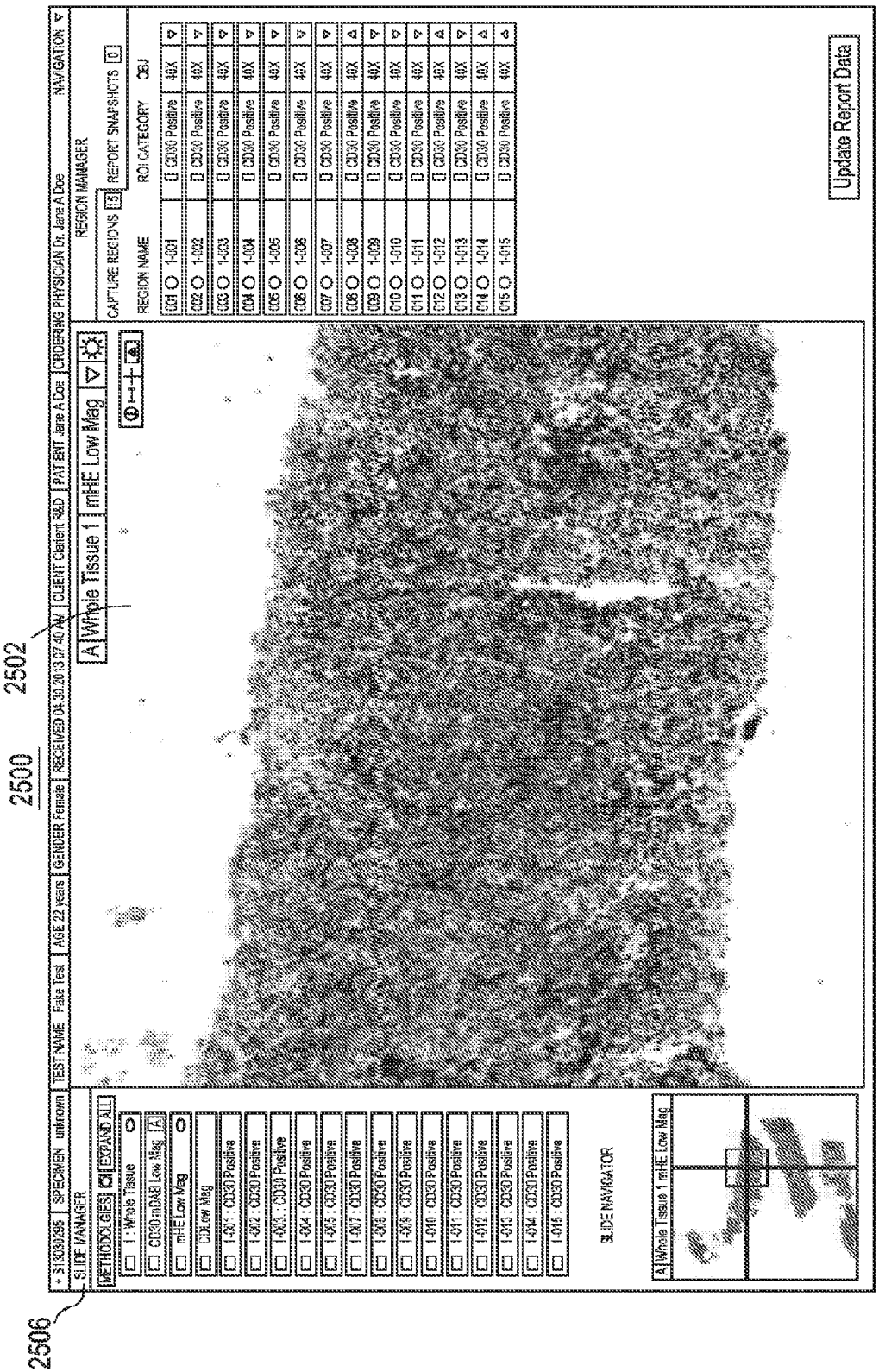
FIG. 25 depicts a molecular H&E image of a sample on a slide acquired at 10× magnification on a partial image of the viewer of FIG. 24.

Once a case is accessed from a server or other suitable storage device for electronic records, a pathologist can select from image selection component 2506 to view an overview of the slide that was acquired at 10× magnification, such as a molecular H&E (mH&E) image, as shown in FIG. 25. The mH&E is generated using an algorithm that converts grayscale immunofluorescent images into an image that is more familiar to the pathologist and easier to extract visual information from. The mH&E allows the pathologist to assess the overall morphology of a sample.

FIGS. 24-27 depict different views of low resolution images acquired at different zoom levels as depicted by the reticle 2510. The system allows users to designate regions for additional high resolution imaging, as depicted FIGS. 28-34. Once the low resolution and high resolution, here shown as 10× and 40×, respectively, images have been taken of a sample and its regions of interest, respectively, they are linked together though the GUI 2500 to allow for navigation between the low resolution images and the high resolutions images.

Figure 26:
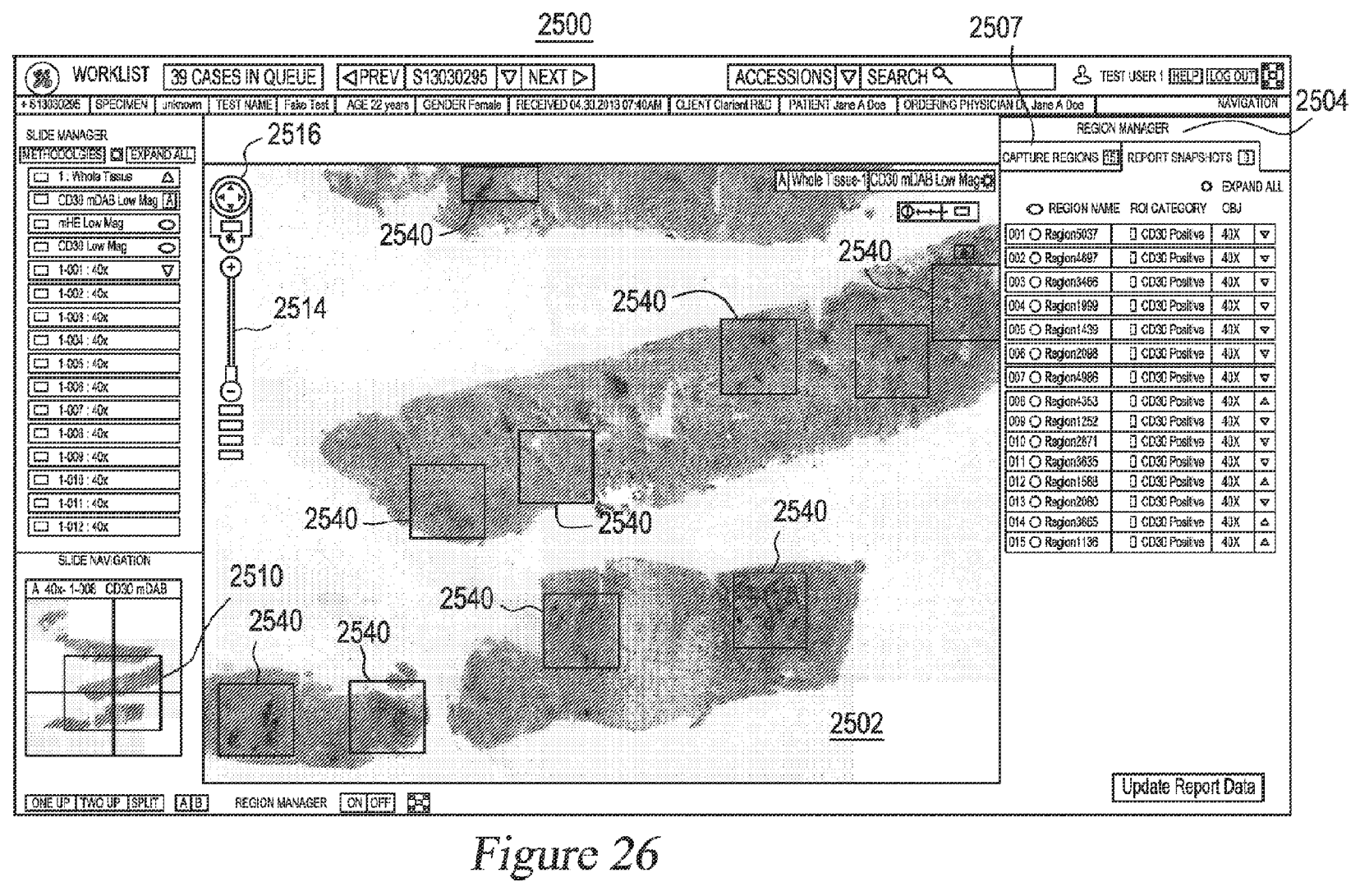

FIG. 26 shows the 10× display of an mDAB image of CD30. On the left side of the main image panel 2502 can be seen the zoom indicator 2514 which can be used to zoom in and out of an image. Capture regions that were previously selected are highlighted in boxes 2540 seen here. The pathologist can access other images by simply dragging and dropping the desired image into main image panel 2502 from the list of images in the image selection component on the left-hand side of GUI 2500 or by selecting a thumbnail 2505 from the acquired capture regions via biomarker tab 2503. As shown in FIG. 26, the pathologist is viewing a molecular DAB image of CD30 staining. Similar to mH&E, mDAB uses grayscale images of biomarker staining and converts them to an image resembling that of brightfield DAB stained images. For example, in the Hodgkin Lymphoma LDT, CD30 is a critical stain in that it identifies potential Reed-Sternberg (RS) cells that will be interrogated by future imaging rounds. In the beginning of the wet lab protocol a pathologist will look at this 10× CD30 mDAB image and select ROIs (or capture regions) which will be imaged in subsequent imaging rounds. Some of the ROIs that have already been selected are outlined in boxes 2540 on top of the CD30 mDAB image.

Navigating around an image is easy and intuitive. Panning is performed by clicking and dragging the image around the main image panel 2502 or by using the pan tool 2516, as desired. Zooming in and out can be done by scrolling a mouse wheel, dragging a slider bar of zoom input tool 2512, or selecting the desired magnification level. The pathologist can navigate around the 10× image until they find a pre-selected ROI which they would like to investigate. They can double click on the desired ROI and it is highlighted on the right hand region manager panel 2504. They can then expand the desired ROI to see all of the different visualization types and biomarkers that are available to review. Simply clicking on the thumbnail 2505 for one of the images will open it on the main image panel 2502. FIG. 27 shows this functionality, where an ROI has been double-clicked to be made active. The ROI shown by box 2540 is then outlined with a different-colored box 2550 and its corresponding tab 2503 is highlighted on the panel 2504.

Figure 28:
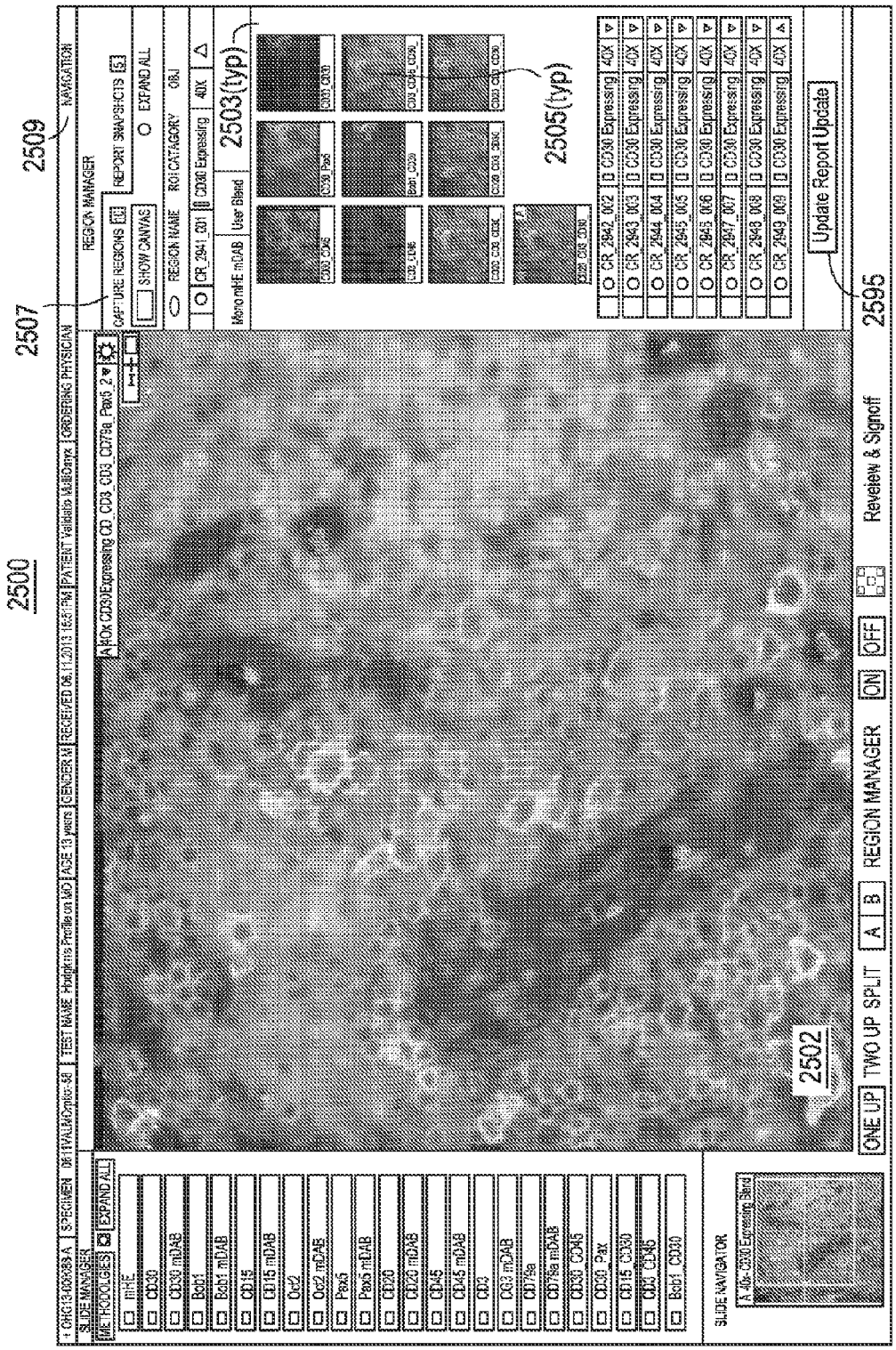
FIG. 28 depicts color blending of multiple monochrome images taken at 40× resolution.

Once the pathologist has identified a region of interest by navigating around the 10× image, they can see available images and color blends acquired at high-resolution (40×) for that region. They can also create color blends by combining two or more monochrome images. FIG. 28 shows this feature as it is displaying 5 different biomarkers, each in a different color.

Figure 29:
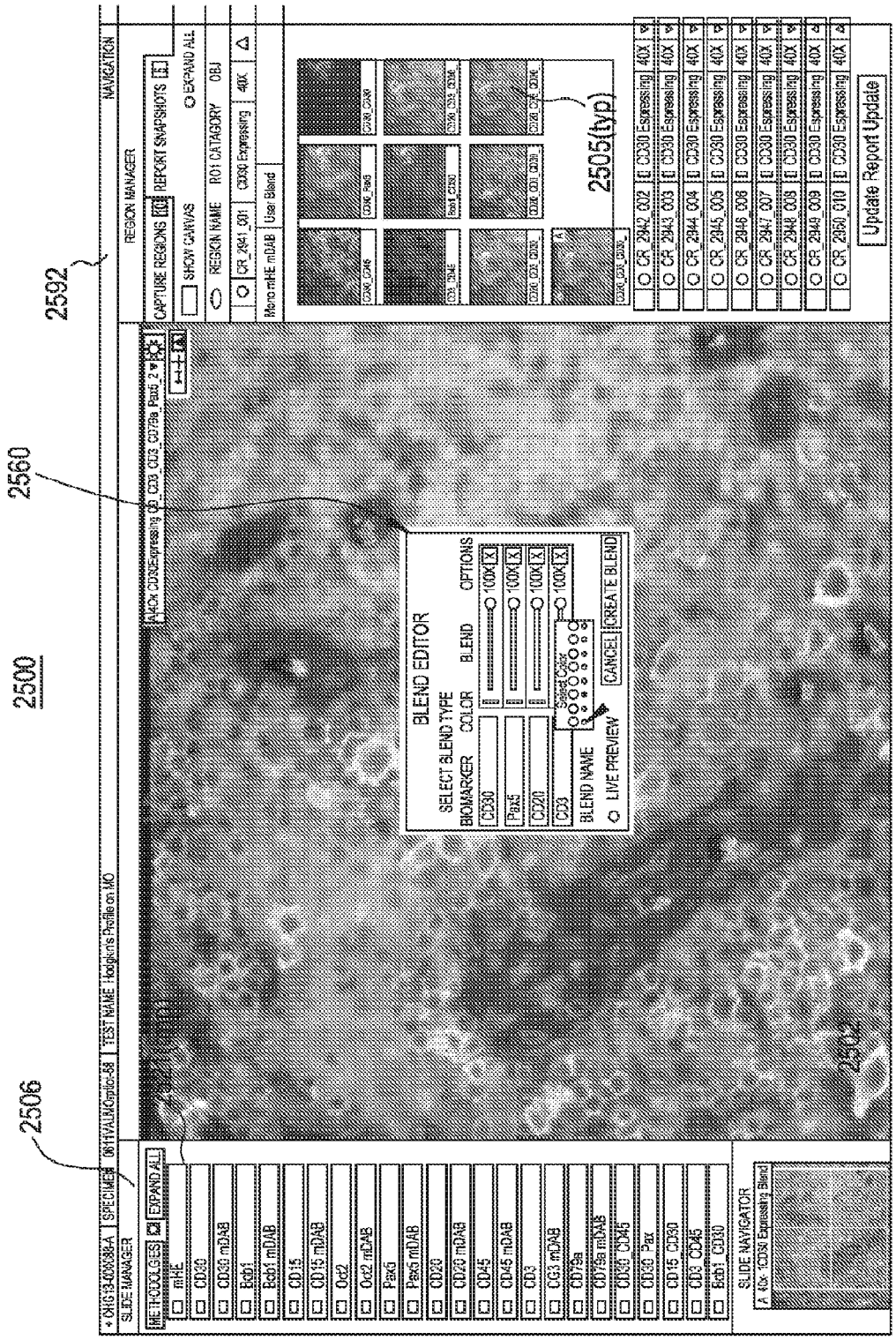
FIG. 29 further depicts the blend interface provided by the present invention on a partial view of the viewing panel of FIG. 28.

As shown in FIG. 29, for pathologists who are more used to traditional immunofluorescence images, the image blending feature can prove to be very useful. By clicking and dragging multiple grayscale images 2521 from the image selection component 2506 into the main image panel 2502, they can blend up to 5 images together with different colors representing each biomarker. By opening the blend interface 2555 the pathologist is provided with selectable control which allows the choice of which color combination he would prefer for the different biomarkers as well as the relative intensities for each biomarker.

Figure 30:
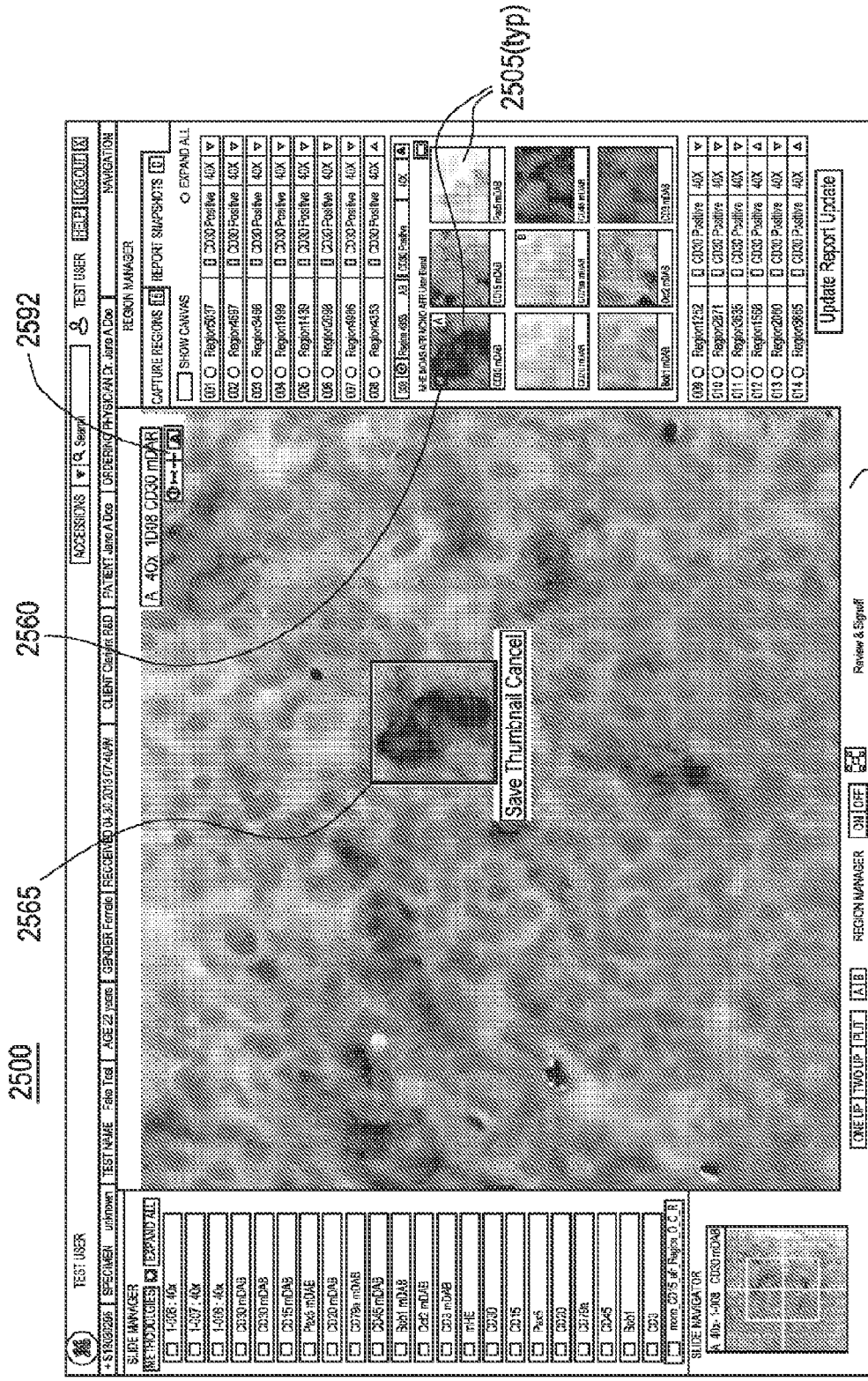
FIG. 30 depicts an alternate embodiment of the Digital Prism of the present invention.

With reference to FIG. 30, pathologists can view all of the available biomarkers, in this case nine different biomarkers, at once using the Digital Prism feature. By clicking a button 2560, shown here as a gear icon, located on the active thumbnail image (ie, the particular thumbnail image 2505 corresponding to the image shown in main display panel 2502), the pathologist is presented with a box 2565 which may itself be referred to as the "Digital Prism." When he or she moves this box to a particular cell or region of interest, the thumbnails 2505 on the right hand side will update to reflect what is within the Digital Prism 2565 for each of the 9 biomarkers. FIG. 30 shows the Digital Prism where there is a region selected by the box 2565 in the main display and the thumbnail images 2505 of the individual biomarkers on the right hand side have been updated to include the cells that are within that box 2565. For example, for the Hodgkin Lymphoma LDT, the most important information is what the phenotype of the CD30 positive cells are in the context of the other 8 biomarkers of the panel. Those 8 biomarkers are: CD15, CD20, Bob1, Oct2, Pax5, CD45, CD3, and CD79a. Multiplexing allows the pathologist to definitively state what the expression of all 9 biomarkers in a single cell. In the past, a pathologist would rely on a separate serial section for each biomarker, so the same cells were not being evaluated.

The Hodgkin Lymphoma biomarker panel consists of 9 biomarkers. Pathologists can continue using the Split Screen Display feature of the present invention for a one by one comparison, or they can view all 9 biomarkers at once using the Digital Prism feature of the present invention. By clicking a button located on the thumbnail images, the pathologist is presented with a blue box or Digital Prism feature described above. When he or she moves this box to a particular cell or region of interest, the thumbnails on the right hand side will update to reflect what is within the Digital Prism for each of the 9 biomarkers. Referring again to FIG. 30, one can clearly see that this single cell which the pathologist is focusing on is CD30 positive, Pax5 negative, as well as the relative presence or absence of the other biomarkers in their respective thumbnail images.

Figure 31:
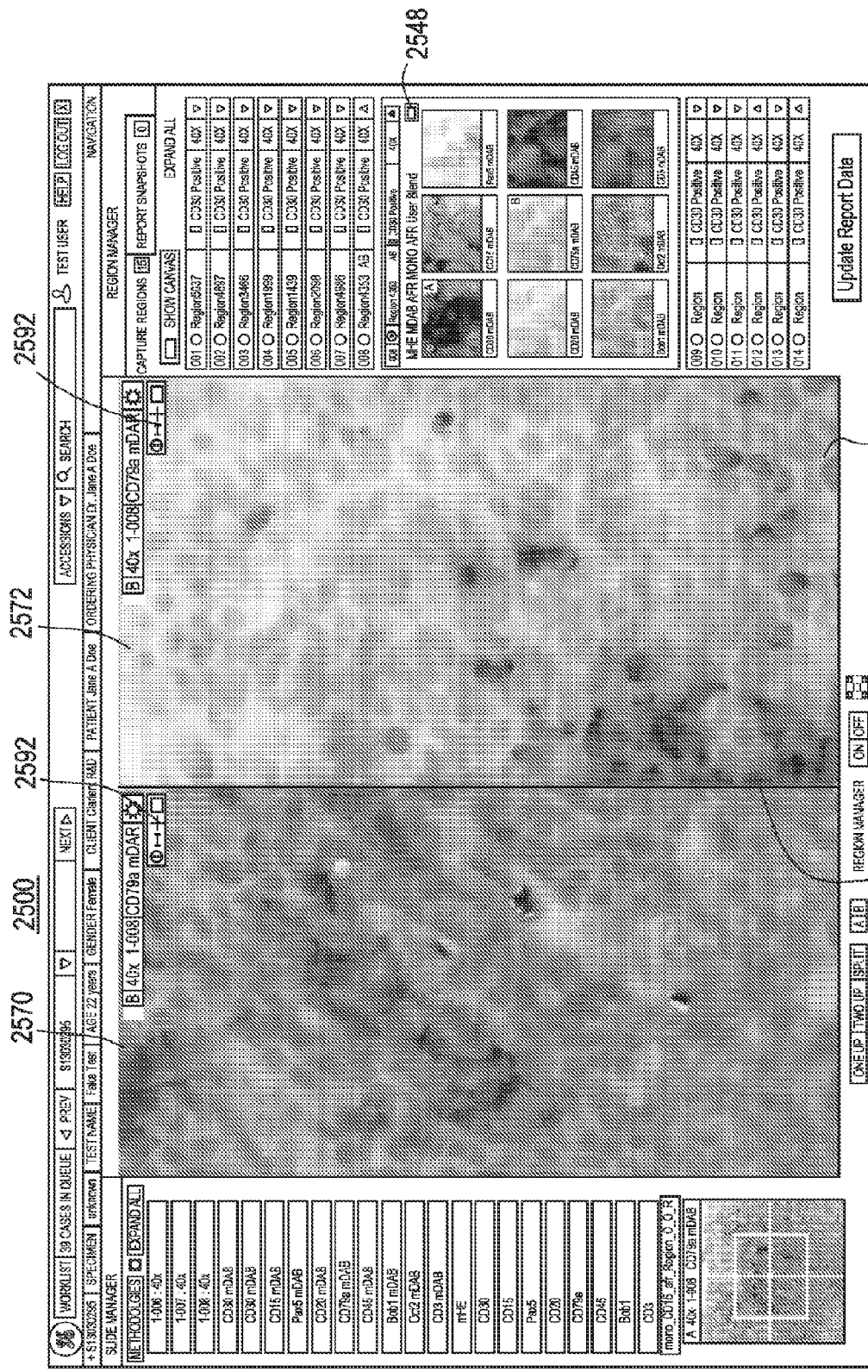
FIG. 31 depicts the selection of an mDAB CD30 image on one panel, and mDAB Pax5 image in the adjacent panel on a partial view of the viewing panel of FIG. 28.
Figure 32:
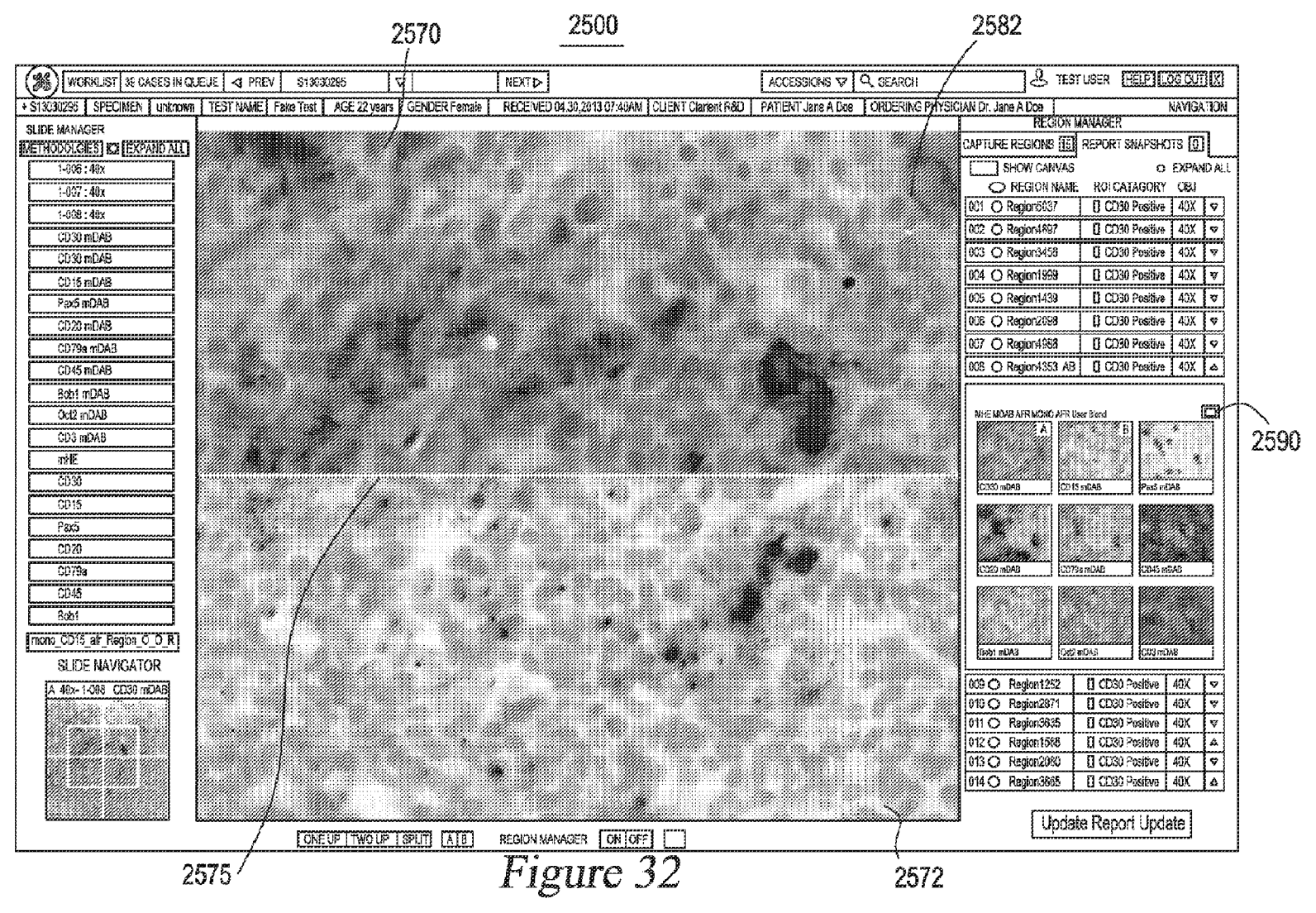
Figure 33:
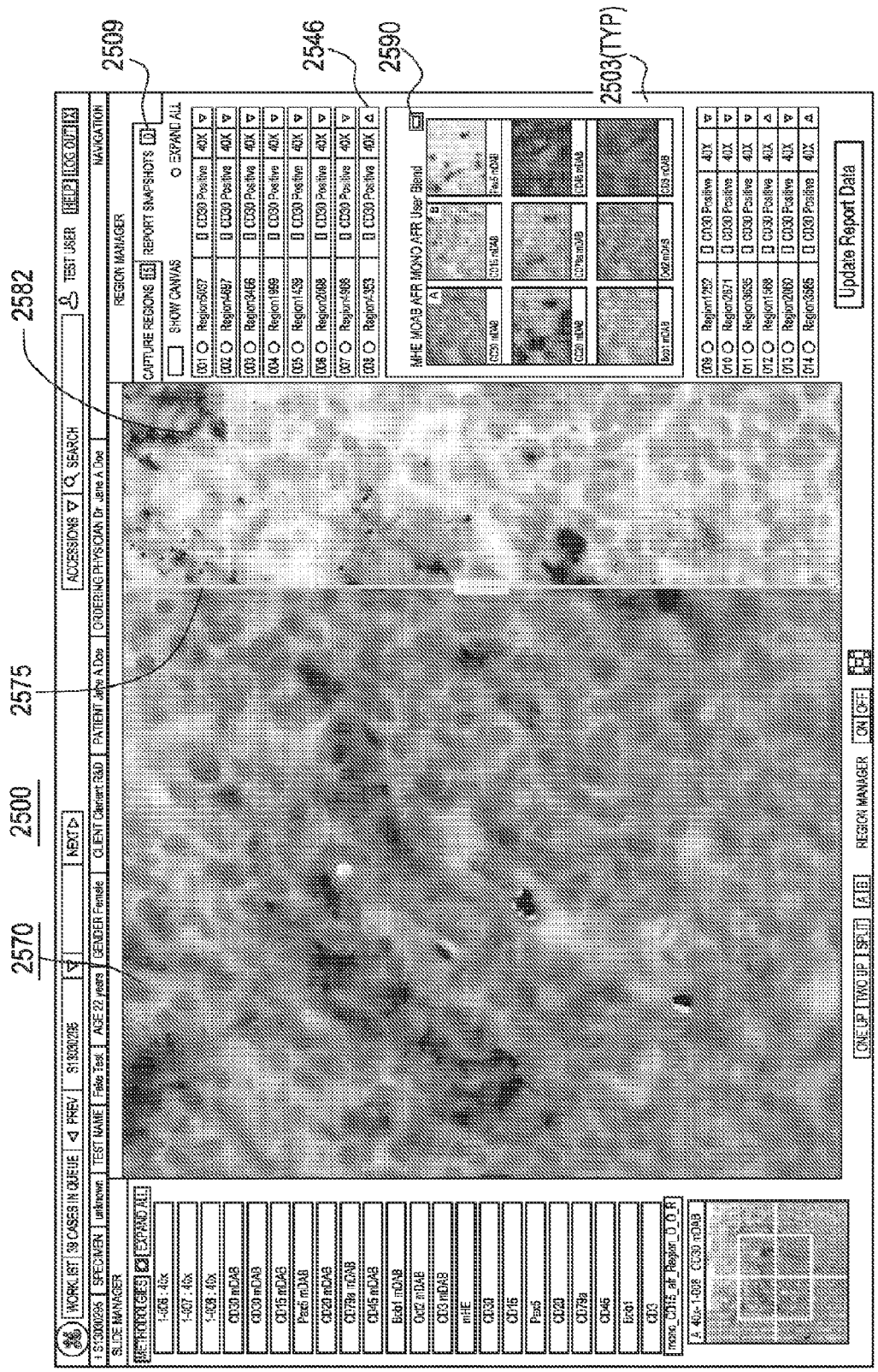
FIG. 33 depicts one selectable location for the bar distinguishing the two images selected for viewing on a partial view of the viewing panel of FIG. 28.

In FIG. 31, the pathologist has selected an mDAB CD30 image on a first sub-panel 2570, and mDAB Pax5 image in the adjacent second sub-panel 2572. If desired, they can change the orientation of the two images to be vertical or horizontal, as shown in FIG. 32. In either orientation, they can then drag bar 2575 across the image to continuously switch between the CD30 and Pax5 images, as the bar is depicted in a different location in FIG. 33. By doing so, one can clearly see the difference in biomarker expression across the same region of the tissue. Such multiplexing allows the user to determine whether cells that are positive for one biomarker are also positive for another biomarker such as, in this example, whether or not the CD30 positive cells are also positive for CD15.

Figure 34:
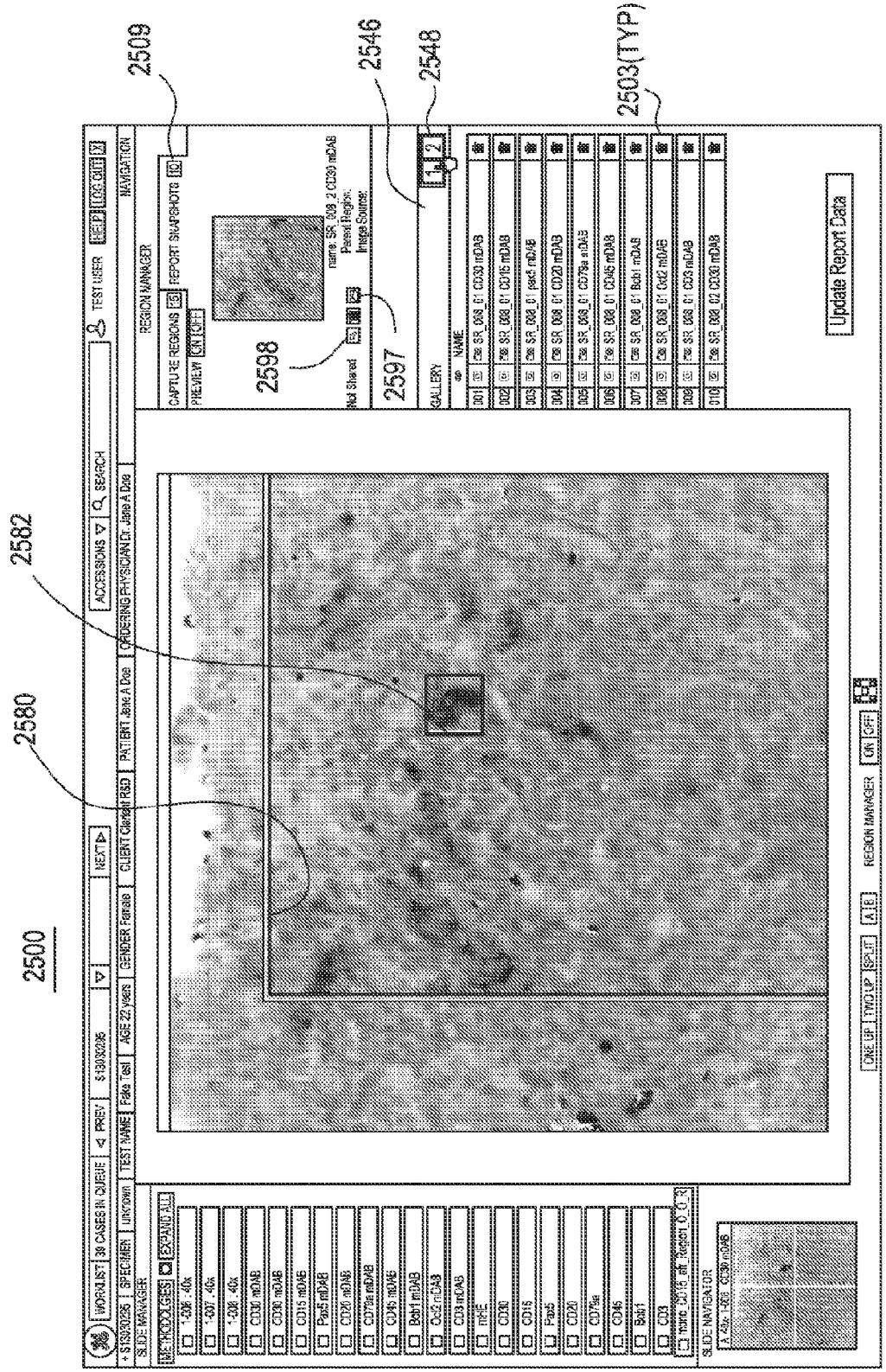
FIG. 34 shows two different regions of interest that were captured using the Snapshot capture feature of the present invention, as outlined in the two boxes on the main display.
Figure 35:
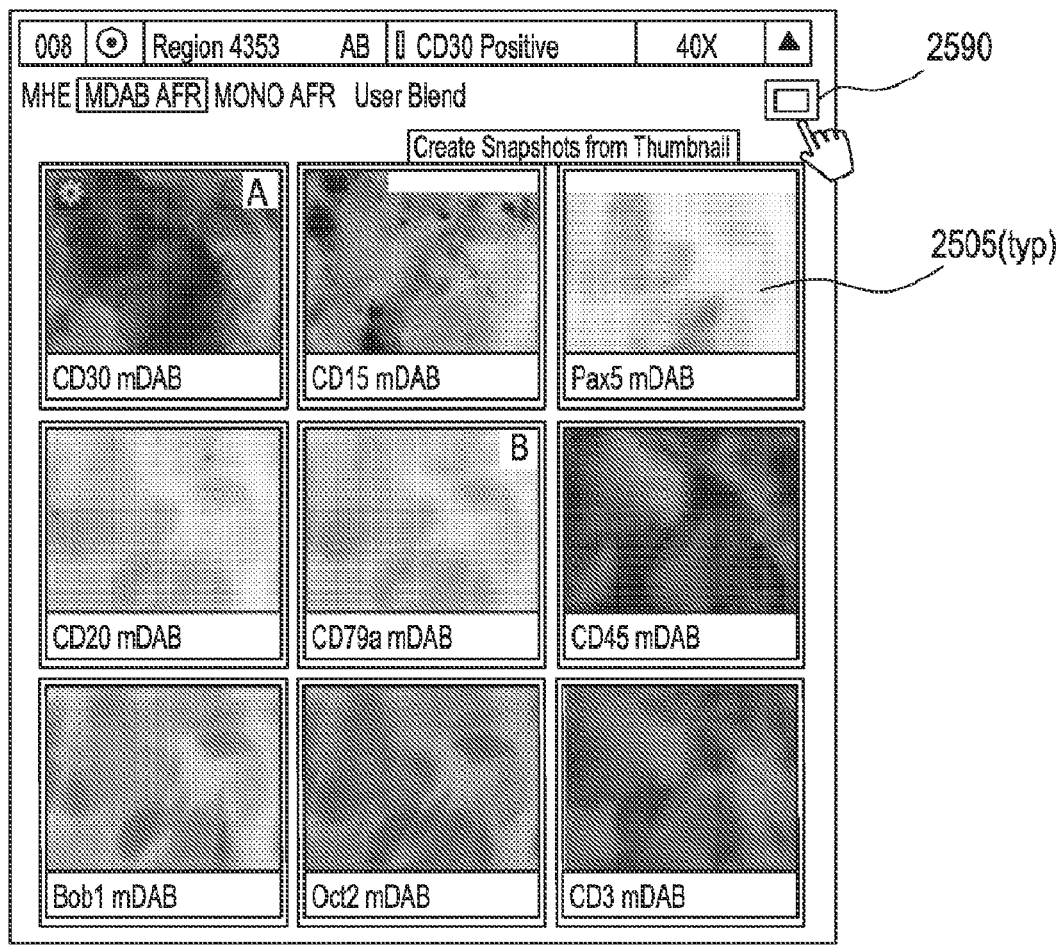
FIG. 35 depicts the present invention allowing for all of the thumbnail images to be captured using the Snapshot feature of the present invention.
Figure 36:
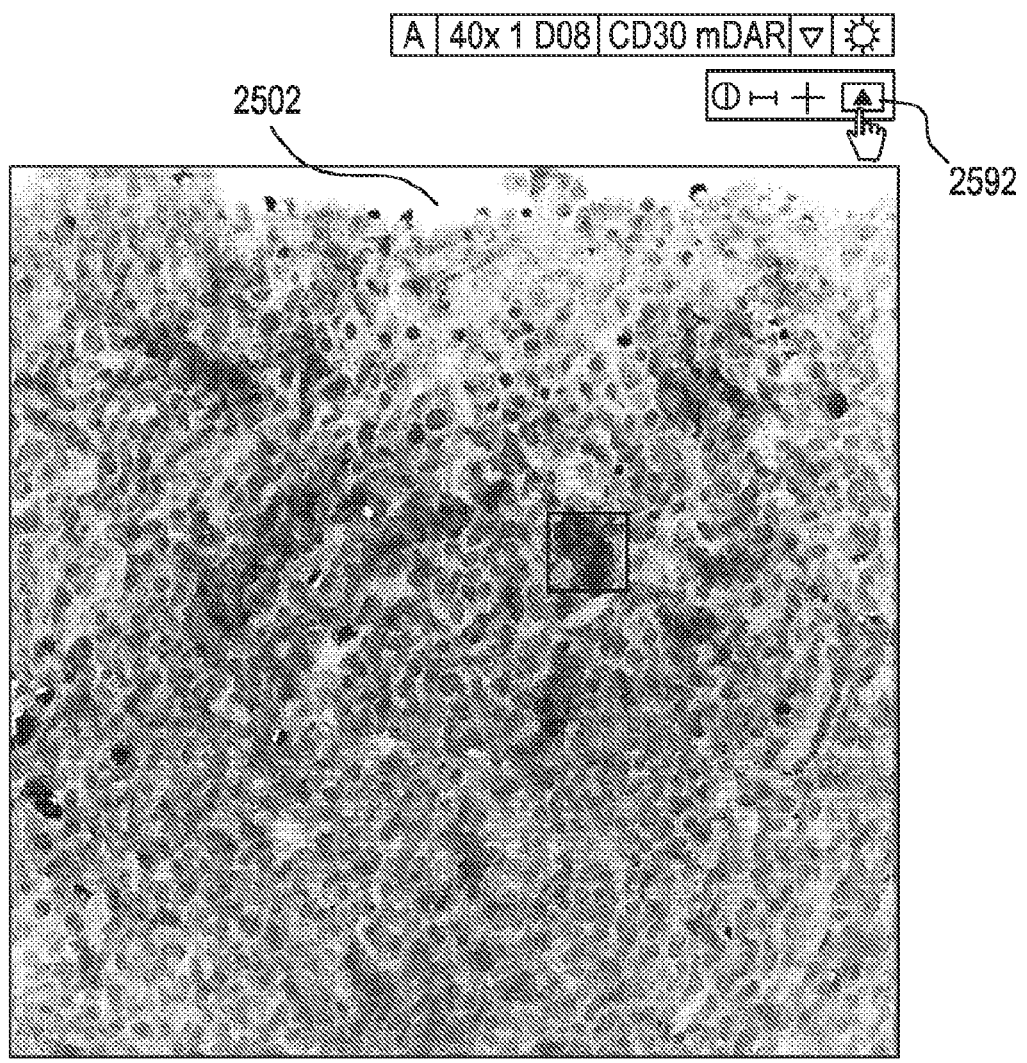
FIG. 36 depicts the present invention allowing for the entire field to be captured using the Snapshot feature of the present invention
Figure 37:
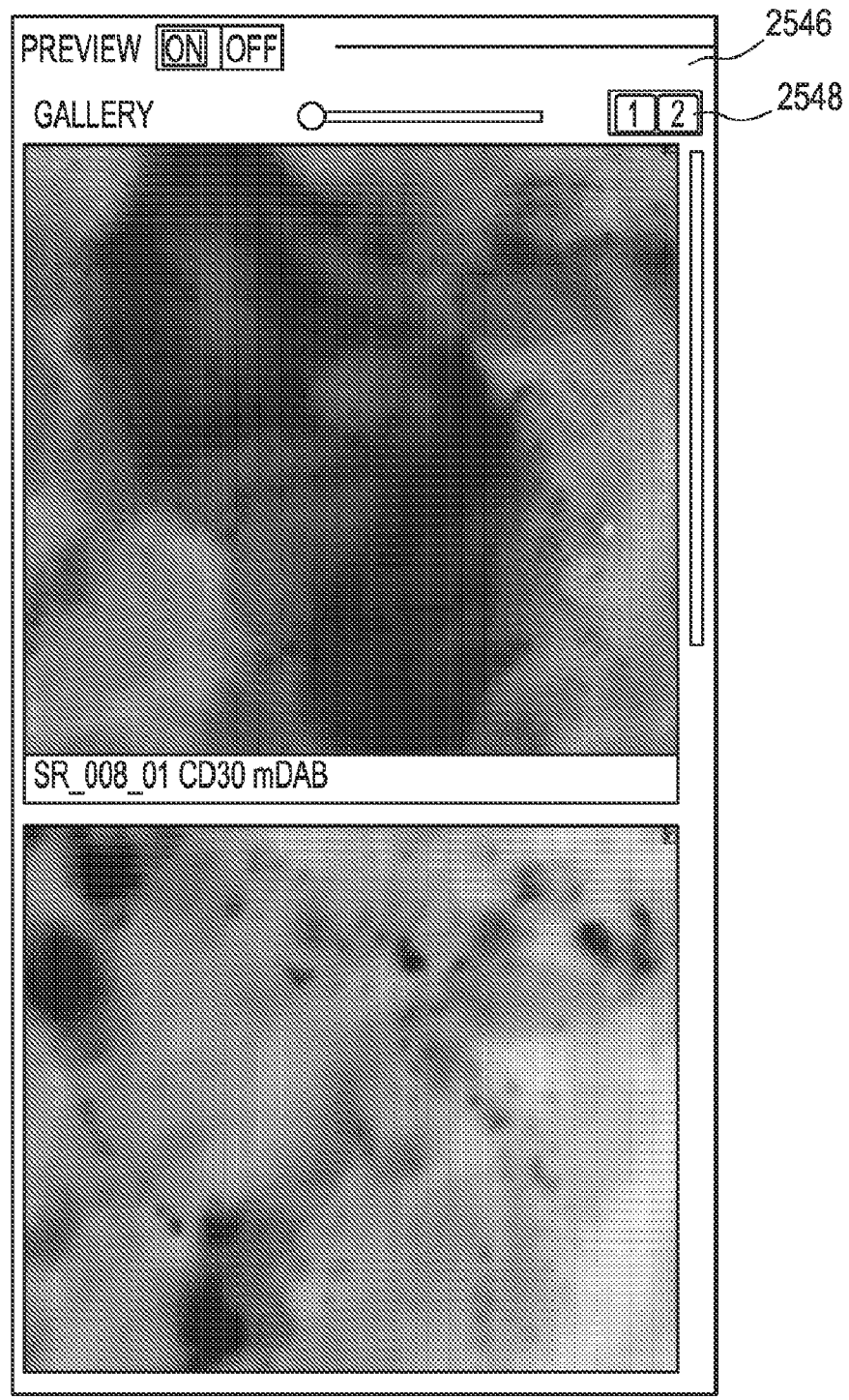
FIG. 37 depicts the display of captured thumbnail images using the annotations tab of the present invention.
Figure 38:
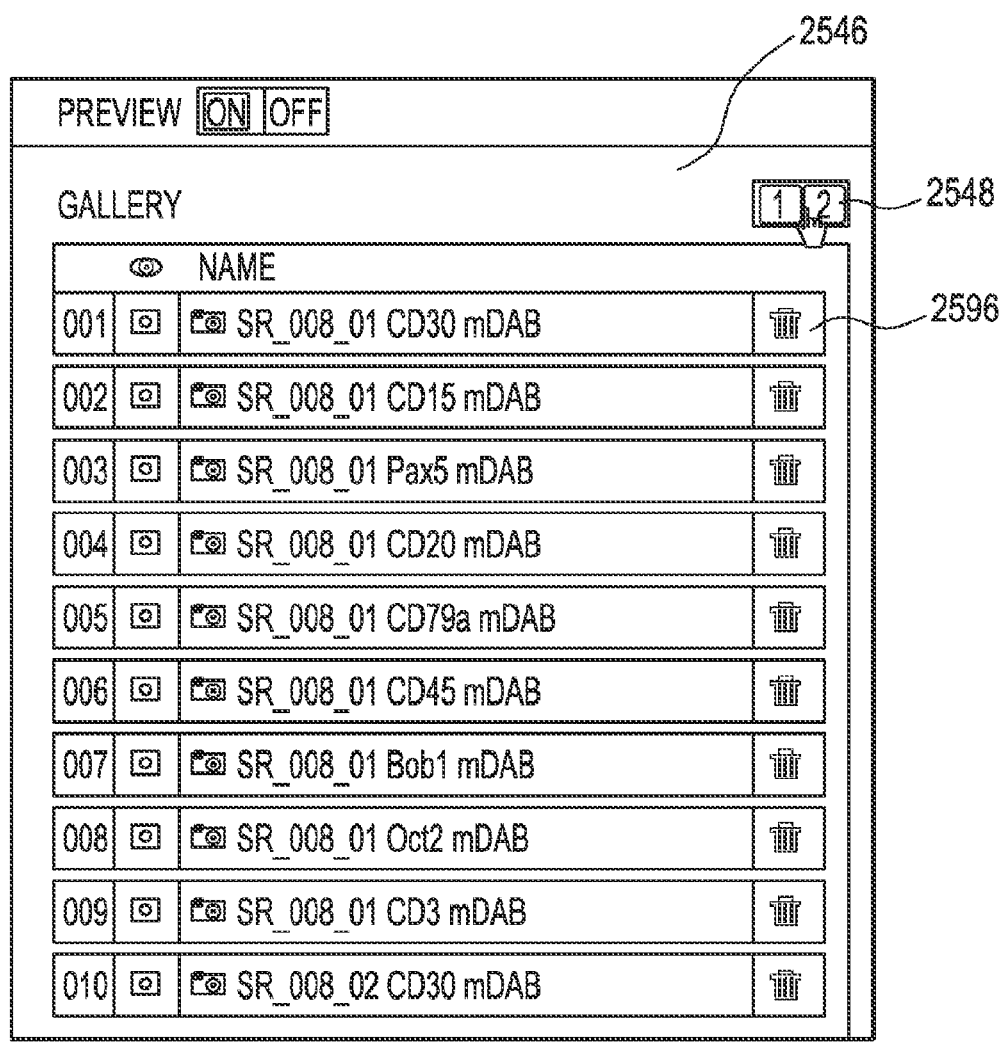
FIG. 38 depicts the display of the captured images in a list format.
Figure 39:
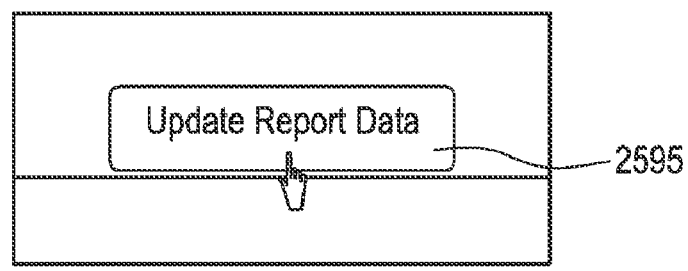
FIG. 39 depicts the ability to upload all of the captured images the pathologist into a case report.

After the pathologist determines regions of interest that are necessary to include in a case report, they can capture the images displayed on GUI 2500 with Snapshot feature of the present invention. FIG. 34 shows two different snapshots that were captured, as outlined in the boxes 2580 and 2582 on the main image panel 2502. It also shows the list of the snapshots that were acquired on the panel 2504. With the tab 2509 selected, the Pathologists can capture images using the snapshot in one of two ways. The first way is to capture the resulting thumbnail images 2505 of the Digital Prism. To do so, they move the digital prism box 2565 to the cells of interest, resize the prism to properly frame the image, and save the thumbnail location. They can then click the first snapshot capture button 2590 and the same region is captured for all 9 biomarkers, as depicted in the region manager panel 2504 portion of GUI 2500, as shown in FIG. 35. The second way the pathologist can capture images is by capturing an entire field, one stain at a time. This is useful when it is necessary to see an entire region, not just a single cell or two. To capture the entire field, they simply click the second snapshot capture button 2592 on main image panel 2502, as shown in the portion of main image panel 2502 in FIG. 36. All of the images that are captured can be reviewed by clicking the snapshot tab 2509. The images can be viewed in a thumbnail image format, as shown in FIG. 37. Alternatively, the images may be viewed as a descriptive list, as shown in FIG. 38. The gallery subpanel 2546 of report snapshot tab 2509 includes a gallery toggle 2548 which allows a user to select between a display of thumbnail images (as shown in FIG. 37) or a descriptive list of images (as shown in FIG. 38). From the list shown in FIG. 38 the pathologist can erase any captured image by clicking on the associated trash can icon 2596. Also the user may alter any image that they would like by highlighting the image on the list, clicking the edit toggle 2598, and then adjusting position of the corresponding box on the main image display 2502. Additionally, tab 2509 also provides a quick save button 2597 which allows the user to save the image to a local media. Once the pathologist is content with all of the captured images, they can upload the images to the case report with a single click of the Update Report Data button 2595, as depicted in FIG. 39.

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by $\frac{1}{20}$th, $\frac{1}{10}$th, $\frac{1}{5}$th, $\frac{1}{3}$rd, $\frac{1}{2}$nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

What is claimed is:

1. A computer-implemented method for displaying expression levels of one or more biomarkers in a field of view corresponding to an image, or a portion of an image, of a biological specimen, the method comprising:
   rendering a graphical user interface on a visual display device, the graphical user interface comprising a main image panel and a biomarker panel;
   receiving user input selecting a field of view corresponding to a selected biological specimen;
   rendering, on the main image panel, a first image of the selected field of view corresponding to the biological specimen;
   rendering, overlaid on the first image in the main image panel, an interest region selection component enabling a user to select a first region within the first image;
   rendering, on the biomarker panel, a first set of thumbnail images corresponding to the first region in the first image, the first set of thumbnail images representing expression levels of a set of biomarkers;

receiving user input, on the main image panel, selecting a second region in the first image; and based on the user input selecting the second region in the first image, updating the biomarker panel to replace the first set of thumbnail images with a second set of thumbnail images corresponding to the second region in the first image and representing expression levels of the set of biomarkers.

2. The method of claim 1, wherein the interest region selection component delineates a smaller region within the first image.

3. The method of claim 1, wherein the user input selecting the second region comprises:

user input selecting the interest region selection component; and user input to drag the interest region selection component overlaid on the first image from the first region to the second region in the first image.

4. The method of claim 1, wherein the user input selecting the second region comprises:

user input selecting the first image; and user input to drag the first image underlying the interest region selection component so that the second region in the first image lies under the interest region selection component.

5. The method of claim 1, further comprising:

overlaying, on the first image, representations of one or more morphological features in the selected field of view of the biological specimen.

6. The method of claim 5, wherein the second region is selected to include a morphological feature represented on the first image.

7. The method of claim 6, wherein the morphological feature is a cell.

8. The method of claim 6, wherein the morphological feature is a collection of cells.

9. The method of claim 6, wherein the morphological feature is a sub-cellular component.

10. The method of claim 9, wherein the sub-cellular component is a nucleus, cytoplasm or membrane.

11. The method of claim 1, wherein the first and second sets of thumbnail images are arranged in a defined pattern in the biomarker panel.

12. The method of claim 11, wherein the defined pattern is a grid-like pattern.

13. The method of claim 1, wherein the first and second sets of thumbnail images are organized in the biomarker panel based on a stored setting indicating an order in which the thumbnail images are to be represented.

14. The method of claim 13, wherein the order is based on a relevance of at least one of the biomarkers in assessing a clinical outcome.

15. The method of claim 1, further comprising:

receiving user input, directly on the biomarker panel, to reorder one or more of the thumbnail images in the second set of thumbnail images; and in response to the user input, reordering the second set of thumbnail images in the biomarker panel.

16. The method of claim 1, further comprising:

receiving user input, directly on the biomarker panel, to remove a first thumbnail image; and in response to the user input, updating the biomarker panel to remove the selected first thumbnail image.

17. The method of claim 1, further comprising:

receiving user input to select a visualization type for the biomarker panel; and in response to the user input, updating the biomarker panel to represent the second set of thumbnail images in the selected visualization type.

18. The method of claim 17, wherein the selected visualization type simultaneously displays expression levels of two or more biomarkers as a blended color image.

19. The method of claim 17, wherein the selected visualization type displays expression levels of a biomarker as levels of a color.

20. The method of claim 17, wherein the selected visualization type displays expression levels of a biomarker as a heatmap.

21. The method of claim 20, wherein the heatmap is a discrete, continuous or binary heatmap.

22. The method of claim 17, wherein the selected visualization type displays a simulated bright-field image of the field of view.

23. The method of claim 1, further comprising:

updating a size of the biomarker panel based on the number of thumbnail images in the second set of thumbnail images.

24. The method of claim 1, further comprising:

locking the interest region selection component relative to the underlying first image to fixedly overlay the second region in the first image.

25. The method of claim 1, further comprising:

receiving user input, directly on the biomarker panel, to change a scale of a first thumbnail image in the second set of thumbnail images; and in response to the user input, updating the biomarker panel to change the scale of the selected first thumbnail image.

26. The method of claim 25, further comprising:

in response to the user input, updating the biomarker panel to change a scale of the remaining thumbnail images in the second set of thumbnail images to rescale them to the same scale as the rescaled first thumbnail image.

27. The method of claim 1, further comprising:

receiving user input, on the interest region selection component, changing a portion of the first image displayed in a first thumbnail image in the second set of thumbnail images; and in response to the user input, updating the biomarker panel to change the portion of the first image displayed in the selected first thumbnail image.

28. The method of claim 27, further comprising:

in response to the user input, updating the biomarker panel so that remaining thumbnail images in the second set of thumbnail images display the same portion of the first image displayed in the updated first thumbnail image.

29. The method of claim 1, wherein the first and second sets of thumbnail images are displayed at the same scale as the first image.

30. The method of claim 1, wherein the first and second sets of thumbnail images are displayed at a different scale than the first image.

31. The method of claim 1, further comprising:

rendering, on the graphical user interface, an image navigation component displaying a representation of the biological specimen; and receiving, directly on the image navigation component, a user input selecting the field of view of the biological specimen for display on the main image panel.

32. The method of claim 31, wherein the image navigation component indicates a location of the selected field of view within the biological specimen.

33. The method of claim 1, wherein the expression levels of the biomarkers are represented at a pixel level.

34. The method of claim 1, wherein the graphical user interface is rendered on a computing device, the method further comprising:
requesting data on the expression levels of the biomarkers from the computing device to a remote server storing the data; and
receiving, at the computing device, the data on the expression levels from the server.

35. The method of claim 34, wherein the requested data indicates the expression levels of the first biomarker and correspond to the selected field of view of the biological specimen for display in the main image panel, and wherein the requested data excludes data corresponding to a region of the biological specimen outside the selected field of view.

36. The method of claim 34, wherein the requested data indicates the expression levels of the set of biomarkers and correspond to the selected second region for display in the biomarker panel.

37. The method of claim 34, wherein the requested data is received as streaming data.

38. The method of claim 34, wherein the server is a tile server and wherein portions of data on the expression levels of the biomarkers are stored on the server as tiles of image data.

39. The method of claim 1, wherein the first image represents expression levels of a default biomarker selected from the set of biomarkers.

40. The method of claim 1, wherein the first image represents expression levels of a user-selected biomarker.

41. The method of claim 1, further comprising:
receiving user input, directly on the biomarker panel, selecting a first thumbnail image representing expression levels of a second biomarker; and
in response to the user input, updating the main image panel to display a second image of the selected field of view, the second image representing expression levels of the second biomarker selected by the user input.

42. The method of claim 1, further comprising:
overlaying, on the first image, results of a segmentation analysis of the first image.

43. A computer system for displaying expression levels of one or more biomarkers in a field of view corresponding to an image, or a portion of an image, of a biological specimen, the system comprising:
a visual display device; and
a computer processor coupled to the visual display device and programmed to:
render a graphical user interface on the visual display device, the graphical user interface comprising a main image panel and a biomarker panel;
receive user input selecting a field of view corresponding to a selected biological specimen;
render, on the main image panel, a first image of the selected field of view corresponding to the biological specimen;
render, overlaid on the first image in the main image panel, an interest region selection component enabling a user to select a first region within the first image;
render, on the biomarker panel, a first set of thumbnail images corresponding to the first region in the first image, the first set of thumbnail images representing expression levels of a set of biomarkers;
receive user input, on the main image panel, selecting a second region in the first image; and
based on the user input selecting the second region in the first image, update the biomarker panel to replace the first set of thumbnail images with a second set of thumbnail images corresponding to the second region in the first image and representing expression levels of the set of biomarkers.

44. One or more non-transitory computer-readable media having encoded thereon one or more computer-executable instructions that, when executed on a computing device, perform a method for displaying expression levels of one or more biomarkers in a field of view corresponding to an image, or a portion of an image, of a biological specimen, the method comprising:
rendering a graphical user interface on a visual display device, the graphical user interface comprising a main image panel and a biomarker panel;
receiving user input selecting a field of view corresponding to a selected biological specimen;
rendering, on the main image panel, a first image of the selected field of view corresponding to the biological specimen;
rendering, overlaid on the first image in the main image panel, an interest region selection component enabling a user to select a first region within the first image;
rendering, on the biomarker panel, a first set of thumbnail images corresponding to the first region in the first image, the first set of thumbnail images representing expression levels of a set of biomarkers;
receiving user input, on the main image panel, selecting a second region in the first image; and
based on the user input selecting the second region in the first image, updating the biomarker panel to replace the first set of thumbnail images with a second set of thumbnail images corresponding to the second region in the first image and representing expression levels of the set of biomarkers.

* * * * *